(12) United States Patent
Jessop et al.

(10) Patent No.: US 8,580,124 B2
(45) Date of Patent: Nov. 12, 2013

(54) SWITCHABLE HYDROPHILICITY SOLVENTS AND METHODS OF USE THEREOF

(75) Inventors: Philip G. Jessop, Kingston (CA); Lam N. Phan, Oshawa (CA); Andrew J. Carrier, Trenton (CA); Rui Resendes, Kingston (CA); Dominik Wechsler, Kingston (CA)

(73) Assignees: Queen's University at Kingston, Kingston, ON (CA); GreenCentre Canada, Kingston, ON (CA)

( * ) Notice: Subject to any disclaimer, the term of this patent is extended or adjusted under 35 U.S.C. 154(b) by 149 days.

(21) Appl. No.: 12/914,948

(22) Filed: Oct. 28, 2010

(65) Prior Publication Data

US 2011/0257334 A1 Oct. 20, 2011

Related U.S. Application Data

(60) Provisional application No. 61/255,623, filed on Oct. 28, 2009, provisional application No. 61/311,178, filed on Mar. 5, 2010.

(30) Foreign Application Priority Data

Oct. 28, 2009 (CA) ................................. 2683660

(51) Int. Cl.
*C02F 1/20* (2006.01)
(52) U.S. Cl.
USPC .......... 210/750; 210/198.1; 210/642; 521/40; 521/40.5; 521/45; 521/48; 521/49.5; 209/4; 209/18; 427/331; 528/499; 203/39; 434/276; 434/365
(58) Field of Classification Search
USPC ............... 210/198.1, 642, 750; 134/10, 95.1; 264/102; 203/39; 564/225, 238, 499; 521/40, 40.5, 45, 48, 49.5; 528/480, 528/492, 499, 502 R
See application file for complete search history.

(56) References Cited

U.S. PATENT DOCUMENTS

| | | | |
|---|---|---|---|
| 2,630,386 | A | 3/1953 | Walker |
| 2,801,217 | A | 7/1957 | Nelson |
| 2,949,427 | A | 8/1960 | Andersen et al. |
| 3,060,007 | A | 10/1962 | Feedman |
| 3,143,461 | A | 8/1964 | Berg |
| 3,228,956 | A | 1/1966 | Monroe |

(Continued)

FOREIGN PATENT DOCUMENTS

| | | |
|---|---|---|
| CA | 2539418 | 9/2007 |
| DE | 277691 | 4/1990 |

(Continued)

OTHER PUBLICATIONS

Anton, P.; Koeberle, P.; Laschewsky, A. Progress in Colloid & Polymer Science 1992, 89, 56-59.

(Continued)

*Primary Examiner* — Frances Tischler
(74) *Attorney, Agent, or Firm* — Angela Lyon; Carol Miernicki Steeg; Stephanie White

(57) ABSTRACT

A solvent that reversibly converts from a hydrophobic liquid form to hydrophilic liquid form upon contact with water and a selected trigger, e.g., contact with $CO_2$, is described. The hydrophilic liquid form is readily converted back to the hydrophobic liquid form and water. The hydrophobic liquid is an amidine or amine. The hydrophilic liquid form comprises an amidinium salt or an ammonium salt.

58 Claims, 29 Drawing Sheets

(56) References Cited

U.S. PATENT DOCUMENTS

| | | |
|---|---|---|
| 3,231,487 A | 1/1966 | Nettles |
| 3,385,891 A | 5/1968 | Fenton |
| 3,598,800 A | 8/1971 | Gatzi |
| 3,884,974 A | 5/1975 | Heffe |
| 4,079,166 A | 3/1978 | Gibson et al. |
| 4,499,274 A | 2/1985 | Feth et al. |
| 4,623,678 A | 11/1986 | Moore et al. |
| 4,770,670 A | 9/1988 | Hazbun et al. |
| 5,308,869 A | 5/1994 | Keana et al. |
| 5,435,920 A | 7/1995 | Penth |
| 5,457,083 A | 10/1995 | Muia et al. |
| 5,905,061 A | 5/1999 | Patel |
| 6,218,342 B1 | 4/2001 | Patel |
| 6,499,546 B1 | 12/2002 | Freeman et al. |
| 6,890,969 B2 | 5/2005 | Rabasco et al. |
| 7,700,533 B2 | 4/2010 | Egbe et al. |
| 7,982,069 B2 | 7/2011 | Jessop et al. |
| 2002/0099113 A1 | 7/2002 | Rabasco et al. |
| 2006/0293208 A1 | 12/2006 | Egbe et al. |
| 2007/0092801 A1 | 4/2007 | Tipton |
| 2008/0058549 A1 | 3/2008 | Jessop et al. |
| 2008/0197084 A1 | 8/2008 | Jessop |
| 2009/0136402 A1 | 5/2009 | Heldebrant |
| 2010/0240566 A1 | 9/2010 | Meine et al. |
| 2011/0076214 A1 | 3/2011 | Yu et al. |
| 2011/0257334 A1 | 10/2011 | Jessop et al. |
| 2012/0116076 A1 | 5/2012 | Jessop et al. |

FOREIGN PATENT DOCUMENTS

| | | |
|---|---|---|
| DE | 4028904 C1 | 7/1992 |
| JP | 2004-59750 | 2/2004 |
| WO | WO2004106288 | 12/2004 |
| WO | WO2007056859 | 8/2008 |
| WO | WO2008068411 | 5/2009 |

OTHER PUBLICATIONS

Aydogan, N.; Abbott, N. L. Langmuir 2001, 17, 5703-5706.

Dorrance, Nancy, "New chemical process makes manufacturing environmentally friendly", Queen's Gazette XXXVI (13): 8 (Sep. 12, 2005).

Dumont, P., et al., "Synthesis and study of the antileukemic activity of N,N'-substituted amidines and bisamidines", Journal de Pharmacie de Belgique, 1986, vol. 40, No. 6, pp. 373-386.

Datwani, S. S.; Truskett, V. N.; Rosslee, C. A.; Abbott, N. L.; Stebe, K. J. Langmuir 2003, 19, 8292-8301.

Defrise-Quertain, F., et al., "Vesicle formation by double long-chain amidines." J. Chem. Soc., Chem. Comm., 1060-1062 (1986).

Edwards, A., et al., "Mechanistic studies of the corrosion inhibitor oleic imidazoline." Corrosion Science 36(2): 315-325 (1994).

Hori, Y., et al., "New Method . . . Using DBU (6th report) Reversible Immobilization of Carbon Dioxide Gas by Forming Carbonate, Carbamate Salt." Chem. Exp. 1(3): 173-176 (1986).

Heldebrant et al., "The Reaction of 1,8-Diazabicyclo[5.4.0]undec-7-ene (DBU) with Carbon Dioxide", Journal of Organic Chemistry, 2005, 70, pp. 5335-5338.

Hill, A. J., et al., "Some amidines of the holocaine type. I", Journal of the Chemical Society, 1926, vol. 48, pp. 732-737.

Jessop, P. G., Kyzycz, L., Rahami, Z. G., Schoenmakers, D., Boyd, A. R., Wechsler, D., Holland, A. M. "Tertiary Amine solvents having switchable hydrophilicity" Green Chem. 2011, vol. 13, p. 619-623.

Jaroszewska-Manaj, J. et al. "Amidines. Part 41. Effects of substitution . . . " J. Chem. Soc., Perkin Trans. 2, 1186-1191 (2001).

Jessop, P. G., et al., "A solvent having switchable hydrophilicity", Green Chemistry, 2010, vol. 12, pp. 809-814.

Jessop et al., "Green Chemistry Reversible nonpolar-to-polar solvent", Nature, Aug. 25, 2005, 436, 7054, Research Library, p. 1102.

Kucera, J. "Reverse Osmosis: Industrial Applications and Processes" Wiley InterScience, Published in year 2010, [online] http://books.google.ca/books?id=d8mA2YRIVI7VIC&printsec=frontcover&dq=reverse+osmosis&hl= en&ei=emECT7u6JoWWOQG3g1WzBw&sa= X&oi=book_result&ct=book-thumbnail&resnum=1&ved=OCE0Q6wEwA A#v=onepage&q=reverse%20osmosis&f=false.

Li, X., Wang. S,.and Li, Z. "Study on the synthesis of copolymer containing N-substituted acrylamide component", Polymer Communications, No. 2, 190-195. cf. whole document.

Lottermoser, A., "The Influence of Atmospheric Carbonic Acid Upon the 'Surface Tension of Aqueous Solutions of Sodium' Salts of Fatty Acids"; Trans. faraday Soc. 31, 200-204.(1934).

Liu, Y. et al., "Switchable Surfactants" Science 313: 958-960 (2006).

Lu, J. et al., "Tunable solvents for homogeneous catalyst recycle", Industrial & Engineering Chemistry Research, 2004, vol. 43: 1586-1590.

Lopez, D.A., et al., "Inhibitors performance in CO2 corrosion EIS studies on the interaction between their molecular structure and steel microstructure." Corrosion Science 47: 735-755 (2005).

Li, S. et al., "Bronsted Guanidine Acid-Base Ionic Liquids: Novel Reaction . . . Catalyzed Heck Reaction." Organic Letters 8(3): 391-394 (2006).

Main, A.D., et al., "Simple Preparation . . . Carbonate." unpublished material from J.C. Linehan, Pacific Northwest National Laboratory (2001).

Minkenberg, C. B.; Florusse, R. E.; Koper, G. J. M.; van Esch, J. H. J. Am. Chem. Soc. 2009, 131, 11274-11275.

Mercer, S.M., Jessop, P.G. ""Switchable Water": Aqueous Solutions of Switchable Ionic Strength", ChemSusChem, vol. 3, Issue 4, p. 467-470, Apr. 2010 (Published online Feb. 23, 2010, DOI 10.1002/cssc.201000001) ISSN: 18645631.

Munshi, P., et al., "Hydrogenation of Carbon Dioxide Catalyzed by Ruthenium Trimethylphosphine . . . Amines." J. Am.Chem.Soc. 124(27): 7963-7971 (2002).

Oszczapowicz, J. et al., "Amidines. Part 13. Influence of Substitution" J. Chem. Soc., Perkin Trans. II, 1643-1646 (1984).

Phan, L., Andreatta, J. R., Horvey, L. K., Edie, C. F., Luco, A. L., Mirchandani, A., Darensbourg, D. J., and Jessop, P. G. "Switchable-Polarity Solvents Prepared with a Single Liquid Component", J. Org. Chem. 2008, vol. 73, p. 127-132 cf. p. 129, col. 2, lines 43-47.

Pincet, F., et al., "Spontaneous and reversible switch from amphiphilic to oil-like structures." Phys. Rev. Letts. 95: 218101-1-218101-4 (2005) (publication date: Nov. 15, 2005).

Cheng, Z.; Ren, B.; Gao, M.; Liu, X.; Tong, Z. Macromolecules 2007, 40, 7638-7643.

Ghosh, S.; Irvin, K.; Thayumanavan, S. Langmuir 2007, 23, 7916-7919.

Poteau, S., et al., "Influence of pH on Stability and Dynamic Properties of Asphaltenes and Other Amphiphilic Molecules at the Oil-Water Interface." Energy & Fuels 19: 1337-1341 (2005).

Perez, E.R., et al., "Activation of Carbon Dioxide by Bicyclic Amidines." J. Org. Chem. 69(23): 8005-8011 (2004).

Pollet, P. et al., "Organic aqueous tunable solvents (OATS): A vehicle for coupling reactions and separations", Accounts of Chemical Research, Sep. 2010, vol. 43, No. 9, pp. 1237-1245.

Pham, L, et al., "Soybean oil extraction and separation using switchable or expanded solvents", Green Chemistry, 2009, vol. 11, pp. 53-59.

Sakai, H.; Matsumura, A.; Yokoyama, S.; Saji, T.; Abe, M. J. Phys. Chem. B 1999, 103, 10737-10740.

Schroth, W., et. al., "Dimethylammonium-dimethylcarbamat (Dimcarb) als Losungs- und Extraktionsmittel" Z. Chem. 29(2): 56-57 (1989).

Sakai, H.; Abe, M. Control of Molecular Aggregate Formation and Solubilization using Electro- and Photoresponsive Surfactant Mixtures. In Mixed Surfactant Systems; Abe, M., Scamehorn, J. F., Eds.; Surfactant Science Series; Marcel Dekker: New York, 2005; vol. 124, pp. 507-543.

Saji, T.; Hoshino, K.; Aoyagui, S. J . Am. Chem. Soc. 1985, 107, 6865-6868.

Scoggins, M.W., "A Rapid Gas Chromatographic Analysis of Diastereomeric Diamines." J. Chromatogr. Sci., 13:146-148 (1975).

Tsuchiya K.; Orihara Y.; Kondo Y.; Yoshino N.; Ohkubo T.; Sakai H.; Abe M. J. Am. Chem. Soc. 2004, 126, 12282-12283.

(56) References Cited

OTHER PUBLICATIONS

Schmittel, M., et al., "N,N'-Dimethyl-2,3-dialkylpyrazinium salts as redox-switchable surfactants? Redox, spectral, EPR and surfactant properties." Chem. Comm. 5650-5652 (2005).
Tetko I.V. and Tanchuk V.Y., J. Comput. Aid. Mol. Des., 2005, 19, 453-463.
Texter J. (editor) Chapter 2 by Holmberg, K., "Cleavable Surfactants." in Reactions and synthesis in surfactant systems: p. 45-58 (2001).
Uemura, Y. et al., "Preparation of Resins Having Various Phosphonium Groups and Their Adsorption and. lution Behavior for Anionic Surfactants", Journal of Applied Polymer-Science 72, 371-378-0999).
Zaki, Nael N. et al., "A Novel Process for Demulsification of Water-in-Crude Oil 'Emulsions by Dense Carbon Dioxide", Ind. Eng. Chem. Res. 42, 6661-6672 (2003).
International Search Report for PCT/CA2006/001877 filed Nov. 15, 2006.
English translation of second Chinese Office Action dated Jan. 17, 2012 for CN Appl. No. 200680046495.5.
English translation of First Chinese Office Action dated Oct. 18, 2010 for CN Appl. No. 200680046495.5.
Dexter, A. F.; Middelberg, A. P. J. Ind Eng Chem Res 2008, 47, 6391-6398.
Dexter, A. F.; Malcolm, A. S.; Middelberg, A. P. J. Nat Mater 2006, 5, 502-506.
Fowler, C. I.; Muchemu, C. M.; Miller, R. E.; Phan, L.; O'Neill, C.; Jessop, P. G.; Cunningham, M. F. Macromolecules 2011, 44, 2501-2509.
Harjani, J. R.; Liang, C.; Jessop, P. G. J. Org. Chem. 2011, 76, 1683-1691.
L. M. Scott, M.Sc. Thesis, Queen's University, 2009.
Mihara, M.; Jessop, P.; Cunningham, M. Macromolecules 2011.
Mirarefi, P.; Lee, C. T. Jr. Biochimica et Biophysica Acta, Proteins and Proteomics, 2010, 1804, 106-114.
Arthur, T, Harjani, J., Jessop, P.G., and Hodson, P.V., Green Chem., 2012, DOI: 10.1039/CIGC15620A.
Cook, M.J.; Katritzky, A.R.; Nadji, S.J. Chem. Soc., Perkin Trans. 2 1976, 211-214.
Hall Jr., H.J. Am. Chem. Soc. 1957, 79, 5441-5444.
Tanrisever, T.; Okay, O.; Soenmezoglu, I.C. J Appl Polym Sci 1996, 61, 485-493.
PCT International Search Report for International Application No. PCT/CA2010/001707 filed on Oct. 28, 2010.
PCT Written Opinion of the International Searching Authority for International Application No. PCT/CA2010/001707.
Examiner's Requisition dated Feb. 29, 2012 for Canadian Patent Application No. 2,527,144.
European Search Report dated Jul. 12, 2010 for European Patent Application No. 06804740.6.
Office Action (Restriction Requirement) dated Dec. 23, 2009 on U.S. Appl. No. 11/599,623.
Office Action dated Jun. 10, 2010 on U.S. Appl. No. 11/599,623.
Office Action (Restriction Requirement) dated Jun. 16, 2008 on U.S. Appl. No. 11/717,172.
Office Action dated Mar. 3, 2009 on U.S. Appl. No. 11/717,172.
Office Action dated Dec. 30, 2009 on U.S. Appl. No. 11/717,172.
Office Action dated Feb. 28, 2012 on U.S. Appl. No. 13/172,090.
Office Action dated Sep. 5, 2012 on U.S. Appl. No. 13/172,090.
Office Action dated May 14, 2012 on Canadian Application Serial No. 2,539,418.
International Search Report for PCT/CA2011/050075 filed on Feb. 10, 2011.
International Search Report for PCT/CA2011/050777 filed on Dec. 15, 2011.
El-Aasser, M., Lovell, P., Eds.; Emulsion Polymerization and Emulsion Polymers; John Wiley & sons, Inc.: Chichester, NY, 1997. p. 222-227.
Liang, C.: "Cationic and Anionic Carbon Dioxide Responsive Switchable Surfactants", M.Sc. Thesis, Queen's University, Kingston, Ontario, 2010.
Qin, Y., Yang H., Ji, J., Yao, S., Kong, Y. and Wang, Y., Tenside Surf. Det., 2009, 46, 294-296.
Phan, L.N.:"CO2-Triggered Switchable Solvent Systems and Their Applications", M.Sc. Thesis, Queen's University, Kingston, Ontario, prepared Feb. 2008 embargoed from publication until publication date Oct. 27, 2008.

US 8,580,124 B2

SWITCHABLE HYDROPHILICITY SOLVENTS AND METHODS OF USE THEREOF

RELATED APPLICATIONS

This application claims the benefit of the filing date of U.S. Provisional Patent Application No. 61/255,623, filed on Oct. 28, 2009, Canadian Patent Application No. 2,683,660, filed on Oct. 28, 2009, and U.S. Provisional Patent Application No. 61/311,178, filed on Mar. 5, 2010, the contents of which are incorporated herein by reference in their entirety.

FIELD OF THE INVENTION

The field of the invention is solvents, and specifically solvents that can be reversibly converted between hydrophobic and hydrophilic forms.

BACKGROUND OF THE INVENTION

Conventional solvents have fixed physical properties which can lead to significant limitations in their use as media for reactions and separations. Many chemical production processes involve multiple reactions and separation steps, and often the type of solvent that is optimum for any one step is different from that which is optimum for the next step. Thus it is common for the solvent to be removed after each step and a new solvent added in preparation for the next step. This removal and replacement greatly adds to the economic cost and environmental impact of the overall process. Therefore, there exists a need for a solvent that can change its physical properties.

Solvents are commonly used to dissolve material in manufacturing, cleaning, dyeing, extracting, and other processes. In order for a solvent to dissolve a material quickly, selectively, and in sufficient quantity, it is usually necessary for the solvent to have particular physical properties. Examples of such properties include hydrophobicity, hydrophilicity, dielectric constant, polarizability, acidity, basicity, viscosity, volatility, hydrogen-bond donating ability, hydrogen-bond accepting ability, and polarity. At some point in such a process after the dissolution, separation of the material from the solvent may be desired. Such a separation can be expensive to achieve, especially if the solvent is removed by distillation, which requires the use of a volatile solvent, which can lead to significant vapor emission losses and resulting environmental damage e.g., through smog formation. Furthermore, distillation requires a large input of energy. It would therefore be desirable to find a non-distillative route for the removal of solvents from products. This is particularly difficult if the solvent and the product are both very low in polarity.

US Patent Application Publication No. 2008/0058549 discloses a solvent that reversibly converts from a nonionic liquid mixture to an ionic liquid upon contact with a selected trigger, such as $CO_2$. The nonionic liquid mixture includes an amidine or guanidine or both, and water, alcohol or a combination thereof. However, that document does not provide certain advantages of the present invention as described below.

SUMMARY OF THE INVENTION

In a first aspect, the invention provides a system comprising: means for providing a switchable hydrophilicity solvent (SHS) that is a water-immiscible liquid; means for adding to the SHS an aqueous liquid to form a two-layer liquid mixture; means for exposing the two-layer liquid mixture to $CO_2$ in the presence of water thereby protonating the SHS to form protonated-SHS, which is water-miscible or water-soluble, so that the two-layer liquid mixture forms a single-layer liquid mixture; and means for exposing the single-layer liquid mixture to (i) heat, (ii) a flushing gas, or (iii) heat and a flushing gas, thereby expelling $CO_2$ from the single-layer liquid mixture which leads to deprotonation of the protonated-SHS to form SHS so that the single-layer liquid mixture forms a two-layer liquid mixture; and optionally, means for separating a selected compound from the protonated-SHS prior to reformation of SHS.

In some embodiments the system further comprises means for isolating and transporting each layer of the two layer liquid mixture for reuse. In some embodiments, the aqueous liquid comprises salty water. In some embodiments, the means for exposing to heat comprises means for heating to about 60° C. In some embodiments, the means for exposing to heat comprises means for heating to about 80° C. In some embodiments, the SHS comprises a compound of formula (1), a compound of formula (10), or a combination thereof. In some embodiments, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof. In some embodiments, the SHS comprises N,N-dimethyl-N-cyclohexylamine.

In a second aspect, the invention provides a system for removing a hydrophobic contaminant from a solid material, comprising: means for contacting a mixture of solid material and hydrophobic contaminant with a liquid comprising a liquid switchable hydrophilicity solvent so that at least a portion of the hydrophobic contaminant becomes associated with the liquid to form contaminated liquid; optionally, means for separating the contaminated liquid from residual solid material; means for contacting the contaminated liquid with $CO_2$ in the presence of water to convert a substantial amount of the switchable hydrophilicity solvent from its unprotonated form to its protonated form, resulting in a two-phase liquid mixture having a hydrophobic liquid phase comprising the hydrophobic contaminant, and an aqueous liquid phase; and means for separating the hydrophobic liquid phase from the aqueous liquid phase.

In a third aspect, the invention provides a system for cleaning solid particles that are contaminated by a hydrophobic compound, comprising: means for adding solid particles that are contaminated by a hydrophobic contaminant to the system of the first aspect, wherein the hydrophobic contaminant dissolves in the SHS; means for isolating particles that are substantially contaminant-free; and optionally, means for collecting the substantially pure contaminant that forms as a layer that is distinct from the single-layer liquid mixture comprising protonated-SHS and aqueous liquid.

In some embodiments of the second or third aspects, the solid particles or solid material that are contaminated by a hydrophobic compound comprise oil sands, and the contaminant comprises bitumen. In some embodiments of the second or third aspects, the solid particles or solid material that are contaminated by a hydrophobic compound comprise drilling fines, and the contaminant comprises drilling fluid. In some embodiments of the second or third aspects, the solid particles or solid material that are contaminated by a hydrophobic compound comprise soil contaminated by hydrocarbons, and the contaminant comprises hydrocarbons. In some embodiments of the second or third aspects, the solid particles or solid material that are contaminated by a hydrophobic compound comprise plastic, and the contaminant comprises dirt. In some embodiments of the second or third aspects, the solid particles or solid material that are contaminated by a hydrophobic compound comprise plastic, and the contaminant comprises an odorous compound. In some embodiments of the second or third aspects, the SHS comprises a compound of formula (1), a compound of formula (10), or a combination of a compound of formula (1) and a compound of formula (10), wherein the compound of formula (10) is N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a fourth aspect, the invention provides a system for extracting a selected hydrophobic material from a solid, comprising: means for adding solid particles that comprise a selected hydrophobic material to the system of the first aspect, wherein the hydrophobic material dissolves in the SHS; means for isolating solid particles that are substantially free of the selected hydrophobic material; and means for collecting the substantially pure selected hydrophobic material that forms as a layer that is distinct from the single-layer liquid mixture comprising protonated-SHS and aqueous liquid.

In some embodiments of the fourth aspect, the solid is derived from a seed, nut, plant, algae, or bacterial organism. In some embodiments of the fourth aspect, the system further comprises means for masticating the solid prior to exposing it to SHS. In some embodiments of the fourth aspect, the selected hydrophobic material comprises: nut oil, algae oil, seed oil, vegetable oil, canola oil, soybean oil, or biopolymer. In some embodiments of the fourth aspect, the SHS comprises a compound of formula (1), a compound of formula (10), or a combination thereof. In some embodiments of the fourth aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a fifth aspect, the invention provides a system for isolation of a component in a chemical synthesis, comprising: means for adding reagents of a chemical reaction to the system of the first aspect, wherein at least one component of the chemical reaction dissolves in the SHS; and means for collecting the substantially pure component of the chemical reaction that separates from the single-layer liquid mixture comprising protonated-SHS and aqueous liquid.

In some embodiments of the fifth aspect, the component of the chemical reaction is a product of the chemical reaction. In some embodiments of the fifth aspect, the substantially pure component is a biodiesel. In some embodiments of the fifth aspect, the SHS comprises a compound of formula (1), a compound of formula (10), or a combination thereof. In some embodiments of the fifth aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a sixth aspect, the invention provides a system for isolation of at least one selected plastic from a mixture of plastics, comprising: means for adding to the system of the first aspect a mixture of plastics comprising at least one plastic that is soluble in a switchable hydrophilicity solvent; optionally, means for removal of undissolved plastics; and means for collecting the at least one plastic that precipitates from the single-layer liquid mixture comprising protonated-SHS and aqueous liquid. In some embodiments of the sixth aspect, the at least one plastic that is soluble in a switchable hydrophilicity solvent comprises polystyrene. In some embodiments of the sixth aspect, the SHS comprises a compound of formula (1), a compound of formula (10), or a combination thereof. In some embodiments of the sixth aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a seventh aspect, the invention provides a system for adding a hydrophobic compound to a solid material, comprising: means for adding a hydrophobic compound to the system of the first aspect; and means for adding a solid material to the system of the first aspect such that the solid material contacts the hydrophobic compound and become at least partially coated or impregnated by the hydrophobic compound; wherein after exposure of the SHS to $CO_2$ and consequent migration of protonated-SHS to the aqueous layer, solid material that is at least partially coated or impregnated by the hydrophobic compound is collected.

In some embodiments of the seventh aspect, the solid material is a textile and the hydrophobic compound is a dye. In some embodiments of the seventh aspect, the solid material is a textile and the hydrophobic compound is a corrosion inhibitor. In some embodiments of the seventh aspect, the solid material is a vesicle. In some embodiments of the seventh aspect, the solid material is a polymer bead. In some embodiments of the seventh aspect, the hydrophobic compound is a corrosion inhibitor, surface stabilizer, mordant, preservative, antioxidant, enzyme, antigen, or brightener. In some embodiments of the seventh aspect, the solid material is suitable for use in drug delivery and the hydrophobic compound is drug. In some embodiments of the seventh aspect, the SHS comprises a compound of formula (1), a compound of formula (10), or a combination thereof. In some embodiments of the seventh aspect, the SHS comprises N-ethylpiperidine, N,N, N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In an eighth aspect, the invention provides a system for obtaining dissolved polymeric foam, comprising: means for contacting polymeric foam with a switchable hydrophilicity solvent so that the polymeric foam dissolves to form a liquid mixture; optionally, means for mixing the liquid mixture; and means for transporting the liquid mixture into a separate vessel.

In some embodiments of the eighth aspect, the means for transferring comprises a pump for pumping the liquid mixture into a separate vessel. In some embodiments of the eighth aspect, the system is portable. In some embodiments of the eighth aspect, the portable system comprises means for switching the SHS from its protonated hydrophilic form to its hydrophobic form. In some embodiments of the eighth aspect, the portable system further comprises means for switching the SHS from its hydrophobic liquid to its protonated hydrophilic form. In some embodiments of the eighth aspect, the polymeric foam is expanded polystyrene, extruded polystyrene foam, polystyrene foam packing chips, Styrofoam™, rigid polystyrene foam, high impact thin polystyrene, or polystyrene foam packing chips. In some embodiments of the eighth aspect, the SHS comprises a compound of formula (1), a compound of formula (10), or a combination thereof. In some embodiments of the eighth aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a ninth aspect the invention provides a method of obtaining a polymer from its source cells, comprising: contacting bacteria that have produced polymer, or a lysate of said bacteria, with a switchable hydrophilicity solvent in which the polymer dissolves, to form a mixture; optionally removing solid debris from the mixture to form a liquid comprising the switchable hydrophilicity solvent and dissolved polymer; contacting the liquid with $CO_2$ in the presence of water to switch the switchable hydrophilicity solvent to its hydrophilic form, in which the polymer is immiscible, to form a two phase liquid mixture; and collecting the polymer.

In some embodiments of the ninth aspect, the polymer comprises polyhydroxyalkanote. In some embodiments of the ninth aspect, the bacteria are *Cupriavidus necator* or *Pseudomonas putida*. In some embodiments of the ninth aspect, the SHS comprises a compound of formula (1), a compound of formula (10), or a combination thereof. In some embodiments of the ninth aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In a first broad expression of the invention switchable hydrophilicity/hydrophobicity compounds and methods of preparing and using such compounds are provided. The compounds are based on amidine or amine and switch between a hydrophobic form (amidine or amine) and a hydrophilic form which is a salt of the amidine or amine (amidinium salt or ammonium salt) in response to a selected trigger. The hydrophobic form is in a liquid state. When prepared as described hereinbelow, the hydrophilic form can be provided as an aqueous solution of a salt below 100° C., e.g., at room temperature. The trigger to change from hydrophobic form to hydrophilic form may be exposure of the amidine form to $CO_2$, $CS_2$, or COS. Given its convenience, $CO_2$ is especially preferred. The compounds of embodiments of the invention are not only switchable, but reversibly so, and removal of the trigger, e.g., removing $CO_2$, causes the hydrophilic form to switch to the hydrophobic form. The hydrophobic form is sufficiently hydrophobic that is immiscible with water and can separate from an aqueous mixture. The hydrophobic form can thus be easily separated from water by decanting. In their hydrophobic form, the compounds of the invention are sufficiently hydrophobic that they are miscible with or can dissolve other hydrophobic compounds and can therefore be used as solvents.

In a second broad expression of the invention switchable hydrophilicity/hydrophobicity compounds and methods of preparing and using such compounds are provided, where the compounds are based on amidine or amine and switch between a first hydrophobic form with no local charges and a second, hydrophilic ionic form in response to a selected trigger. The trigger to change from first form to second, hydrophilic form may be exposure of the first form to $CO_2$, $CS_2$, or COS. Given its convenience, $CO_2$ is especially preferred. The compounds according to this aspect of the invention are not only switchable, but reversibly so, and removal of the trigger, e.g., removing $CO_2$, causes the second, hydrophilic ionic form to switch to the first hydrophobic form. The hydrophobic form is sufficiently hydrophobic that it is immiscible with water and will separate from an aqueous mixture.

It should be understood that it is appropriate for purposes of the present disclosure to call removal of a first trigger a "trigger" itself, in that it causes a change in properties of the compound in question.

Another broad expression of the invention provides a salt that forms a hydrophilic liquid with water wherein, the hydrophilic character of this salt changes in response to a trigger such that it transforms into a hydrophobic liquid and water. Another broad expression of the invention provides a compound that is a hydrophobic liquid. The hydrophobic liquid changes in response to a trigger in the presence of water such that it becomes an aqueous hydrophilic liquid comprising a salt.

According to a tenth aspect, the invention provides a compound of formula (1):

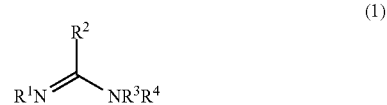

that is water-immiscible; where $R^1$, $R^2$, $R^3$, and $R^4$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; or a substituted or unsubstituted heteroaryl group having from 4 to 10 atoms in the aromatic ring.

The compound of formula (1) is an amidine. The compound of formula (1) is in a liquid state. By "liquid state" is meant that when the compound is water saturated, at a temperature below 70° C., and at a pressure of about 1 atm, it is a liquid.

In some embodiments of the tenth aspect, $R^1$, $R^3$, and $R^4$ are not hydrogen. In certain embodiments of the tenth aspect, the total number of carbon and/or silicon atoms in all substituents $R^1$, $R^2$, $R^3$, and $R^4$ is in the range of 10 to 20. In certain embodiments, two of the R groups in formula (1), together with the amidine-nitrogen or amidine-carbon to which they are attached, are joined and form a ring. In some alternative examples of this embodiment, $R^1$ is joined to $R^2$; $R^1$ is joined to $R^3$; $R^2$ is joined to $R^3$; $R^3$ is joined to $R^4$. In other embodiments, two pairs of R groups each form a ring.

In certain embodiments of the tenth aspect, a compound of formula (1) has a log P value in the range of about 3 to about 7. Compounds having a log P value of less than 3 may be too hydrophilic such that they may be miscible with water. Consequently such liquids would be unsuitable for the present invention because they would offer poor extraction of hydrophobic compounds and could not be separated from water.

Compounds having a log P value of greater than 7 are less preferred because they are more hydrophobic in character such that the hydrophilic ionic form may be less easily miscible with water. In addition, because the hydrophilic form may be a solid compound rather than an ionic liquid, the compounds could be unsuitable for use in the separation methods described herein if they are not water-miscible.

In certain embodiments, the compound of formula (1) has a log P value in the range of about 4.5 to about 6.5.

In certain embodiments of the tenth aspect, the compound of formula (1) is:

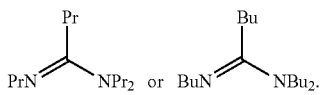

According to a further broad expression of the invention, a salt that is formed by the reaction of carbon dioxide with an amidine and water is provided. This reaction is reversible, such that by removing the $CO_2$, the amidine and water are regenerated.

In an eleventh aspect, the invention provides a salt of formula (2)

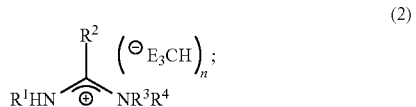

where $R^1$, $R^2$, $R^3$, and $R^4$ are as defined in the tenth aspect, E is O, S or a mixture of O and S, n is a number from 1 to 6 sufficient to balance charge, that is water-soluble and that was prepared by a method comprising: contacting a compound of the tenth aspect with at least one of $CO_2$, $CS_2$ or COS in the presence of water, thereby converting the compound to the salt of formula (2). Optionally, any two of $R^1$, $R^2$, $R^3$ and $R^4$, taken together with the atoms to which they are attached join to form a ring.

The anion $^\ominus E_3CH$ may thus be selected from the group comprising: $^-O_3CH$, $^-O_2SCH$, $^-OS_2CH$, and $^-S_3CH$. It will be apparent that the use of carbon dioxide would provide anion $^-O_3CH$, while the use of $CS_2$ or COS could provide $^-O_3CH$, $^-O_2SCH$, $^-OS_2CH$, and $^-S_3CH$.

The ionic form of formula (2) is an amidinium salt. The ionic form of formula (2) reversibly converts to a compound of formula (1) of the tenth aspect and water when carbon dioxide, $CS_2$ or COS is removed, and the compound of formula (1) of the tenth aspect converts to the ionic form of formula (2) upon contact with carbon dioxide, $CS_2$ or COS and water. Carbon dioxide, $CS_2$ or COS may be removed by contacting the ionic form of formula (2) with a gas that contains substantially no carbon dioxide, $CS_2$ or COS.

In some embodiments of the eleventh aspect, the total number of carbon and/or silicon atoms in all of $R^1$, $R^2$, $R^3$, and $R^4$ is in the range of 10 to 20. In some embodiments of the eleventh aspect, the compound of formula (1) has a log P value in the range of about 3 to about 7. In some embodiments of the eleventh aspect, the log P value is in the range of about 4.5 to about 6.5.

In a twelfth aspect, the invention provides an aqueous solution of the salt of formula (2) of the eleventh aspect that is a single-phase.

In a thirteenth aspect, the invention provides a method of making a salt of formula (2) comprising contacting a compound of formula (1) with carbon dioxide, $CS_2$ or COS in the presence of water, thereby converting the compound to a salt form of formula (2).

In certain embodiments of the thirteenth aspect, the compound of formula (1) and the water are present in at least equimolar amounts. The {number of moles of water} divided by the {number of moles of the compound of formula (1)} may be about 1 should it be desired to consume both the compound of formula (1) and the water without leaving any unreacted amidine or water. In certain embodiments of the thirteenth aspect, the salt of formula (2) precipitates.

In a fourteenth aspect, the invention provides a method of making an aqueous solution of a salt of formula (2) comprising contacting a compound of formula (1) with carbon dioxide, $CS_2$ or COS in the presence of water thereby converting the compound to a salt of formula (2) that is water soluble, wherein sufficient water is provided to solubilize the ionic form of formula (2); and obtaining an aqueous solution of the ionic form of formula (2).

In certain embodiments of the fourteenth aspect, the compound of formula (1) and the water are present in at least equal volumes. The {volume of water} divided by the {volume of the compound of formula (1)} may be ≥ about 1 should it be desired to ensure the dissolution of the ionic form of formula (2), should this be a solid at the temperature at which it is formed.

In certain embodiments of the thirteenth and fourteenth aspects, the contacting a compound of formula (1) with carbon dioxide, $CS_2$ or COS in the presence of water comprises: preparing a two-phase liquid mixture comprising water and a compound of formula (1); and contacting the two-phase liquid mixture with carbon dioxide, $CS_2$ or COS.

In certain embodiments of the thirteenth and fourteenth aspects, the contacting a compound of formula (1) with carbon dioxide, $CS_2$ or COS in the presence of water comprises: preparing an aqueous solution of carbon dioxide, $CS_2$ or COS in water; and mixing the aqueous solution with a compound of formula (1).

In certain embodiments of the thirteenth and fourteenth aspects, the contacting a compound of formula (1) with carbon dioxide, $CS_2$ or COS in the presence of water comprises: dissolving carbon dioxide, $CS_2$ or COS in a compound of formula (1) to provide a non-aqueous liquid; and mixing the non-aqueous liquid with water.

In a fifteenth aspect, the invention provides liquid comprising a compound of formula (1) of the tenth aspect, wherein when an appropriate trigger is applied, the compound in aqueous mixture reversibly switches between two states, a neutral water-immiscible state and an ionic state, that are distinguishable from one another by their polarities; and wherein a first said trigger, for converting the neutral state to the ionic state in an aqueous mixture, is addition of $CO_2$ to the aqueous mixture; a second said trigger, for converting the ionic state to the neutral state in an aqueous solution comprising the compound in its ionic state and dissolved $CO_2$, is depletion of $CO_2$ from the aqueous solution.

In a sixteenth aspect, the invention provides a liquid comprising a compound of formula (1), wherein when an appropriate trigger is applied, the compound in aqueous mixture reversibly switches between two states, a neutral state and a salt state, that are distinguishable from one another by their miscibilities with water; and wherein a first said trigger, for converting the neutral state to the ionic state in an aqueous mixture, is addition of $CO_2$ to the aqueous mixture, and a second said trigger, for converting the ionic state to the neutral state in an aqueous solution comprising the compound in its ionic state and dissolved $CO_2$, is depletion of $CO_2$ from the aqueous solution.

In a seventeenth aspect, the invention provides a liquid comprising a compound of formula (1), wherein when an appropriate trigger is applied, the compound in aqueous mixture reversibly switches between two states, a neutral aqueous-immiscible state at a first partial pressure of $CO_2$ and a salt aqueous-miscible state at a second partial pressure of $CO_2$ that is higher than the first partial pressure of $CO_2$; and wherein a first said trigger, for converting the neutral state to the ionic state in an aqueous mixture, is addition of $CO_2$ to the aqueous mixture, and a second said trigger, for converting the ionic state to the neutral state in an aqueous solution comprising the compound in its ionic state and dissolved $CO_2$, is depletion of $CO_2$ from the aqueous solution.

In embodiments of the fifteenth, sixteenth and seventeenth aspects, depletion of $CO_2$ from the aqueous solution is obtained by: heating the aqueous mixture; placing the aqueous solution under reduced pressure; exposing the aqueous mixture to air; exposing the aqueous mixture to a gas or gases that has insufficient $CO_2$ content to convert the neutral state to the ionic state; flushing the aqueous mixture with a gas or gases that has insufficient $CO_2$ content to convert the neutral state to the ionic state; or a combination thereof.

In an eighteenth aspect, the invention provides a method for separating a selected substance from a mixture, comprising: adding a compound of formula (1) or formula (10) set forth below that is in a liquid state to a mixture of starting material(s) comprising a selected substance that is water-immiscible; allowing the compound to solubilize the selected substance; optionally isolating waste solid(s) from the mixture; contacting the mixture with water and carbon dioxide thereby converting the compound to a salt; allowing the mixture to separate into two distinct phases; separating the two distinct phases to provide an isolated aqueous phase comprising an aqueous solution of the salt and an isolated non-aqueous phase comprising the selected substance; and wherein the selected substance is not reactive with the compound, carbon dioxide, or a combination thereof.

The salt is a compound of formula (2) or formula (20). In certain embodiments of this aspect, the selected substance is a hydrophobic compound. The desired substance may be a solid or a liquid, as long as it is soluble or miscible in the hydrophobic liquid.

In a nineteenth aspect, the invention provides a method for separating a selected liquid from a liquid mixture, comprising: forming a two-phase system by adding a compound of formula (1) or formula (10) set forth below to a liquid mixture comprising a selected liquid that is water-immiscible and at least one further liquid that is immiscible with the compound of formula (1) or formula (10); allowing the liquids to settle into two different phases, a first phase comprising the selected liquid and the compound of formula (1) or formula (10), and a second phase comprising the at least one further liquid that is immiscible with the compound of formula (1) or formula (10); separating the two phases; contacting the first phase with water and carbon dioxide, thereby converting the compound of formula (1) or formula (10) to a salt; allowing the first phase to settle into two distinct phases, one comprising the selected liquid and the other comprising an aqueous solution of the salt; separating the two distinct phases to provide an isolated aqueous phase comprising an aqueous solution of the salt and an isolated non-aqueous phase comprising the selected liquid; and wherein the selected liquid is not reactive with the compound, carbon dioxide or a combination thereof.

The salt is a compound of formula (2) or formula (20) set forth below. In certain embodiments of this aspect, the at least one further liquid that is immiscible with the compound of formula (1) or formula (10) may be water or a non-aqueous liquid. If the at least one further liquid is non-aqueous, it is preferred that this has a higher polarity than the compound of formula (1) or formula (10).

In certain embodiments of the eighteenth and nineteenth aspects, the methods further comprise: removing carbon dioxide from the isolated aqueous phase to reform the compound of formula (1) or formula (10); and isolating the compound. The method of removing carbon dioxide from the isolated aqueous phase may comprise: heating the isolated aqueous phase, contacting the isolated aqueous phase with a nonreactive gas that contains substantially no carbon dioxide; or both heating and contacting with a nonreactive gas that contains substantially no carbon dioxide.

In a twentieth aspect, the invention provides a method for converting a salt to a water-immiscible liquid comprising: preparing an aqueous solution of a salt of formula (2) or formula (20) in which E is O; removing carbon dioxide from the aqueous solution to form a mixture comprising water and a compound of formula (1) or formula (10); allowing the mixture to separate into two distinct phases; and isolating an aqueous phase and a non-aqueous phase comprising the compound of formula (1) or formula (10).

In certain embodiments of the twentieth aspect, the method of removing carbon dioxide comprises: heating the liquid, placing the isolated aqueous phase under reduced pressure, contacting the liquid with a nonreactive gas that contains substantially no carbon dioxide; or both heating and contacting the liquid with a nonreactive gas that contains substantially no carbon dioxide.

In certain embodiments of the eighteenth, nineteenth and twentieth aspects, the carbon dioxide is removed by contacting with a gas that contains substantially no $CO_2$, $CS_2$, or COS.

In another aspect the invention provides a compound of formula (10)

(10)

that is water-immiscible; where $R^5$, $R^6$, and $R^7$ are independently H; a substituted or unsubstituted $C_1$ to $C_{10}$ alkyl group that is linear, branched, or cyclic; a substituted or unsubstituted $C_n Si_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms; wherein, optionally, any combination of $R^5$, $R^6$ and $R^7$, taken together with the atoms to which they are attached join to form a ring; wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, amidine, thioether, alkylcarbonate, phosphine, thioester, or a combination thereof.

In an embodiment of this aspect, the total number of carbon and/or silicon atoms in all of $R^5$, $R^6$, and $R^7$ is in the range of 5 to 12. In an embodiment of this aspect, the compound that has a log P value in the range of about 1.3 to about 3. In other embodiments of this aspect, the log P value is in the range of about 1.5 to about 2.5.

In another aspect, the invention provides a salt of formula (20)

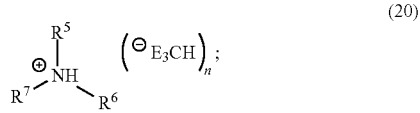

where $R^5$, $R^6$, and $R^7$ are as defined for the compound of formula (10), n is a number from 1 to 6, sufficient to balance the charge of the ammonium cation, and E is O, S or a combination of O and S, wherein the salt is water-soluble and is prepared by a method comprising contacting a compound of formula (10) with at least one of $CO_2$, $CS_2$ or COS in the presence of water, thereby converting the compound to the salt shown as formula (20).

In an embodiment of this aspect, E is oxygen and the salt is prepared by a method comprising contacting a compound of formula (10) with $CO_2$ in the presence of water, thereby converting the compound to the salt shown as formula (20) in which E is oxygen. In certain embodiments of this aspect, the total number of carbon and/or silicon atoms in all of $R^5$, $R^6$, and $R^7$ is in the range of 5 to 12.

In an embodiment of this aspect, the compound has a log P value in the range of about 1.3 to about 3. In other embodiments, the log P value is in the range of about 1.5 to about 2.5.

In another aspect, the invention provides an aqueous solution of the salt of the previous aspect that is single phase.

In yet another aspect, the invention provides a method of making a salt of formula (20) comprising contacting a compound of formula (10) with at least one of $CO_2$, $CS_2$ or COS in the presence of water, thereby converting the compound to a salt of formula (20).

In an embodiment of this aspect, the ratio of number of moles of water to number of moles of the compound of formula (10) is about 1.

In another aspect, the invention provides a method of making an aqueous solution of a salt of formula (20) comprising contacting a compound of formula (10) with at least one of $CO_2$, $CS_2$ or COS in the presence of water thereby converting the compound to a salt of formula (20) that is water soluble, wherein sufficient water is provided to solubilize the salt produced.

In an embodiment of this aspect, the ratio of volume of water to volume of the compound of formula (10) is ≥ about 1. In an embodiment of this aspect, the step of contacting a compound of formula (10) with at least one of $CO_2$, $CS_2$ or COS in the presence of water comprises preparing a two-phase mixture comprising water and a compound of formula (10); and contacting the two-phase mixture with at least one of $CO_2$, $CS_2$ or COS. In other embodiments of this aspect, the step of contacting a compound of formula (10) with at least one of $CO_2$, $CS_2$ or COS in the presence of water comprises preparing a solution of at least one of $CO_2$, $CS_2$ or COS in water; and mixing the solution with a compound of formula (10). In certain embodiments of this aspect, the step of contacting a compound of formula (10) with at least one of $CO_2$, $CS_2$ or COS in the presence of water comprises dissolving at least one of $CO_2$, $CS_2$ or COS in a compound of formula (10) to provide a non-aqueous liquid; and mixing the non-aqueous liquid with water.

In another aspect, the invention provides a method for separating a selected substance from a mixture, comprising adding the compound of formula (10) that is in a liquid state to a mixture comprising a selected substance that is water-immiscible; allowing the compound to solubilize the selected substance; optionally isolating waste solid(s) from the mixture; contacting the mixture with water and $CO_2$ thereby converting the compound to a salt; allowing the mixture to separate into two distinct phases; and separating the two distinct phases to provide an isolated aqueous phase comprising the salt and an isolated non-aqueous phase comprising the selected substance; wherein the selected substance is not reactive with the compound, $CO_2$, or a combination thereof.

An embodiment of this aspect, further comprises removing $CO_2$ from the isolated aqueous phase to reform the water-immiscible compound of formula (10); and isolating the compound.

In an embodiment of this aspect removing $CO_2$ comprises heating the isolated aqueous phase; contacting the isolated aqueous phase with a nonreactive gas that contains substantially no $CO_2$; or both heating and contacting the isolated aqueous phase with a nonreactive gas that contains substantially no $CO_2$.

In another aspect, the invention provides a method for separating a selected liquid from a liquid mixture, comprising forming a two-phase system by adding a compound of formula (10) to a liquid mixture comprising a selected liquid that is water-immiscible and at least one further liquid that is immiscible with the compound of formula (10), wherein a first phase comprises the selected liquid and the compound, and a second phase comprises the at least one further liquid that is immiscible with the compound of formula (10); separating the two phases; contacting the first phase with water and $CO_2$, thereby converting the compound to a salt and forming two distinct phases, one comprising the selected liquid and the other comprising an aqueous solution of the salt; and separating the two distinct phases to provide an isolated aqueous phase comprising the salt and an isolated non-aqueous phase comprising the selected liquid; wherein the selected liquid is not reactive with the compound, $CO_2$ or a combination thereof.

An embodiment of this aspect further comprises removing $CO_2$ from the isolated aqueous phase to reform the compound; and isolating the compound. In certain embodiments, removing $CO_2$ comprises heating the isolated aqueous phase, contacting the isolated aqueous phase with a nonreactive gas that contains substantially no $CO_2$; or both heating and contacting with a nonreactive gas that contains substantially no $CO_2$.

In another aspect, the invention provides a method for converting a salt to a water-immiscible liquid comprising preparing an aqueous solution of a salt of formula (20), removing $CO_2$ from the aqueous solution to form a mixture comprising water and a compound of formula (10); allowing the mixture to separate into two distinct phases; and isolating an aqueous phase and a non-aqueous phase comprising the compound of formula (10). In an embodiment of this aspect, removing $CO_2$ comprises heating the liquid, contacting the liquid with a nonreactive gas that contains substantially no $CO_2$; or both heating and contacting the liquid with a nonreactive gas that contains substantially no $CO_2$. In other embodiments, $CO_2$ is removed by contacting with a gas that contains substantially no $CO_2$, $CS_2$, or COS. In some embodiments of this aspect, the salt of formula (20) precipitates.

In another aspect, the invention provides a method of extracting a hydrophobic material from a solid that is at least partially coated by the hydrophobic material, comprising combining a solid that is at least partially coated by a hydrophobic material and a solvent comprising a compound of formula (1) or a compound of formula (10) to form a mixture of the solid in a homogeneous single-phase liquid, said liquid comprising the compound and the hydrophobic material; separating the solid from the single-phase liquid; combining in any order the single-phase liquid, water, and $CO_2$ to form a two-phase liquid mixture wherein a first phase is hydrophobic and comprises the hydrophobic material and a second phase is aqueous and comprises water and a water-soluble or water-miscible bicarbonate salt of formula (2) or of formula (20).

In an embodiment of this aspect, the hydrophobic material is soluble or miscible in the compound of formula (1) or in the compound of formula (10), but is not soluble nor miscible in a compound of formula (2) or a compound of formula (20).

In certain embodiments of this aspect the hydrophobic material is oil (e.g., motor oil) and the solid is plastic (e.g., polyethylene). In some embodiments, the plastic was previously used to contain the oil.

In another aspect, the invention provides a method of increasing density of polymeric foam, comprising dissolving a polymeric foam in a liquid comprising a compound of formula (1) or a compound of formula (10) to form a solution; combining in any order the solution, water, and $CO_2$ to form a suspension comprising solid polymer and an aqueous liquid comprising bicarbonate salt of formula (2) or bicarbonate salt of formula (20); and separating the suspension to obtain the solid polymer, wherein the solid polymer has increased density relative to the polymeric foam.

In an embodiment of this aspect, the polymeric foam is expanded polystyrene, extruded polystyrene foam, or polystyrene foam packing chips.

In another aspect, the invention provides a method for separating a selected water-immiscible compound from a mixture, comprising adding a liquid comprising a compound of formula (1) or a compound of formula (10) to a first mixture, said first mixture comprising a selected water-immiscible compound that is soluble in the liquid, to form a second mixture; combining in any order the second mixture, water, and $CO_2$ to form a two-phase liquid mixture having a first hydrophobic phase comprising the selected water-immiscible compound and a second aqueous phase comprising bicarbonate salt of formula (2) or bicarbonate salt of formula (20); separating the two phases; wherein the selected water-immiscible compound is not reactive with the liquid, carbon dioxide or a combination thereof.

In an embodiment of this aspect, the selected water-immiscible compound is soluble or miscible in a compound of formula (1) or a compound of formula (10), but is not soluble nor miscible in a compound of formula (2) or a compound of formula (20).

Some embodiments of this aspect, further comprise separating from the second mixture one or more components of the first mixture that is insoluble in the liquid.

In certain embodiments of this aspect, the first mixture is oil-contaminated soil. In other embodiments, the first mixture is a mixture of two or more solids wherein a first solid is soluble in the liquid and a second solid is not. In some embodiments, the first mixture is paper bearing ink wherein the ink is soluble in the liquid.

In another aspect, the invention provides a kit comprising a compound of formula (1) or a compound of formula (10), and optionally instructions for use. In an embodiment of this aspect, the kit is for deinking paper. In another embodiment of this aspect, the kit is for remediating soil. In yet another embodiment, the kit is for increasing the density of a polymeric foam. In another embodiment, the kit is for cleaning polyethylene. In another embodiment, the kit is for use when synthesizing biodiesel. In another embodiment, the kit is for separating a selected substance from a mixture. In another embodiment, the kit is for separating a selected liquid from a liquid mixture. In another embodiment, the kit is for separating a selected liquid from a mixture of two or more solids. In yet another embodiment, the kit is for extracting a hydrophobic material from a solid. In some embodiments, the hydrophobic material is a coating on at least a portion of the solid.

In embodiments of the numerous above aspects, the compound of formula (10) is N-ethylpiperidine, N,N,N-triethylamine, N,N-diethyl-N-methylamine, N,N-dimethyl-N-cyclohexylamine, N,N-dimethyl-N-hexylamine, N,N-diethyl-N-butylamine, N,N-dipropyl-N-methylamine, N,N-diethyl-N-cyclohexylamine, or N-butylpyrrolidine.

In another aspect, the invention provides, a method of extracting a hydrophobic material from a solid that is at least partially coated by the hydrophobic material, comprising: combining a solid that is at least partially coated by a hydrophobic material and a solvent comprising a compound of formula (1) or a compound of formula (10) to form a mixture of the solid in a homogeneous single-phase liquid, said liquid comprising the compound and the hydrophobic material; separating the solid from the single-phase liquid; combining in any order the single-phase liquid, water, and $CO_2$ to form a two-phase liquid mixture wherein a first phase is hydrophobic and comprises the hydrophobic material and a second phase is aqueous and comprises water and a water-soluble or water-miscible bicarbonate salt of formula (2) or of formula (20).

In some embodiments of this aspect, the hydrophobic material is soluble or miscible in a compound of formula (1) or in a compound of formula (10), but is not soluble nor miscible in a compound for formula (2) or in a compound of formula (20). In some embodiments of this aspect, the hydrophobic material is oil (e.g., motor oil) and the solid is plastic (e.g., polyethylene). The plastic may previously have been used to contain the oil.

In another aspect, the invention provides a method of removing gas from polymeric foam, comprising: dissolving a polymeric foam in a switchable hydrophilicity solvent to form a solution; combining in any order the solution, water, and $CO_2$ to form a suspension comprising solid polymer and an aqueous liquid comprising a protonated switchable hydrophilicity solvent; and separating the suspension to obtain the solid polymer.

In some embodiments of this aspect, the switchable hydrophilicity solvent is a compound of formula (1) or (10). In some embodiments of this aspect, the polymeric foam is expanded polystyrene, extruded polystyrene foam, rigid polystyrene containers, high impact thin polystyrene or polystyrene foam packing chips.

In another aspect, the invention provides method of obtaining substantially pure polymer from polymeric foam, comprising: dissolving a polymeric foam in a switchable hydrophilicity solvent to form a solution; combining in any order the solution, water, and $CO_2$ to form a suspension comprising solid polymer and an aqueous liquid comprising a protonated form of the SHS; and separating the suspension to obtain the solid polymer.

In another aspect, the invention provides a method of reducing air or gas content of a polymeric material or a mixture of polymeric materials, comprising: dissolving a polymeric material in a liquid comprising a compound of formula (1) or a compound of formula (10) to form a solution; combining in any order the solution, water, and $CO_2$ to form a suspension comprising solid polymer and an aqueous liquid comprising bicarbonate salt of formula (2) or bicarbonate salt of formula (20); and separating the suspension to obtain the solid polymer. In some embodiments of this aspect, the polymeric product comprises a mixture of polymers.

In another aspect, the invention provides a method for separating a selected water-immiscible compound from a mixture, comprising: adding a liquid comprising a compound of formula (1) or a compound of formula (10) to a first mixture, said first mixture comprising a selected water-immiscible compound that is soluble in the liquid, to form a second mixture; combining in any order the second mixture, water, and $CO_2$ to form a two-phase liquid mixture having a first hydrophobic phase comprising the selected water-immiscible compound and a second aqueous phase comprising bicarbonate salt of formula (2) or bicarbonate salt of formula (20); separating the two phases; wherein the selected water-immiscible compound is not reactive with the liquid, carbon dioxide or a combination thereof.

In some embodiments of this aspect, the selected water-immiscible compound is soluble or miscible in a compound of formula (1) or a compound of formula (10), but is not soluble nor miscible in a compound of formula (2) or a compound of formula (20). In some embodiments of this aspect, the method further comprises separating from the second mixture one or more components of the first mixture that is insoluble in the liquid. In some embodiments of this aspect, the first mixture is: oil-contaminated soil; oil-sands, drilling fines, a mixture of two or more solids wherein a first solid is soluble in the liquid and a second solid is not; or paper bearing ink wherein the ink is soluble in the liquid.

In some embodiments of numerous above aspects, the methods employ one or more compounds of formula (10) selected from N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In another aspect, the invention provides use of a switchable hydrophilicity solvent, wherein when an appropriate trigger is applied, the compound reversibly switches between two states, a neutral water-immiscible state and an ionic water-miscible state; and wherein a first said trigger, for converting the neutral state to the ionic state, is addition of $CO_2$ to an aqueous mixture; and a second said trigger, for converting the ionic state to the neutral state in an aqueous mixture comprising dissolved $CO_2$, is depletion of $CO_2$ from the aqueous mixture.

In some embodiments of this aspect, the switchable hydrophilicity solvent comprises a compound of formula (10). In some embodiments of this aspect, depletion of $CO_2$ from the aqueous mixture is obtained by: heating the aqueous mixture; placing the aqueous mixture under reduced pressure, exposing the aqueous mixture to air; exposing the aqueous mixture to a gas or gases that has insufficient $CO_2$ content to convert the neutral state to the ionic state; flushing the aqueous mixture with a gas or gases that has insufficient $CO_2$ content to convert the neutral state to the ionic state; or a combination thereof.

In another aspect, the invention provides use of a switchable hydrophilicity solvent comprising a compound of formula (10),

(10)

that is water-immiscible; where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms; wherein, optionally, any two of $R^5$, $R^6$ and $R^7$, taken together with the atoms to which they are attached join to form a ring; wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, amidine, thioether, alkylcarbonate, phosphine, thioester, or a combination thereof.

In some embodiments of this aspect, the total number of carbon and/or silicon atoms in all of $R^5$, $R^6$, and $R^7$ is in the range of 5 to 12. In some embodiments of this aspect, the compound of formula (10) has a log P value in the range of about 1.3 to about 3. In some embodiments of this aspect, the compound of formula (10) has a log P value is in the range of about 1.5 to about 2.5.

In another aspect, the invention provides use of a switchable hydrophilicity solvent whose salt form is a compound of formula (20)

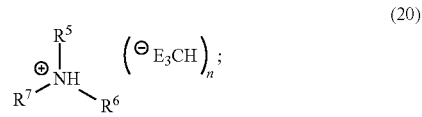

(20)

where $R^5$, $R^6$, and $R^7$ are as defined for the compound of formula (10), n is a number from 1 to 6 sufficient to balance charge of the ammonium cation, and E is O, S or a combination of O and S, wherein the salt is water-soluble and is prepared by a method comprising: contacting a compound of formula (10) with at least one of $CO_2$, $CS_2$ or COS in the presence of water, thereby converting the compound to the salt shown as formula (20).

In some embodiments of this aspect, E is oxygen and the salt is prepared by a method comprising: contacting a compound of formula (10) with $CO_2$ in the presence of water, thereby converting the compound to the salt shown as formula (20) in which E is oxygen. In some embodiments of this aspect, the total number of carbon and/or silicon atoms in all of $R^5$, $R^6$, and $R^7$ is in the range of 5 to 12. In some embodiments of this aspect, the compound of formula (10) has a log P value in the range of about 1.3 to about 3. In some embodiments of this aspect, the log P value is in the range of about 1.5 to about 2.5.

In another aspect, the invention provides use of a switchable hydrophilicity solvent for selective extraction and collection of a selected hydrophobic compound. In some embodiments of this aspect, the switchable hydrophilicity solvent is a compound of formula (1) or a compound of formula (10). In some embodiments of this aspect, the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

In another aspect, the invention provides a kit comprising a switchable hydrophilicity solvent, and optionally instructions for use. In some embodiments of this aspect, the kit includes SHS as a solid bicarbonate salt and the instructions indicate how to switch the salt to its neutral hydrophobic form.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION OF THE INVENTION

Figure 1:
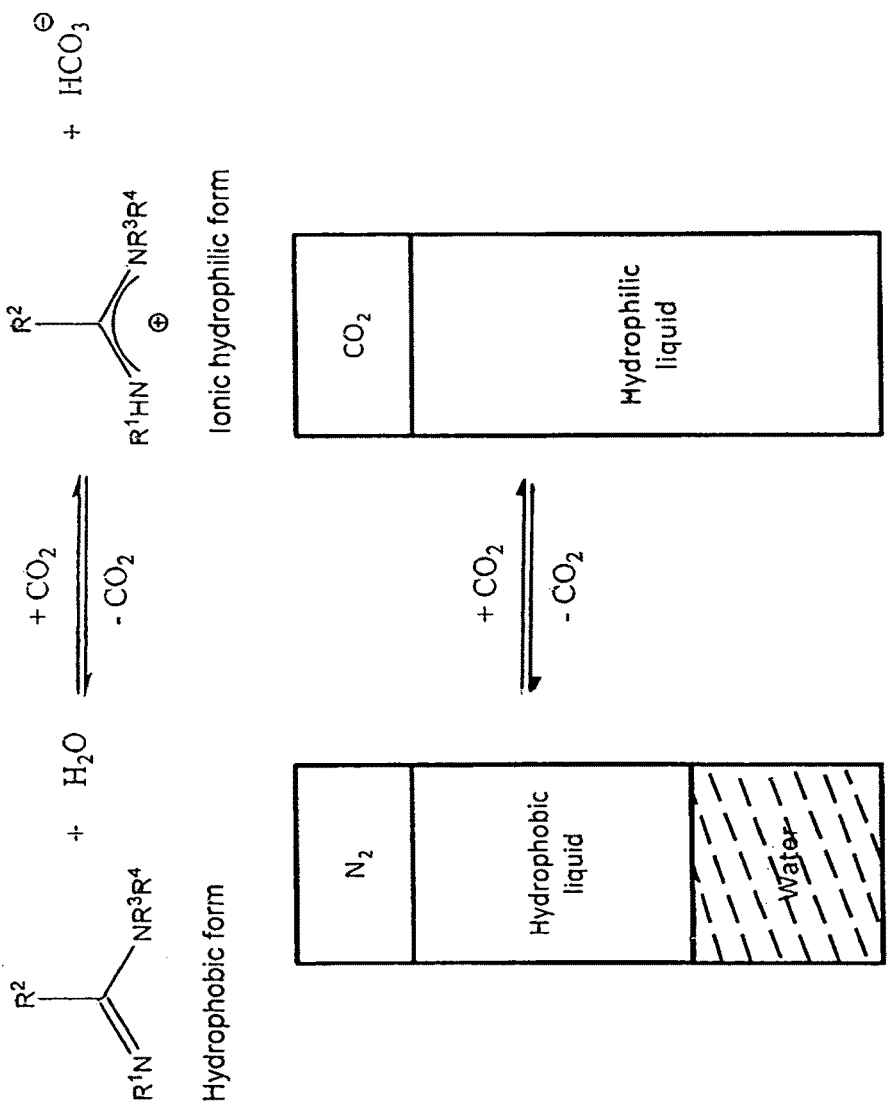
FIG. 1 shows a chemical reaction equation and a schematic of the switching reaction between hydrophobic and hydrophilic forms of an amidine.

Use of conventional solvent provides a volatile liquid with which to solubilise hydrophobic compounds; however, drawbacks of such conventional solvents include their single polarity, toxicity, and that their removal requires costly and energy intensive distillation and its associated environmental impact. The invention described herein includes systems that provide a distillation-free alternative to conventional solvents. Such systems use solvents that can be reversibly converted between two states. In a first state, the system uses an unprotonated neutral compound that is a liquid that is not miscible with water, but rather is hydrophobic and can act as a solvent to dissolve hydrophobic compounds. In a second state, the system uses a protonated form of the compound of the first state, which protonated compound is hydrophilic and is miscible with water. Such systems provide controlled switchability between the two states such that they can be generated over and over again.

That is, solvents that reversibly convert from a hydrophobic water-immiscible form to a hydrophilic water-miscible form upon contact with water and a trigger such as contact with $CO_2$, are described. The hydrophilic form is readily converted back to the hydrophobic form and water. Such solvents are referred to herein as switchable hydrophilicity solvents. The following terms are used in this description.

Definitions

As used herein, "switchable hydrophilicity solvent" refers to a compound that, in the presence of water or other aqueous solution, exists in an aqueous-immiscible state at a first partial pressure of $CO_2$ and exists in an aqueous-miscible state at a second partial pressure of $CO_2$ that is higher than the first partial pressure of $CO_2$. That is, this term refers to a solvent that, in the presence of water or other aqueous solution, can be changed from an aqueous-immiscible liquid state to an aqueous-miscible state by raising the partial pressure of $CO_2$, and that can be changed from an aqueous-miscible state to an aqueous-immiscible state by lowering the partial pressure of $CO_2$. This term also applies to the case wherein COS, $CS_2$, or a mixture of any or all of $CO_2$, COS, or $CS_2$, is employed in place of the $CO_2$ recited above.

It should of course be understood that for the purposes of this application the terms "water-immiscible" and "aqueous-immiscible" are used interchangeably and the terms "water-miscible" and "aqueous-miscible" are used interchangeably.

As used herein, "aliphatic" refers to hydrocarbon moieties that are linear, branched or cyclic, may be alkyl, alkenyl or alkynyl, and may be substituted or unsubstituted. "Aryl" means a moiety including a substituted or unsubstituted aromatic ring, including heteroaryl moieties and moieties with more than one conjugated aromatic ring; optionally it may also include one or more non-aromatic ring. "$C_5$ to $C_{10}$ Aryl" means a moiety including a substituted or unsubstituted aromatic ring having from 5 to 10 carbon atoms in one or more conjugated aromatic rings. Examples of aryl moieties include phenyl, biphenyl, naphthyl and xylyl.

As used herein, "heteroaryl" means a moiety including a substituted or unsubstituted aromatic ring or ring system having from 3 to 20, or 4 to 10 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, bipyridyl, indolyl, thienyl, and quinolinyl.

As used herein, "substituted" means having one or more substituent moieties whose presence does not interfere with the desired reaction. Examples of substituents include alkyl, alkenyl, alkynyl, aryl, aryl-halide, heteroaryl, cyclyl (non-aromatic ring), Si(alkyl)$_3$, Si(alkoxy)$_3$, halo, alkoxyl, amino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof. Preferable substituents are alkyl, aryl, heteroaryl, and ether. In some embodiments, substituents include an amine or an amidine moiety. It is noted that aryl halides are acceptable substituents. Alkyl halides are known to be quite reactive, and are acceptable so long as they do not interfere with the desired reaction.

As used herein, "short chain aliphatic" or "lower aliphatic" refers to $C_1$ to $C_4$ aliphatic. "Long chain aliphatic" or "higher aliphatic" refers to $C_5$ to $C_{10}$ aliphatic.

As used herein, the term "unsubstituted" refers to any open valence of an atom being occupied by hydrogen. Also, if an occupant of an open valence position on an atom is not specified then it is hydrogen.

The term "switched" means that the physical properties and, in particular, the hydrophilicity have been modified. "Switchable" means able to be converted from a first state with a first set of physical properties, e.g., a hydrophobic state, to a second state with a second set of physical properties, e.g., a hydrophilic state, or vice-versa from the second state to the first state. A "trigger" is a change of conditions (e.g., introduction or removal of a gas, change in temperature) that causes a change in the physical properties, e.g. hydrophilicity. The term "reversible" means that the reaction can proceed in either direction (backward or forward) depending on the reaction conditions.

As used herein, "carbonated water" means a solution of water in which carbon dioxide has been dissolved. "Carbon dioxide saturated water" means a solution of water in which carbon dioxide is dissolved to the maximum extent at that temperature and pressure.

As used herein, "a gas that has substantially no carbon dioxide" means that the gas has insufficient carbon dioxide content to interfere with the removal of carbon dioxide from the solution. For some applications, air may be a gas that has substantially no carbon dioxide. Untreated air may be successfully employed, i.e., air in which the carbon dioxide content is unaltered; this would provide a cost saving. For instance, air may be a gas that has substantially no carbon dioxide because in some circumstances, the approximately 0.04% by volume of carbon dioxide present in air is insufficient to maintain a compound in a switched form, such that air can be a trigger used to remove carbon dioxide from a solution and cause switching. Similarly, "a gas that has substantially no carbon dioxide, $CS_2$ or COS" has insufficient carbon dioxide, $CS_2$ or COS content to interfere with the removal of carbon dioxide, $CS_2$ or COS from the solution.

As used herein, "coating" or "coated" refers to placement of, for example, a hydrophobic material, on or proximal to a solid's surface, but does not exclude impregnation of the solid where it is able to absorb all or part of the hydrophobic material.

As used herein, the term "contaminant" refers to one or more compounds that is intended to be removed from a mixture and is not intended to imply that the contaminant has no value. For example, oil, which has significant value, may conveniently be called a contaminant when describing oil sands.

As used herein, the term "substantially pure" refers to having an approximately homogeneous or uniform composition. A substantially pure sample has a preponderance of one component and any impurity is present only in trace amounts.

As used herein, the term "migration" refers to movement of a substance from a first location to a second location. For illustrative purposes, in a non-limiting example, a substance may be present in a first layer of a two-layer system and then, due to a change in conditions, may migrate to the second layer of the system.

As used herein, "amidine" (see compound of formula (1) below) refers to a molecule with a structure $R^1N=C(R^2)-NR^3R^4$, where $R^1$ through $R^4$ are hydrogen or aliphatic or aryl or heteroaryl as discussed below. The ionic form (salt) of an amidine (see compound of formula (2) below) is termed an "amidinium salt". The bicarbonate salt of an amidine (see compound of formula (3) below) is termed an "amidinium bicarbonate". It should be noted that amidine as used herein also includes the structure $R^1N=CH-NR^3R^4$ (i.e., $R^2$ is replaced by H), where $R^1$, $R^3$, and $R^4$ are as discussed above.

As used herein, "amine" (see compound of formula (10) below) refers to a molecule with a structure $NR^5R^6R^7$, where $R^5$ through $R^7$ are hydrogen or aliphatic or aryl or heteroaryl as discussed below. The ionic form (salt) of an amine (see compound of formula (20) below) is termed an "ammonium salt". The bicarbonate salt of an amine (see compound of formula (30) below) is termed an "ammonium bicarbonate".

As used herein, "in the presence of water" means that at least a small amount of water is present. In many cases the ratio of switchable hydrophilicity solvent to water (by volume) for the formation of the hydrophilic protonated form of the solvent can be any ratio, e.g. 1:1, 1:2, 1:3, 1:4, etc.

"Ionic" means containing or involving or occurring in the form of positively or negatively charged ions, i.e., charged moieties. "Neutral" as used herein means that there is no net charge. "Ionic salt", "salt" and "ionic form" as used herein are used interchangeably to refer to compounds formed from positively and negatively charged ions, these terms do not imply a physical state (i.e., liquid, gas or solid). For purposes of this disclosure, "ionic liquids" are salts that are liquid below 100° C.; such liquids are typically nonvolatile, polar and viscous. "Nonionic liquids" means liquids that do not consist primarily of molecules with formal charges such as ions. Nonionic liquids are available in a wide range of polarities and may be polar or nonpolar; they are typically more volatile and less viscous than ionic liquids.

As used herein, a "polar" molecule is a molecule in which some separation occurs of the centres of positive and negative charge. Polar solvents are typically characterized by a dipole moment. Ionic liquids are considered to be polar solvents, even though a dipole may not be present, because they behave in the same manner as polar liquids in terms of their ability to solubilize polar solutes, their miscibility with other polar liquids, and their effect on solvatochromic dyes. A polar solvent is generally better than a nonpolar (or less polar) solvent at dissolving polar or charged molecules.

As used herein, "Nonpolar" means having weak solvating power of polar or charged molecules. Nonpolar solvents are associated with either having little or no separation of charge, so that no positive or negative poles are formed, or having a small dipole moment. A nonpolar solvent is generally better than a polar solvent at dissolving nonpolar, waxy, or oily molecules.

As used herein, "hydrophobicity" is a property of a compound or molecules of a compound leading it to be repelled from a mass of water. Hydrophobic molecules are usually nonpolar have little or no hydrogen bonding ability. Such molecules are thus compatible with other neutral and nonpolar molecules. The degree of hydrophobic character of the compound, or hydrophobicity, can be quantified by a log P value. The log P is the logarithm of the 1-octanol (lipid)-water partition coefficient, P, of a compound. This partition coefficient seeks to determine the ratio of solubilities of a molecule in a lipid environment and a hydrophilic aqueous environment. The lipid-water partition coefficient is the equilibrium constant calculated as the ratio of the concentration of the compound in the lipid phase divided by the concentration of the molecule in the aqueous phase, when those two phases are in contact with each other and when the compound has been allowed enough time to reach its equilibrium concentrations in both phases. P is sometimes referred to as $K_{ow}$, and log P is sometimes referred to as log $K_{ow}$.

Partition coefficients can be experimentally determined using n-octanol as a model of the lipid phase and an aqueous phosphate buffer at pH 7.4 as a model of the water phase. Because the partition coefficient is a ratio, it is dimensionless. The partition coefficient is an additive property of a molecule, because each functional group helps determine the hydrophobic or hydrophilic character of the molecule. If the log P value is small, the molecule will be miscible with water such that the water and molecule will form a single-phase in most proportions. If the log P value is large, the compound will be immiscible with water such that a two-phase liquid mixture will be formed with the water and molecule present as separate layers in most proportions.

It is also possible to theoretically calculate log P values because of the additive nature of the partition coefficient arising from the individual functional groups of a molecule. A number of computer programs are available for calculating log P values. The log P values described herein are predicted using ALOGPS 2.1 software, which calculates the log P value for a given molecule using nine different algorithms and then averages the values. This computational method is fully described by Tetko I. V. and Tanchuk V. Y. in *J. Chem. Inf. Comput. Sci.*, 2002, 42, 1136-1145 and in *J. Comput. Aid. Mol. Des.*, 2005, 19, 453-463, both of which are incorporated herein by reference.

In contrast to hydrophobicity, "hydrophilicity" is a property of a molecule allowing it to transiently bond with water through hydrogen bonding. Hydrophilic molecules are usually polar. Such molecules may thus be compatible with other polar molecules.

As used herein, "insoluble" refers to a solid in a specified liquid that is not well solubilized but rather forms a heterogeneous mixture. It is recognized that the solubility of an "insoluble" solid in a specified liquid might not be zero but rather it would be smaller than that which is useful in practice. The use of the terms "soluble", "insoluble", "solubility" and the like are not intended to imply that only a solid/liquid mixture is intended. For example, a statement that a compound is soluble in water is not meant to imply that the compound must be a solid; the possibility that the compound may be a liquid is not excluded.

As used herein, "misciblility" is a property of two liquids that when mixed provide a homogeneous solution. In contrast, "immiscibility" is a property of two liquids that when mixed provide a heterogeneous mixture, for instance having two distinct phases.

As used herein, "immiscible" means unable to merge into a single-phase. Thus two liquids are described as "immiscible" if they form two phases when combined in a proportion. This is not meant to imply that combinations of the two liquids will be two-phase mixtures in all proportions or under all conditions. The immiscibility of two liquids can be detected if two phases are present, for example via visual inspection. The two phases may be present as two layers of liquid, or as droplets of one phase distributed in the other phase. The use of the terms "immiscible", "miscible", "miscibility" and the like are not intended to imply that only a liquid/liquid mixture is intended. For example, a statement that a compound is miscible with water is not meant to imply that the compound must be a liquid; the possibility that the compound may be a solid is not excluded.

"NMR" means Nuclear Magnetic Resonance. "IR spectroscopy" means infrared spectroscopy. "UV spectroscopy" means ultraviolet spectroscopy.

As used herein, "wet diethyl ether" means diethyl ether whose container has been opened to the atmosphere such that water from the air surrounding the container has entered the solvent.

Embodiments

The invention provides systems that include switchable hydrophilicity solvents. In an embodiment of the invention, the switchable hydrophilicity solvents is a compound of formula (1) below,

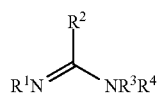

(1)

that is immiscible with water;

where $R^1$, $R^2$, $R^3$, and $R^4$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or a substituted or unsubstituted heteroaryl group having 4 to 10 atoms in the aromatic ring;

wherein a substituent is independently alkyl, alkenyl, alkynyl, aryl, aryl halide, heteroaryl, non-aromatic rings, Si(alkyl)$_3$, Si(alkoxy)$_3$, halo, alkoxy, amino, ester, amide, amidine, thioether, alkylcarbonate, phosphine, thioester, or a combination thereof.

Representative example of compounds of formula (1) include the following compounds:

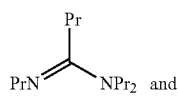

(PA)

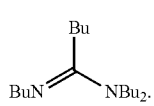

(BA)

The above two molecules have been synthesized, characterized and tested (see Example 4). They were both determined to be switchable hydrophilicity solvents since they were reversibly switched between water-miscible and water-immiscible states as described herein. Notably, amidines that are water-immiscible are rare. Commercially available amidines have been tested and were determined to be unsuitable as switchable hydrophilicity solvents since they were water-miscible in their neutral (unprotonated) forms. These compounds were: 1,8-diazabicyclo-[5.4.0]-undec-7-ene (DBU) and Me$_2$N—C(=N-hexyl)Me.

A mixture of amidines may be used instead of a single amidine.

In another embodiment of the invention, the switchable hydrophilicity solvents is a compound of formula (10) below,

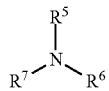

(10)

that is immiscible with water;

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 atoms in the aromatic ring;

wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, amidine, thioether, alkylcarbonate, phosphine, thioester, or a combination thereof.

The amine can be primary, secondary or tertiary. In a preferred embodiment, the amine is tertiary.

A mixture of amines may be used instead of a single amine. In one embodiment, the mixture of amines comprises a greater portion of tertiary amine(s) and a lesser portion of primary or secondary amine(s). Mixtures of compounds of formula (1), mixtures of compounds of formula (10), and mixtures of a compound of formula (1) and a compound of formula (10) are also suitable as switchable hydrophilicity solvents. In certain embodiments, mixtures of two or more switchable hydrophilicity solvents are used to modulate viscosity of the solvent. By matching viscosities of the SHS and a liquid for extraction and isolation, it is possible to minimize formation of emulsion.

In certain embodiments of formulas (1), any combination of $R^1$, $R^2$, $R^3$ and $R^4$, taken together with the atoms to which they are attached, are joined to form a cyclic ring. In some embodiments, they form a heterocyclic ring. In some embodiments, the ring has 4 to 8 ring atoms.

In certain embodiments of formulas (10), any combination of $R^5$, $R^6$, and $R^7$, taken together with the nitrogen atom to which they are attached, are joined to form a heterocyclic ring. In some embodiments, the ring has 4 to 8 ring atoms.

The compound of formula (1) described above is an amidine. The compound of formula (10) described above is an amine. In the liquid state, a compound of formula (1) that is immiscible with water is hydrophobic in nature and can function as a solvent for water-immiscible and water-insoluble substances. In the liquid state, a compound of formula (10) that is immiscible with water is hydrophobic in nature and can function as a solvent for water-immiscible and water-insoluble substances.

The water-immiscible compound of formula (1) or of formula (10) can advantageously be converted from its hydrophobic form to a second hydrophilic form when subjected, in the presence of water, with a gas that liberates hydrogen ions. The second hydrophilic form is a salt that forms a single-phase ionic solution with water. More particularly, the ionic form is an amidinium salt or an ammonium salt. The aqueous ionic solution can be switched back when an appropriate trigger is applied, to form (or re-form) a two-phase hydrophobic liquid and water mixture. In this situation the trigger causes deprotonation of the amidinium or ammonium ion's nitrogen atom. Deprotonation is caused by expulsion from the solution of a gas that liberates hydrogen ions. Accordingly aspects of the invention provide a solvent that can either mix with or separate from water in a controllable manner.

As used herein, gases that liberate hydrogen ions in an aqueous environment, (which are referred to herein as "gases that liberate hydrogen ions") fall into two groups. Group (i) includes gases that liberate hydrogen ions in the presence of a base, for example, HCN and HCl (water may be present, but is not required). Group (ii) includes gases that when dissolved in water react with water to liberate hydrogen ions, for example, $CO_2$, $NO_2$, $SO_2$, $SO_3$, $CS_2$ and COS. For example, $CO_2$ in water will produce $HCO_3^-$ (bicarbonate ion) and $CO_3^{2-}$ (carbonate ion) and hydrogen counterions, with bicarbonate being the predominant species at pH 7. One skilled in the art will recognize that the gases of group (ii) will liberate a smaller amount of hydrogen ions in water in the absence of a base, and will liberate a larger amount of hydrogen ions in water in the presence of a base.

Preferred gases that liberate hydrogen ions are those wherein the salt switches to its hydrophobic liquid (amidine or amine) form when the same gas is expelled from the environment. $CO_2$ is particularly preferred. Hydrogen ions produced from dissolving $CO_2$ in water protonate the amidine (or amine). In such solution, the counterion for the amidinium ion (or ammonium ion) is predominantly bicarbonate. However, some carbonate ions are also present in solution and the possibility that, for example, two amidinium molecules (or two ammonium molecules), each with a single positive charge, associate with a carbonate counterion is not excluded. When $CO_2$ is expelled from the solution, the amidinium cation (or ammonium cation) is deprotonated and thus is converted to its hydrophobic amidine (or amine) form.

Of group (ii) gases that liberate hydrogen ions, $CS_2$ and COS are reasonably expected to behave similarly to $CO_2$ such that they are reversibly switchable. However, they are not preferred because their use in conjunction with water and an amidine or amine could cause the formation of highly toxic $H_2S$. In some embodiments, $CS_2$ is not preferred for the switching of certain amidines because of an undesired reaction in which $CS_2$ cleaves the amidine. This undesired cleavage does not happen to amines and it does not happen to some amidines. In some embodiments of the invention, alternative gases that liberate hydrogen ions are used instead of $CO_2$, or in combination with $CO_2$, or in combination with each other. Alternative gases that liberate hydrogen ions (e.g., HCl, $SO_2$, HCN) are less preferred because of the added costs of supplying them and recapturing them, if recapturing is appropriate. However, in some applications one or more such alternative gases may be readily available and therefore add little to no extra cost. Many such gases, or the acids generated from their interaction with water, are likely to be so acidic that the reverse reaction, i.e., converting the amidinium or ammonium salt to the amidine or amine hydrophobic liquid, may not proceed to completion as easily as the corresponding reaction with $CO_2$. Group (i) gases HCN and HCl are less preferred triggers because of their toxicity and because reversibility would likely require a strong base.

The present invention provides a salt of formula (2) where $R^1$, $R^2$, $R^3$, and $R^4$ are as defined for the compound of formula (1), n is a number from 1 to 6 sufficient to balance the overall charge of the amidinium cation, and E is O, S or a mixture of O and S,

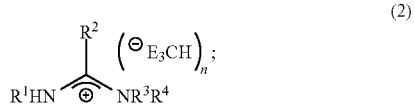

(2)

that is water-soluble and that was prepared by a method comprising:

contacting a water-immiscible compound of formula (1) with carbon dioxide, $CS_2$ or COS in the presence of water, thereby converting the compound to the salt of formula (2).

The contacting of a water-immiscible compound of formula (1) with carbon dioxide, $CS_2$ or COS in the presence of water may comprise:

preparing a two-phase liquid mixture comprising water and a water-immiscible compound of formula (1); and contacting the two-phase liquid mixture with carbon dioxide, $CS_2$ or COS.

Alternatively, the contacting of a water-immiscible compound of formula (1) with carbon dioxide, $CS_2$ or COS in the presence of water may comprise:

preparing an aqueous solution of carbon dioxide, $CS_2$ or COS in water; and mixing the aqueous solution with a water-immiscible compound of formula (1).

Alternatively, the contacting of a water-immiscible compound of formula (1) with carbon dioxide, $CS_2$ or COS in the presence of water may comprise:

dissolving carbon dioxide, $CS_2$ or COS in a water-immiscible compound of formula (1) to provide a non-aqueous liquid; and mixing the non-aqueous liquid with water.

The salt of formula (2) is water-soluble and can therefore form a single-phase aqueous solution when dissolved in water. This is an extremely advantageous property which can be used to separate a compound of formula (1) from a substance which is miscible with the compound of formula (1), but is water-immiscible, by converting the compound of formula (1) to a water-soluble salt of formula (2).

Furthermore, the water-soluble salt of formula (2) may be converted back into a water-immiscible compound of formula (1) by removal of a gas that liberates hydrogen ions from the solution. This is advantageous because it allows the re-use of the compound of formula (1) that is water-immiscible.

The present invention provides a salt of formula (20) where $R^5$, $R^6$, and $R^7$ are as defined for the compound of formula (10), n is a number from 1 to 6 sufficient to balance the overall charge of the ammonium cation, and E is O, S or a mixture of O and S,

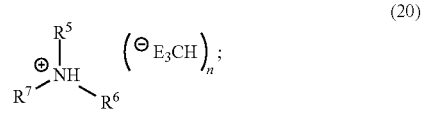

(20)

that is water-soluble and that was prepared by a method comprising:

contacting a water-immiscible compound of formula (10) with carbon dioxide, $CS_2$ or COS in the presence of water, thereby converting the compound to the salt of formula (20).

The contacting of a water-immiscible compound of formula (10) with carbon dioxide, $CS_2$ or COS in the presence of water may comprise:

preparing a two-phase mixture comprising water and a water-immiscible compound of formula (10); and contacting the two-phase mixture with carbon dioxide, $CS_2$ or COS.

Alternatively, the contacting of a water-immiscible compound of formula (10) with carbon dioxide, $CS_2$ or COS in the presence of water may comprise:

preparing an aqueous solution of carbon dioxide, CS₂ or COS in water; and mixing the aqueous solution with a water-immiscible compound of formula (10).

Alternatively, the contacting of a water-immiscible compound of formula (10) with carbon dioxide, CS₂ or COS in the presence of water may comprise:

dissolving carbon dioxide, CS₂ or COS in a water-immiscible compound of formula (10) to provide a non-aqueous liquid; and mixing the non-aqueous liquid with water.

The salt of formula (20) is water-soluble and can therefore form a single-phase aqueous solution when dissolved in water. This is an extremely advantageous property which can be used to separate a compound of formula (10) from a substance which is miscible with the compound of formula (10), but is water-immiscible, by converting the compound of formula (10) to a water-soluble salt of formula (20).

Furthermore, the water-soluble salt of formula (20) may be converted back into a water-immiscible compound of formula (10) by removal of a gas that liberates hydrogen ions from the solution. This is advantageous because it allows the re-use of the compound of formula (10) that is water-immiscible.

Formulas (10), (20), (3) and (30) show an anion as $^-E_3CH$, where E may be O, S or both O and S. That is, when all three E are O, the anion is bicarbonate (also called hydrogen carbonate). When two E are O and one E is S, the anion is hydrogen thiocarbonate. When E is one O and two S, the anion is hydrogen dithiocarbonate. When all three E are S, the anion is hydrogen trithiocarbonate. It is to be understood that anions present in the system are expected also to include $[CE_3]^{2-}$, known as carbonate, thiocarbonate, dithiocarbonate, or trithiocarbonate. In most embodiments, where the pH is close to neutral, the concentration of $[CE_3]^{2-}$ will be small compared to the concentration of $^-E_3CH$. However, in some embodiments, at higher pH, the concentration of $[CE_3]^{2-}$ will approach or even surpass the concentration of $^-E_3CH$. For example, such a situation may arise in applications requiring higher pH. For another example, such a situation may arise during a stage in the removal of $CE_2$ when the removal of $CE_2$ is incomplete but the pH has risen sufficiently during the process to allow the concentration of $[CE_3]^{2-}$ to approach or even surpass the concentration of $^-E_3CH$.

A gas that liberates hydrogen ions may be expelled from a solution by simple heating or by placing the solution under reduced pressure (e.g., less than 1 atm). Alternatively and conveniently, a nonreactive gas may be employed to expel a gas that liberates hydrogen ions from a solution. Such a nonreactive gas is referred to herein as a "flushing gas". This shifts the equilibrium from ionic form to hydrophobic liquid (amidine or amine). In certain situations, especially if speed is desired, both a flushing gas and heat can be employed.

Preferred flushing gases are N₂, air, air that has had its carbon dioxide component substantially removed, and argon. Less preferred nonreactive (flushing gases) are those gases that are costly to supply and/or to recapture, where appropriate. However, in some applications one or more flushing gases may be readily available and therefore add little to no extra cost. In certain cases, flushing gases are less preferred because of their toxicity, e.g., carbon monoxide.

Air is a particularly preferred choice as a flushing gas according to the invention, where the CO₂ level of the air (today commonly 380 ppm) is sufficiently low that an ionic form (amidinium or ammonium salt) is not maintained in its salt form. Untreated air is preferred because it is both inexpensive and environmentally sound. In some situations, however, it may be desirable to employ air that has had its carbon dioxide component substantially removed as a flushing gas. By reducing the amount of CO₂ in the flushing gas, potentially less salt/amidine or amine may be employed. Alternatively, some environments may have air with a high CO₂ content, and such flushing gas would not achieve complete switching of ionic form to hydrophobic amidine or amine form. Thus, it may be desirable to treat such air to remove enough of its CO₂ for use as a trigger.

In a preferred embodiment, in the presence of water and carbon dioxide, an amidine compound of formula (1) that is water-immiscible, converts to an amidinium bicarbonate, depicted as a salt of formula (3) below,

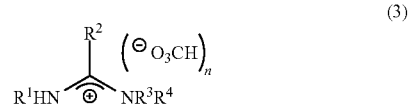

(3)

where n, $R^1$, $R^2$, $R^3$, and $R^4$ are as defined above.

The salt which can be an amidinium bicarbonate compound may be a solid or a liquid. It will be apparent that at least a molar equivalent of water is required to react with the carbon dioxide to provide the carbonic acid to protonate the nitrogen atom of the imino group of the amidine to form the amidinium cation. In embodiments where a certain amidinium bicarbonate of formula (3) is a solid and not a liquid, more than a molar equivalent of water (relative to the amidine compound of formula (1) that is water-immiscible) is added to ensure the complete dissolution of the amidinium bicarbonate in the aqueous phase after switching. In some embodiments, the amount of water is 1 or more volume equivalents relative to the amidine. In certain embodiments, isolation of amidinium bicarbonate as a solid is possible by controlling the amount of water present.

Such amidines are more stable in acidic aqueous solution because hydroxide attack on the amidinium cation is the primary mechanism for hydrolytic degradation. Consequently, there should be no significant degradation of the amidinium salt when it is dissolved in carbon dioxide saturated water (due to the presence of carbonic acid). When the salt is converted back to the amidine compound of formula (1) that is water-immiscible, it separates out of the water. Therefore degradation of the compound of formula (1) by hydrolysis should not be significant. This means that the amidines disclosed herein should be suitable for industrial application, and repeated re-use, as a result of their stability.

In a preferred embodiment, in the presence of water and carbon dioxide, an amine compound of formula (10) that is water-immiscible, converts to an ammonium bicarbonate, depicted as a salt of formula (30) below,

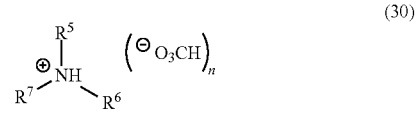

(30)

where n, $R^1$, $R^2$, $R^3$, and $R^4$ are as defined above.

The ionic form which can be an ammonium bicarbonate compound may be a solid or a liquid. It will be apparent that at least a molar equivalent of water is required to react with the carbon dioxide to provide the carbonic acid to protonate the nitrogen atom of the amine to form the ammonium cation.

In embodiments where a certain ammonium bicarbonate of formula (30) is a solid and not a liquid, more than a molar equivalent of water (relative to the amine compound of formula (10) that is water-immiscible) is added to ensure the complete dissolution of the ammonium bicarbonate in the aqueous phase after switching. In some embodiments, the amount of water is 1 or more volume equivalents relative to the amine. In certain embodiments, isolation of ammonium bicarbonate as a solid is possible by controlling the amount of water present.

In certain embodiments of compounds of formula (10) at least one of $R^5$, $R^6$ or $R^7$ are substituted by an amino moiety (as discussed above). Such compounds are diamines, triamines, or polyamines. In some embodiments, polyamines are preferred since less contamination by residual solvent occurs in the hydrophobic material that is isolated when the switchable hydrophilic solvent is converted to its hydrophilic form (see Example 2). Although not wishing to be bound by theory, the inventors provide the following description of why polyamines lead to less contamination.

In some embodiments, it may be advantageous to use a switchable hydrophilicity solvent that has more than one basic nitrogen atom, such as a diamine or a triamine. There are at least two potential advantages of such a compound over one having only one basic nitrogen atom. First, a compound with more than one basic nitrogen is likely to be a heavier compound and therefore less volatile. It will therefore likely be less odorous (e.g., smelly) than a compound with only one basic nitrogen. Second, a compound with more than one basic nitrogen would be expected to be more readily separated by carbonated water from a hydrophobic liquid such as an oil. More ready separation is expected for the following reason. Complete protonation of an amine switchable hydrophilicity solvent by carbonated water is not likely because carbonic acid is not a sufficiently strong acid. Therefore a switchable solvent having only one basic nitrogen atom, when it is incompletely protonated by the carbonated water, will exist primarily as a monocation and in small amounts as its neutral form. The neutral form is likely to partition primarily into a hydrophobic phase rather than into carbonated water. Thus if the carbonated water only protonates the amine to the extent of, say, 96%, then at least 4% of the amine remains in the hydrophobic phase rather than in the carbonated water phase. In contrast, a switchable solvent that is, for example, a diamine, when incompletely protonated by carbonic acid, would consist primarily as a dication with small amounts of the monocation and very small amounts of the neutral form. Thus, if it is assumed that only the neutral form would have a tendency to partition into the hydrophobic phase, the amount of switchable solvent remaining in the organic phase would be very small and on the order of the amount of the diamine that remains uncharged. This amount must mathematically be smaller than the amount of neutral species in the case of an amine containing only a single basic nitrogen.

The optimum log P range expected to give the desired phase behaviour (meaning that the solvent is miscible with carbonated water and not miscible with non-carbonated water) has already been mentioned for monoamines). The inventors expect that the appropriate range of log P for compounds having more than one basic nitrogen atom, such as diamines, may be different and possibly somewhat higher than the appropriate range for monoamines, although the ranges may overlap. A higher range for, for example, diamines is expected because the diamines, when fully protonated, will have two hydrophilic cationic sites containing hydrogen-bonding acidic protons and two hydrophilic bicarbonate counter anions. In contrast, a monoamine, when fully protonated, will have only one hydrophilic cationic site and only one bicarbonate anion. Therefore a higher log P, indicating that the compound would be too hydrophobic to serve as a monoamine switchable hydrophilicity solvent, might be acceptable in a switchable hydrophilicity solvent having more than one basic nitrogen atom because the extra hydrophobicity indicated by the high log Kow would be overcome by the extra hydrophilicity of the extra cationic sites and extra bicarbonate anions.

The following examples are offered: $Me_2NCH_2CH_2CH_2CH_2NMe_2$ is predicted to have a log P of 0.9 and is not a switchable hydrophilicity solvent because it is miscible with water even in the absence of $CO_2$. It is therefore too hydrophilic. $Et_2NCH_2CH_2CH_2CH_2NEt_2$ and $EtPrNCH_2CH_2CH_2CH_2NEtPr$ are predicted to have log P values of 2.5 and 3.4, respectively, and are switchable hydrophilicity solvents because they are immiscible with water in the absence of $CO_2$ and miscible with water in the presence of $CO_2$. Therefore, they have log P values within the correct range for diamines to function as switchable hydrophilicity solvents. $Pr_2NCH_2CH_2CH_2CH_2NPr_2$ is predicted to have a log P of 4.4 and is not a switchable hydrophilicity solvent because it is immiscible with water even in the presence of $CO_2$. It is therefore too hydrophobic. The inventors note that the log P for a diamine must be greater than 0.9 and less than 4.4, and note that 2.5 and 3.4 are acceptable values. The exact range that is preferred for a diamine has not yet been identified by the testing of further examples. The log P values that are appropriate for triamines may be even greater than those considered acceptable for diamines.

In some embodiments, addition of a small amount of piperazine further increases the rate of conversion of a switchable hydrophilicity solvent to its ionic form. In studies conducted by the inventors using a compound of formula (10), specifically dimethylcyclohexylamine (5 mL), and water (5 mL) at room temperature and a $CO_2$ flow rate of 100 mL/min through a fritted tube, it was found that in the absence of piperazine, the time of $CO_2$ bubbling for phase merge was 35 minutes. In the presence of an absorption activator, specifically 10 wt % piperazine, the time of $CO_2$ bubbling to phase merge was only 20 minutes. Although not experimentally shown, the inventors expect that piperazine would have a similar absorption activating effect for compounds of formula (1). A similar improvement in $CO_2$ capture for aqueous solutions of tertiary amines was reported by Dubois (Chem. Eng. Tech. 32(5): 710 (2009)).

In some embodiments of the invention, the switchable hydrophilicity solvent in its neutral form may be lipophilic or oleophilic, for example, dimethylcyclohexylamine, $Et_2NCH_2CH_2CH_2CH_2NEt_2$.

An aspect of this invention provides a method of extracting a selected substance from a starting material or starting materials that comprise the selected substance. In some embodiments, the selected substance is water-immiscible. For instance the starting material may be a solid impregnated with the selected substance or a liquid mixture of the selected substance and a hydrophilic liquid or the selected solid substance containing undesired gas bubbles. The selected substance may be a hydrophobic liquid such as an oil or a hydrophobic solid such as a wax or polymer. The selected substance should be miscible or soluble in a switchable hydrophilicity solvent, which may be water-immiscible compound of formula (1) or formula (10), and thereby be readily separable from the rest of the starting material.

For instance, if a selected substance is a hydrophobic liquid, a miscible mixture can be formed by mixing the selected substance with a switchable hydrophilicity solvent, which may be a water-immiscible compound of formula (1) or formula (10), which water-immiscible compound acts as a hydrophobic liquid solvent. If the selected substance is a hydrophobic solid, it can be dissolved in a water-immiscible compound of formula (1) or formula (10), which water-immiscible compound acts as a hydrophobic liquid solvent.

The miscible mixture or solution of the selected substance and switchable hydrophilicity solvent is a single-phase liquid. Thus, it is possible to isolate the miscible mixture or solution from any further components of the starting material or starting materials which are not soluble or miscible with the single-phase liquid. For instance, if such a further component is a solid (e.g., residual soy bean flakes where the soy oil has been extracted/removed), it can be separated from the single-phase liquid by filtration. If such a further component is a liquid which is immiscible with the single-phase liquid, this component could be separated by decanting. If such a further component is a gas, this component could be liberated during the dissolution of the selected substance or with subsequent heating or otherwise degassing (e.g., reduced pressure conditions) of the solution.

A selected substance, such as a solute, which is soluble in a switchable hydrophilicity solvent, which may be a water-immiscible compound of formula (1) or formula (10), or a liquid, which is miscible with a water-immiscible compound of formula (1) (or formula (10)), can be separated from a compound of formula (1) (or formula (10)) by switching the hydrophilicity of the compound of formula (1) (or formula (10)). When a water-immiscible compound of formula (1) (or formula (10)) has been converted into its ionic form (salt) of formula (2) (or formula (20)), the selected substance, such as the solute or liquid may separate as a distinct phase. This can occur if the selected substance is immiscible with or insoluble in either an ionic liquid of formula (2) (or formula (20)) or an aqueous solution of a salt of formula (2) (or formula (20)). After switching, two phases can be formed, an aqueous phase comprising an ionic form (salt) of formula (2) (or formula (20)) and a non-aqueous phase comprising a selected substance. The phase of selected substance, such as a solid precipitate or hydrophilic liquid layer, may then be separated from the aqueous solution of the hydrophilic second form of the solvent by, for example, decanting, filtering, and centrifuging. Similarly, if the amount of water is controlled so that the ionic compound of formula (2) (or formula (20)) forms as a solid and the selected substance is a liquid, then the liquid phase of the selected substance can be separated from the solid ionic compound of formula (2) (or formula (20)) by filtration.

This method of extracting a selected substance is particularly effective if the selected substance is hydrophobic and miscible/soluble in a switchable hydrophilicity solvent, which may be a water-immiscible amidine compound of formula (1) or a water-immiscible amine compound of formula (10). An example of this embodiment of the invention is presented in FIG. 3B which shows extraction of soybean oil from soybean flakes using a water-immiscible amidine of formula (1) as solvent (see also Example 2A-C). This figure shows that when soy flakes are mixed with amidine ("B"), soybean oil ("oil") is extracted from the flakes and the two liquids are miscible ("B+oil"). The soybean flakes may then be separated from the B+oil mixture by filtration. As discussed in working example 2, soybean oil ("oil") was experimentally shown to be miscible with a water-immiscible liquid amidine of formula (1). Further, soybean oil was isolated from the B+oil mixture by switching the solvent from its hydrophobic form to its amidinium bicarbonate hydrophilic form (see FIG. 3b). Specifically, as discussed in Example 2, the mixture was contacted with carbon dioxide in the presence of water to switch the liquid amidine to its water soluble amidinium bicarbonate form (hydrophilic form) as shown by formula (3). The contacting was carried out by treating a miscible mixture with carbonated water or adding water to form a two-phase mixture of an aqueous phase and a non-aqueous phase comprising a liquid amidine of formula (1) that is water-immiscible and soy oil and then actively exposing the two-phase mixture to carbon dioxide. The soy oil then formed a non-aqueous layer and the amidinium bicarbonate formed an aqueous layer comprising a solution of the salt in water ("[BH][$O_2$COH] in water"). The non-aqueous and aqueous layers are immiscible and formed two distinct phases, which can then be separated by, e.g., decantation. Once separated, the non-aqueous and aqueous layers provide an isolated non-aqueous phase comprising soybean oil and an isolated aqueous phase comprising the hydrophilic amidinium bicarbonate form of the switchable solvent. In this way, the solvent is separated from the soy oil without distillation.

The amidinium bicarbonate salt of formula (3) in the aqueous phase was switched back to its hydrophobic form (amidine compound of formula (1) that is water-immiscible) by removal of carbon dioxide from the solution e.g., by heating or degassing. The amidine compound of formula (1) that is water-immiscible separated from the water to provide a non-aqueous layer separate from the aqueous phase. The amidine compound of formula (1) that is water-immiscible was then separated from the water by, e.g., decanting to isolate a non-aqueous phase comprising the hydrophobic amidine, which can then be reused to treat more soy flakes.

Thus switchable hydrophilicity solvents provide a low energy, low pollution alternative to current technology for extractions such as soybean oil extraction. Currently, the solvent used for soy bean oil extraction from soy bean flakes is hexane. The use of hexane as a solvent is undesirable because of its neurotoxicity and high volatility even at room temperature. The high volatility of hexane, or any other solvent that is to be removed by distillation, is necessary for the distillation but is most regrettable in terms of health and environmental impact. Volatile solvents are easily partially lost by evaporation, and thus contribute to smog formation, ground-level ozone formation, high flammability, high insurance costs, and worker inhalation hazards such as toxicity, neurotoxicity, carcinogenicity, mutagenicity, teratogenicity, and short and long term damage to vital organs. The identification of switchable hydrophilicity solvents, which can be removed without distillation, means that volatile solvents can be avoided.

Another example that is similar to extraction of soybean oil from soybean flakes is extraction of algae oil from algae. Algae oil can be used in biodiesel production. Switchable hydrophilicity solvents are useful for dissolving algae oil. The liquid mixture, which includes switchable solvent and dissolved oil, is then readily separated from solid algae by. e.g., decantation or filtration. The oil can then be separated from the switchable solvent by placing the liquid mixture in contacting with carbon dioxide in the presence of water. Under these conditions the solvent switches to its water miscible form and migrates to a hydrophilic liquid layer that is distinct from the hydrophobic layer, which includes the algae oil. The algae oil is then readily separable from the hydrophilic layer by. e.g., decantation.

During off shore drilling a large amount of waste is generated in the form of drilling fines. Drilling fines are typically mixtures of rock, dispersants, wetting agents, emulsifiers, lubricants and drilling fluid and are usually cleaned/treated before disposal. In the case of offshore drilling sites, this contaminated rock is currently transported from the offshore oilrig to the mainland before treatment. Such samples generally contain 10-40 wt % impurities (e.g., drilling fluid(s), oil, etc.) when they are initially brought onto the oilrig. In order for the mass to be disposed of it must contain less than 5% impurity. If the waste could be treated on the oilrig it and disposed over board it would greatly reduce the environmental impact of the process. As described in Example 9, switchable hydrophilicity solvent technology could clean (i.e., remove contaminant(s)) the contaminated rock samples and recover contaminants for reuse in other applications. As described in Example 10, studies using a conventional solvent, specifically hexanes, to remove contaminants showed the obtained sample of contaminated rock obtained from drilling fines to be 19 wt % fluids. When a sample of this contaminated rock was mixed with a switchable hydrophilicity solvent of formula (10), specifically N,N-dimethylcyclohexyl-amine, filtered, and dried under an air flow it resulted in a dry sand/rock mixture. An oily fluid was then isolated from the filtrate. When the amine/fluid mixture was combined with the aqueous layer and bubbled with $CO_2$, a clear, yellow oil-like layer was obtained. This layer corresponded to a value of 17 wt % of the original contaminated rock sample. Accordingly, the SHS was able to effectively remove and recapture the contaminant (drilling fluid, oil, etc.) from the sample of drilling fines.

The invention further provides a method for maintaining or disrupting miscibility of two liquids where one of the two liquids is a reversible switchable hydrophilicity solvent comprising an aqueous solution of a salt of formula (2) or formula (20). When a trigger is applied, the switchable hydrophilicity solvent's properties change to become hydrophobic (a water-immiscible compound of formula (1) or formula (10)) and the newly-immiscible liquids separate. An embodiment of the invention provides a switchable hydrophilicity solvent that can be reversibly and readily switched between immiscible hydrophobic liquid (compound of formula (1) or formula (10) that is water-immiscible) and water and an aqueous solution of the hydrophilic form of the solvent (salt of formula (3) or formula (30)) by applying or removing $CO_2$.

Referring to FIG. 1, a chemical scheme and schematic drawing are shown for a switchable hydrophilicity solvent system of amidine and water. Such a system is further discussed in relation to N,N,N'-tripropylbutyramidine ($R^1=R^2=R^3=R^4=$propyl) and N,N,N'-tributylpentanamidine ($R^1=R^2=R^3=R^4=$butyl), which are examples of water-immiscible compounds of formula (1), in the Examples below. The chemical reaction equation shows a substituted amidine (hydrophobic form) and water on the left hand side and amidinium bicarbonate (ionic and thus hydrophilic form) on the right hand side. This reaction can be reversed, as indicated. The schematic also shows the same reaction wherein the two-phase mixture of the compound of formula (1) that is water-immiscible (amidine) and water is on the left side under a blanket of $N_2$. The aqueous solution of the salt comprising amidinium bicarbonate is shown on the right side under a blanket of carbon dioxide.

Figure 2:
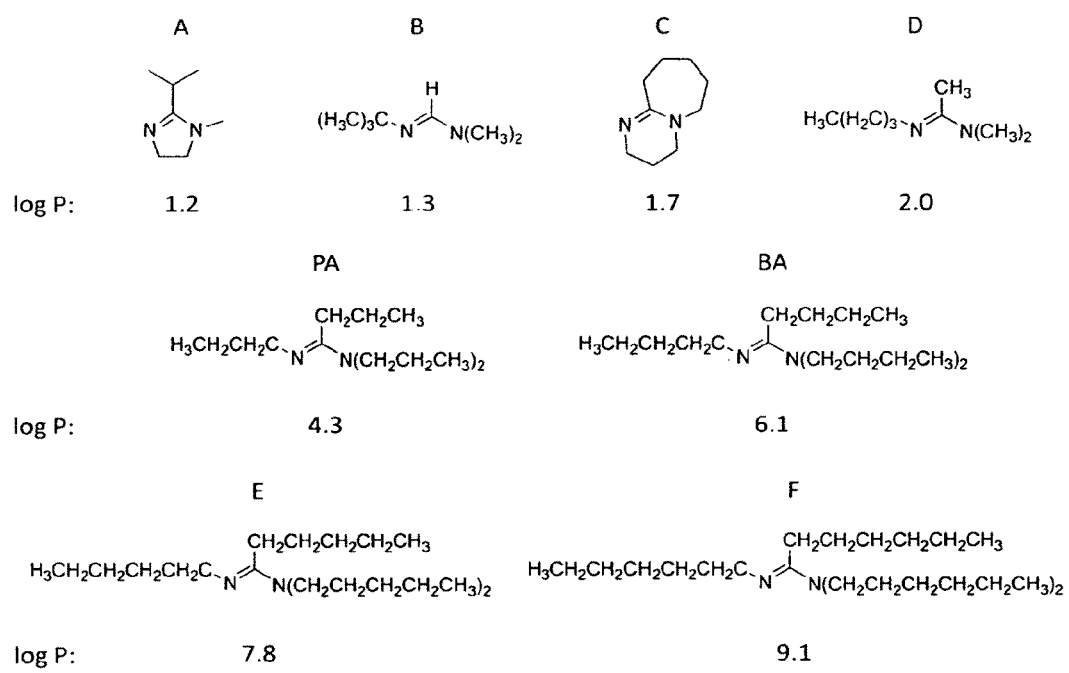
FIG. 2 presents the hydrophilicity/hydrophobicity of various liquids by indicating calculated log P values for each liquid.

Referring to FIG. 2, the hydrophilicity/hydrophobicity of various amidine and guanidine liquids is provided by indicating calculated log P values for each liquid.

Figure 3A:
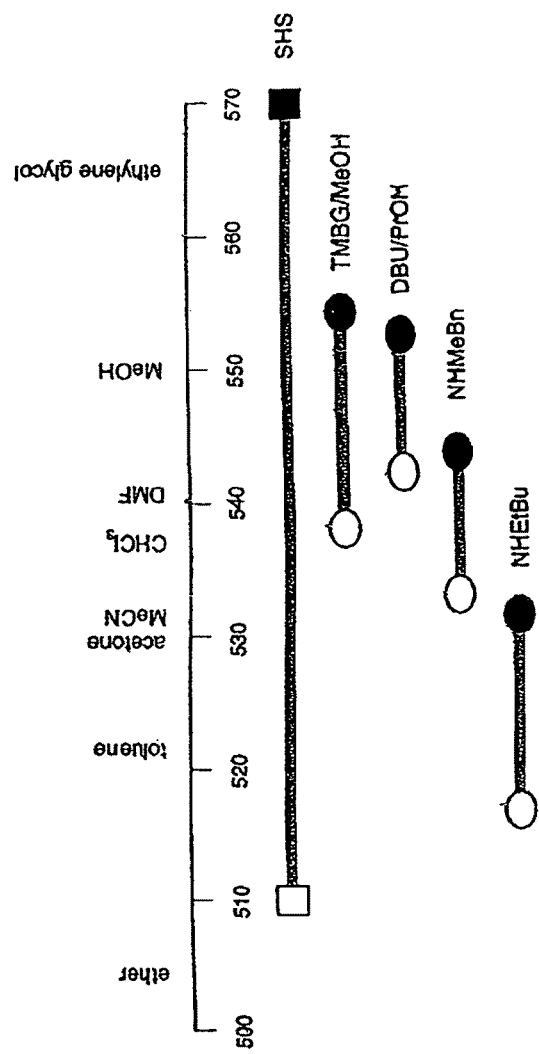
FIG. 3A presents a comparison of the polarity of N,N,N'-tributylpentanamidine, shown as an open square, and an aqueous solution of N,N,N'-tributylpentanamidinium bicarbonate, shown as a black square, as measured by the change in the maximum wavelength of absorption in nm of the solvatochromic dye Nile Red, with other solvents and switchable systems. The conventional solvents listed along the horizontal wavelength axis are diethyl ether (ether), toluene, acetone, acetonitrile (MeCN), chloroform ($CHCl_3$), dimethyl formamide (DMF), methanol (MeOH) and ethylene glycol. The change in maximum wavelength of absorption of BA/water is compared to 1,8-diazabicyclo[5.4.0]undec-7-ene/propanol (DBU/PrOH); 1,1,3,3-tetramethyl-2-butylguanidine/methanol (TMBG/MeOH); N,N-methylbenzylamine (NHMeBn); and N,N-ethylbenzylamine (NHEtBn).

Referring to FIG. 3A a comparison of the polarity of water-saturated N,N,N'-tributylpentanamidine, shown as an open square, and an aqueous solution of N,N,N'-tributylpentanamidinium bicarbonate, shown as a black square, as measured by the maximum wavelength of absorption in nm of the solvatochromatic dye Nile Red, with other solvents and switchable solvents is presented.

Figure 3B:
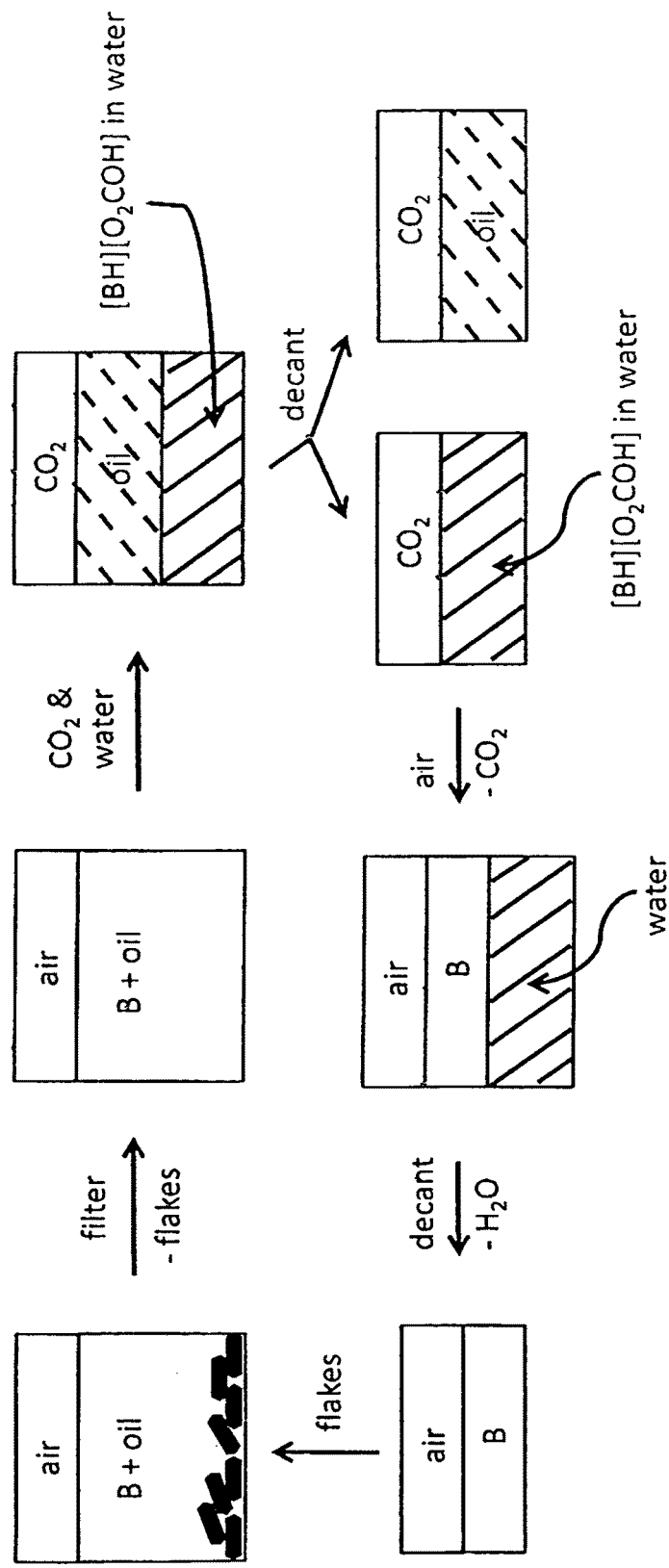
FIG. 3B presents the method of separating a selected liquid from a mixture comprising the selected liquid ("oil"), as disclosed herein. In this embodiment the selected liquid is soy oil and the mixture comprising the selected liquid includes soy flakes.

Referring to FIG. 3B, a method of separating a selected liquid ("oil") from a mixture comprising a selected liquid as disclosed herein is presented. In this embodiment the selected liquid is soy oil and the mixture comprising the selected liquid includes soy flakes.

Figure 4A:
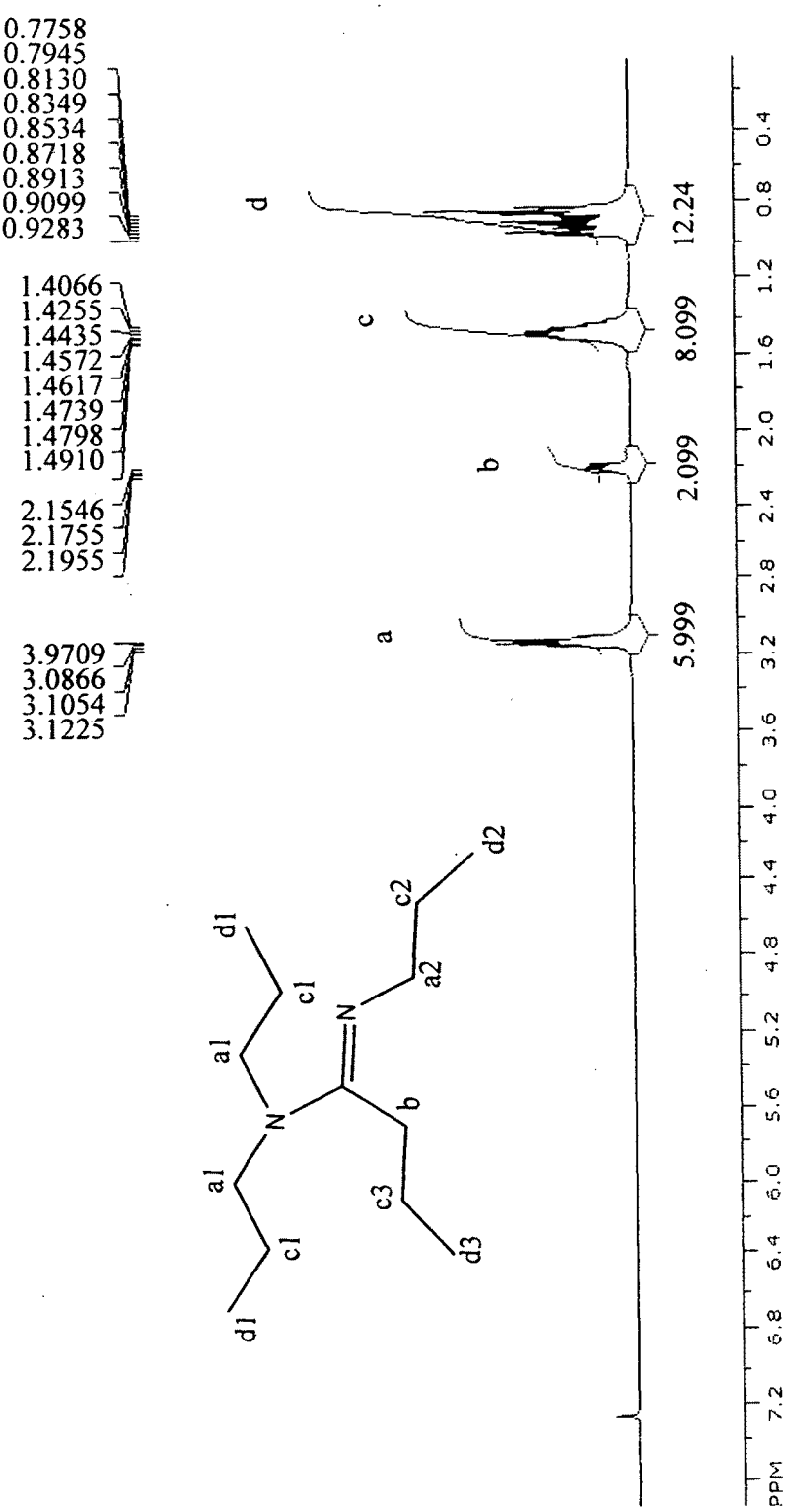
FIG. 4A shows a $^1H$ NMR spectrum of N,N,N'-tripropylbutyramidine in $CDCl_3$ at 400 MHz.
Figure 4B:
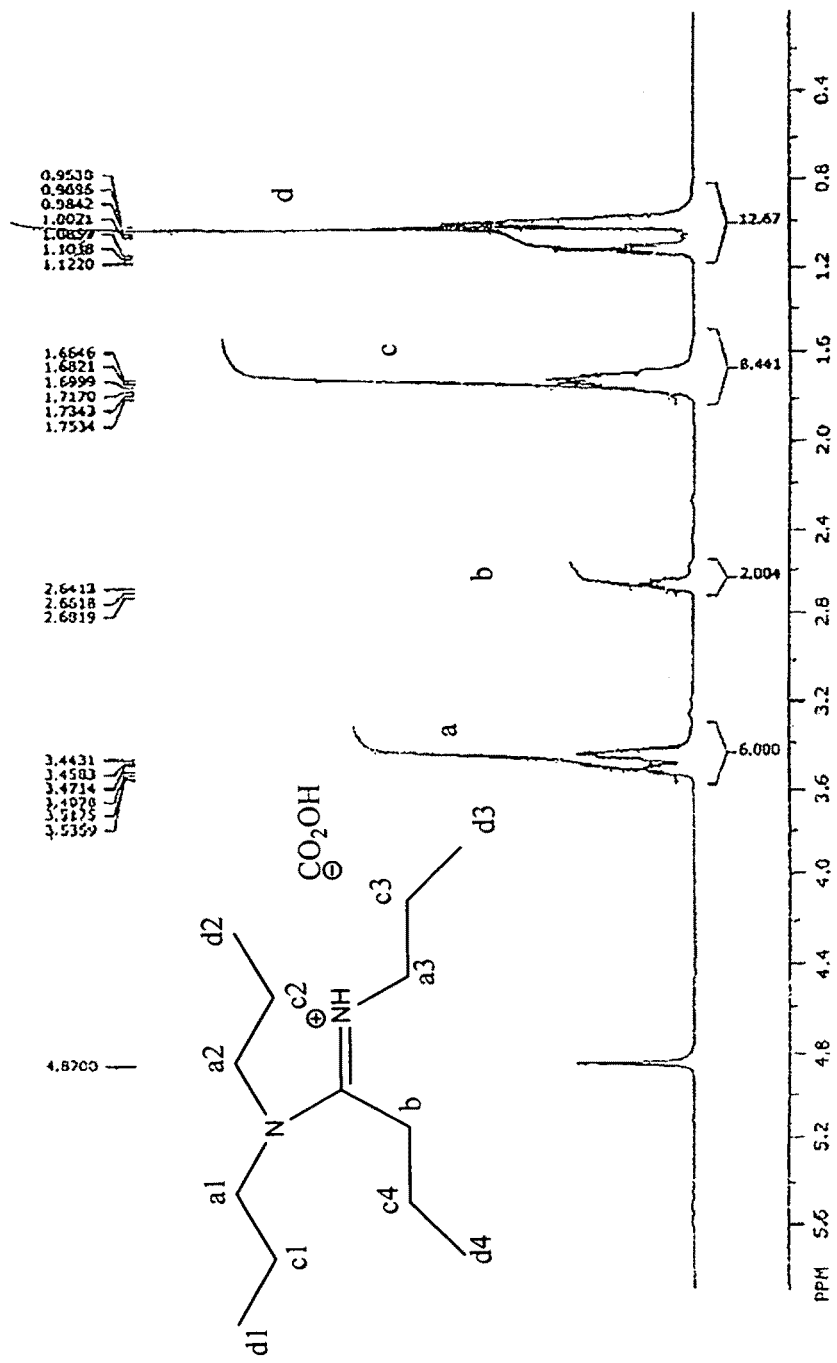
FIG. 4B shows a $^1H$ NMR spectrum of N,N,N'-tripropylbutyramidinium bicarbonate in $D_2O$ at 400 MHz.

Referring to FIGS. 4A and 4B, $^1$H NMR spectra of N,N,N'-tripropylbutyramidine and N,N,N'-tripropylbutyramidinium bicarbonate in $D_2O$ at 400 MHz are shown.

Figure 5A:
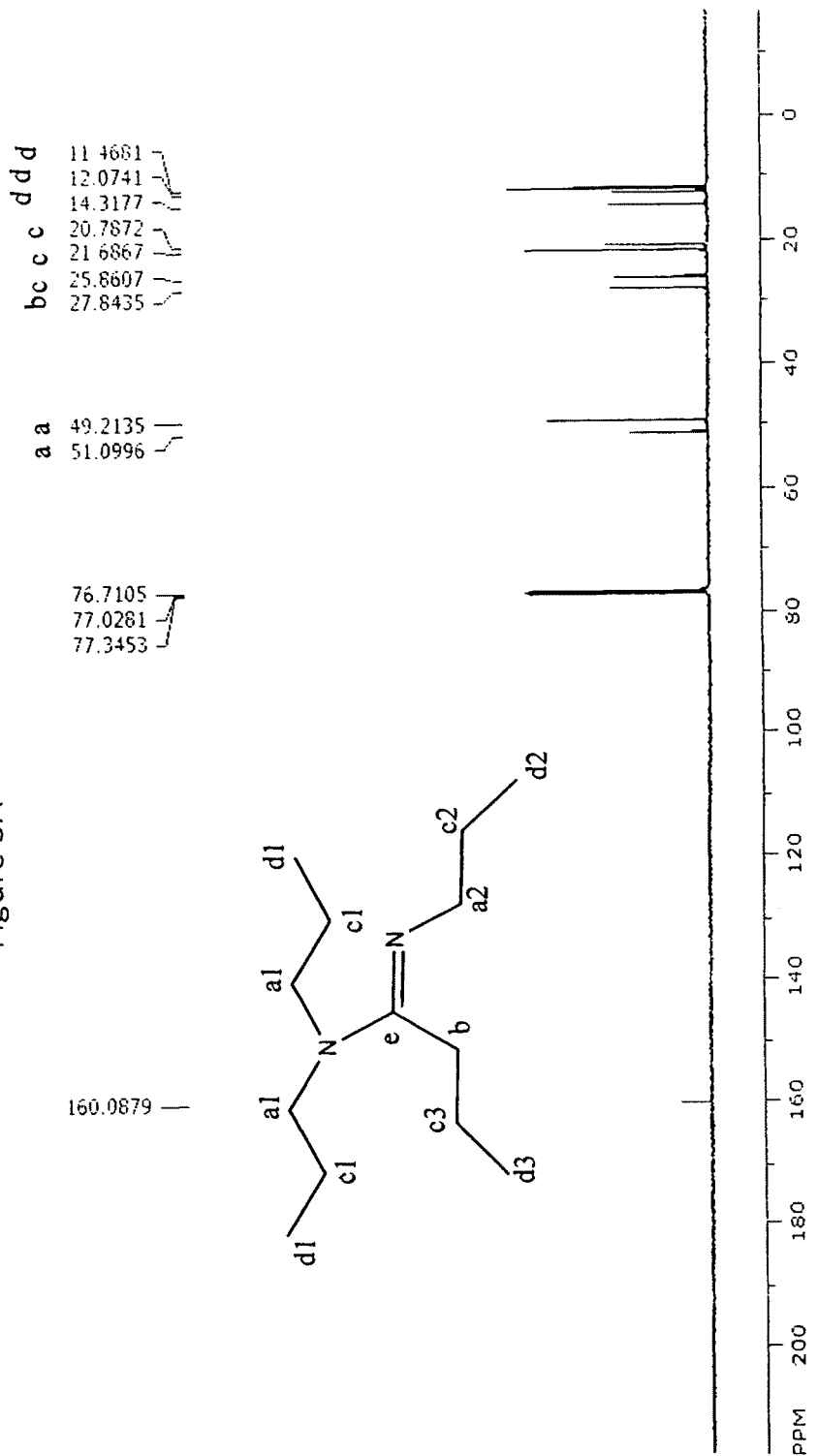
FIG. 5A shows a $^{13}C$ NMR spectrum of N,N,N'-tripropylbutyramidine in $CDCl_3$ at 100 MHz.
Figure 5B:
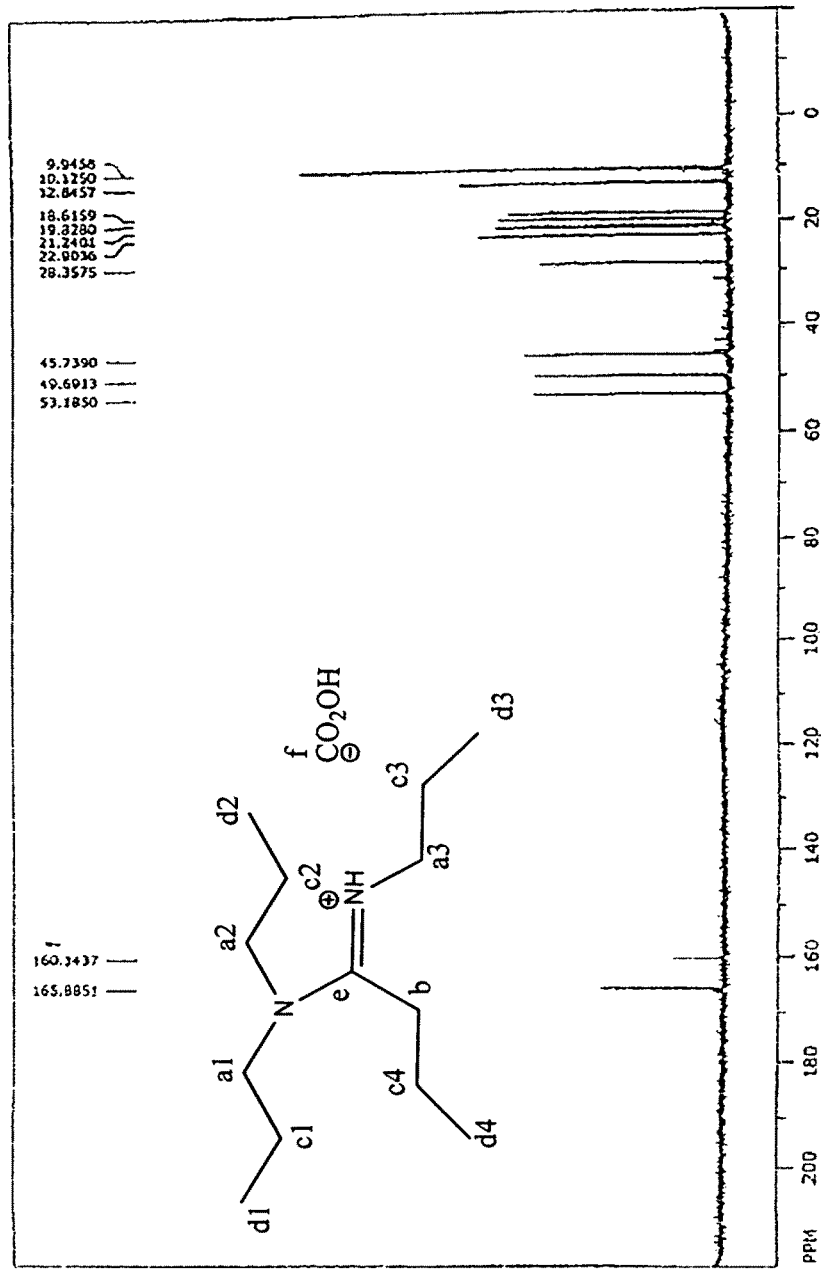
FIG. 5B shows a $^{13}C$ NMR spectrum of N,N,N'-tripropylbutyramidinium bicarbonate in $D_2O$ at 100 MHz.

Referring to FIGS. 5A and 5B, $^{13}$C NMR spectra of N,N,N'-tripropylbutyramidine and N,N,N'-tripropylbutyramidinium bicarbonate in $D_2O$ at 100 MHz are shown.

Figure 6A:
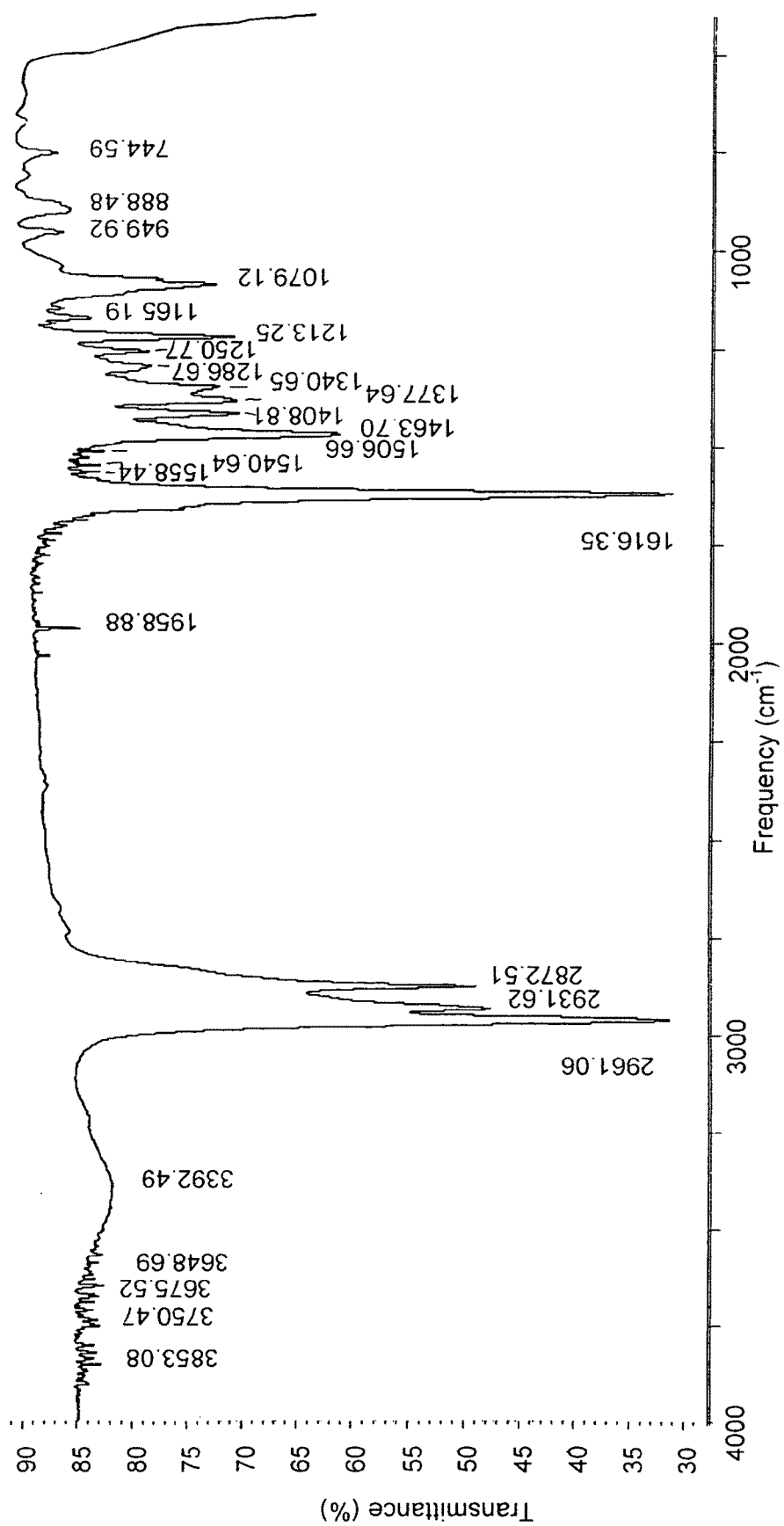
FIG. 6A shows an IR spectrum of N,N,N'-tripropylbutyramidine between potassium bromide plates.
Figure 6B:
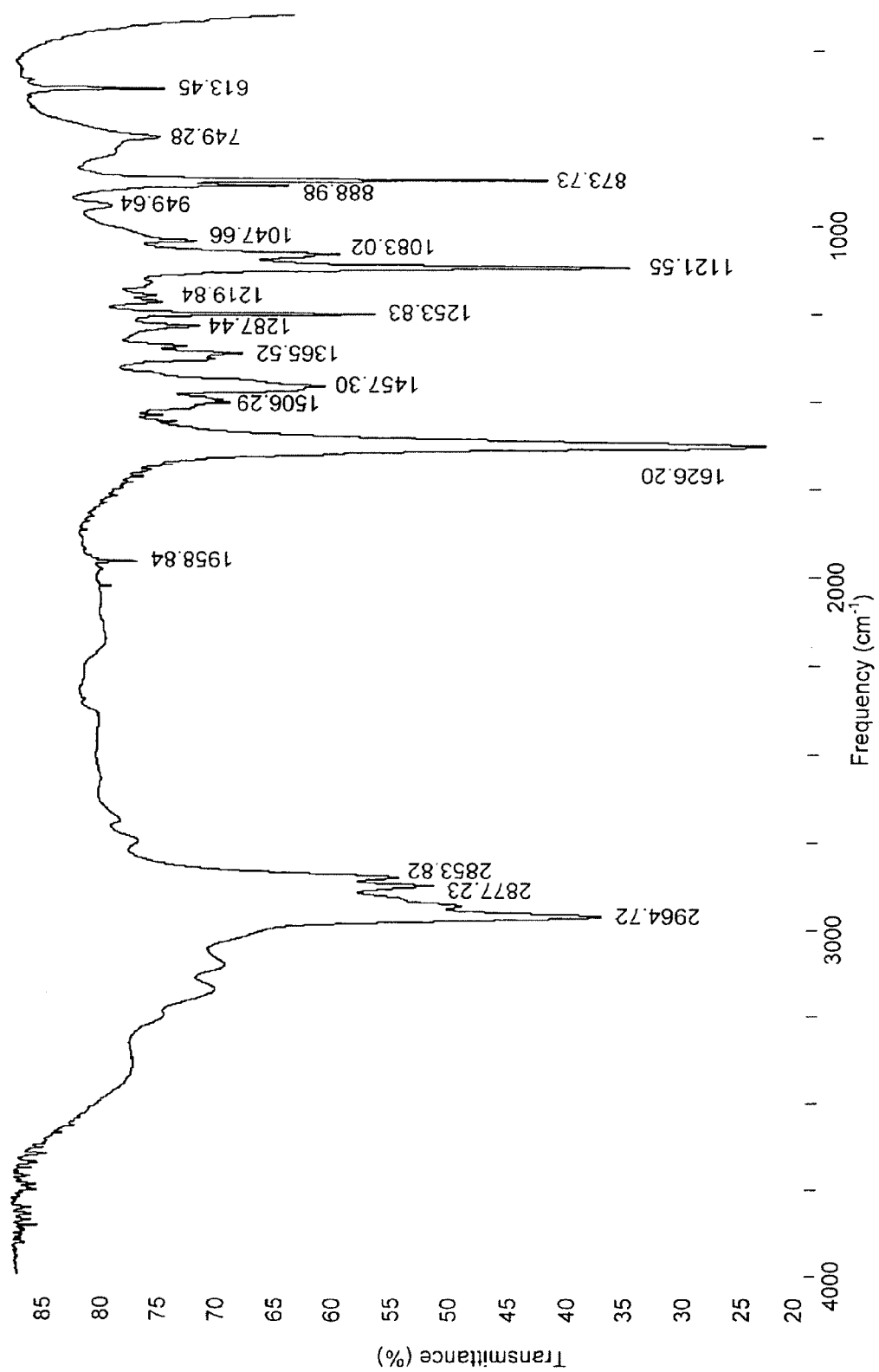
FIG. 6B shows an IR spectrum of N,N,N'-tripropylbutyramidinium chloride between potassium bromide plates.

Referring to FIGS. 6A and 6B, IR spectra of N,N,N'-tripropylbutyramidine and N,N,N'-tripropylbutyramidinium chloride between potassium bromide plates are shown.

Figure 7A:
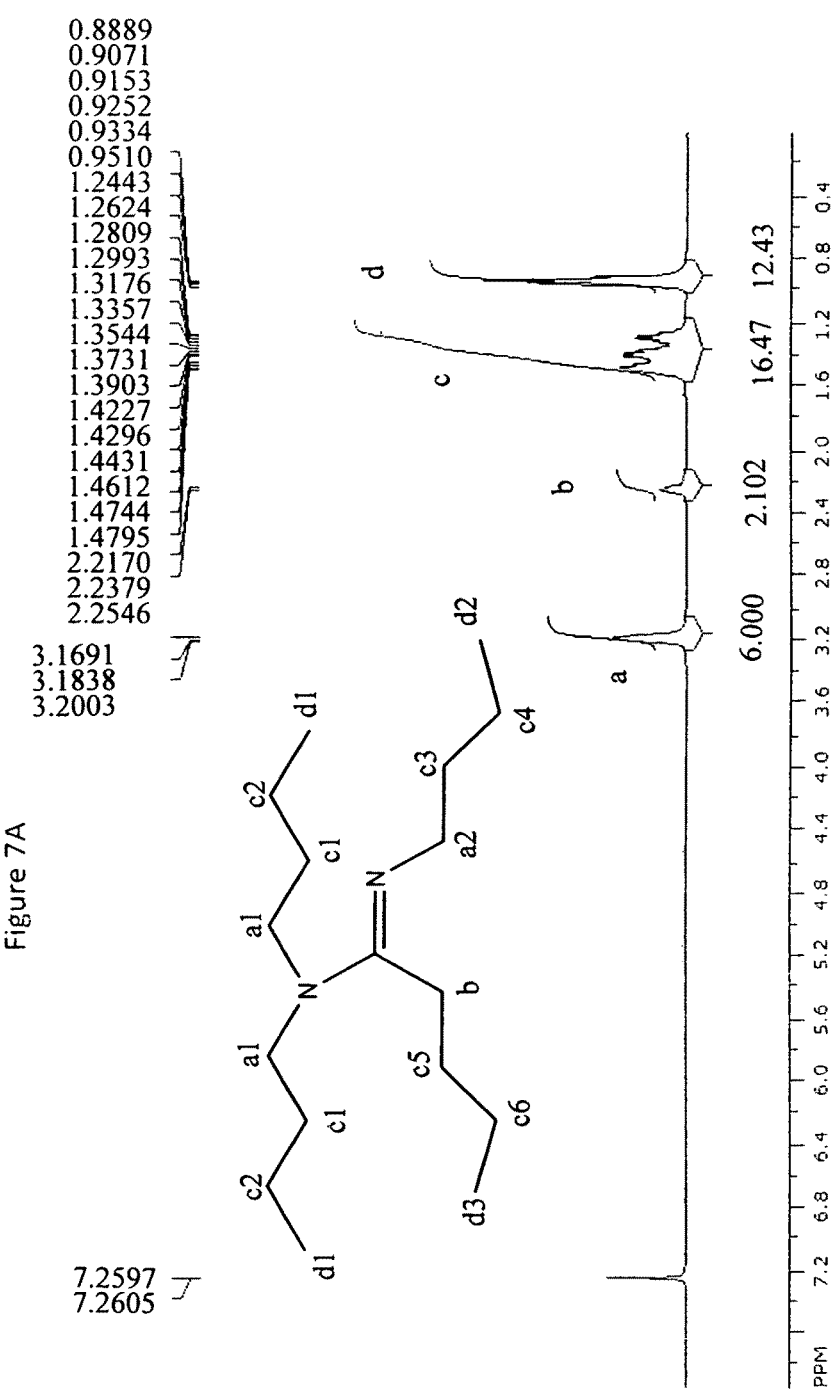
FIG. 7A shows a $^1H$ NMR spectrum of N,N,N'-tributylpentanamidine in $CDCl_3$ at 400 MHz.
Figure 7B:
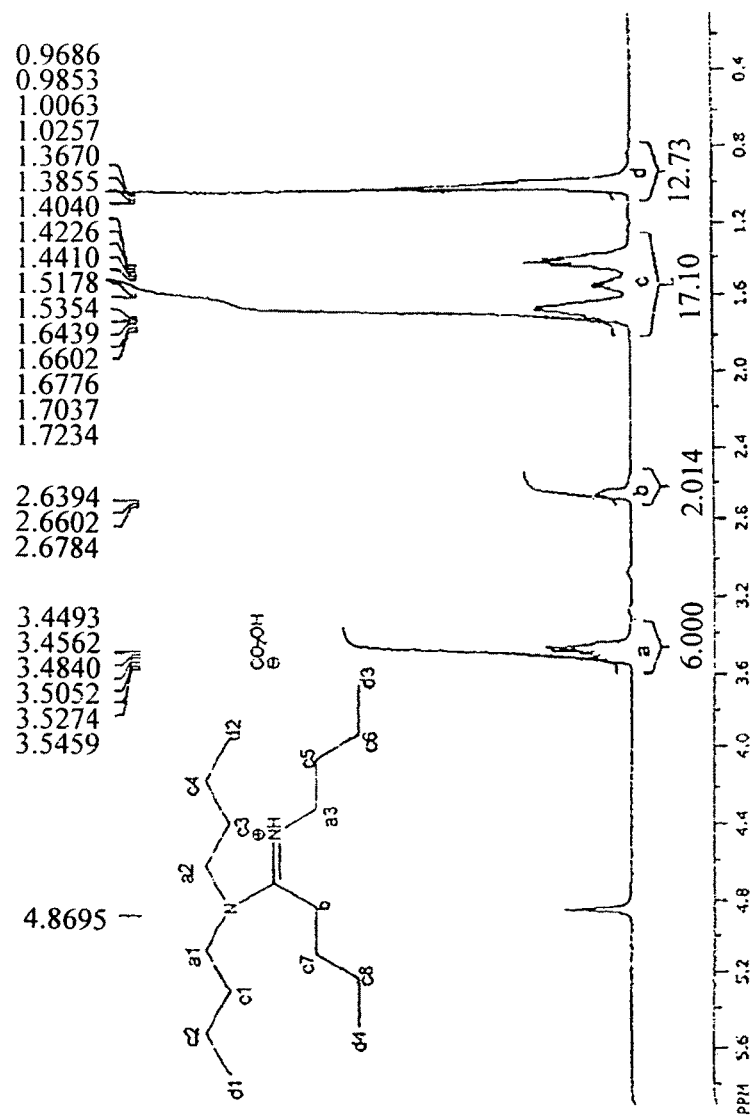
FIG. 7B shows a $^1H$ NMR spectrum of N,N,N'-tributylpentanamidinium bicarbonate in $D_2O$ at 400 MHz.

Referring to FIGS. 7A and 7B, NMR spectra of N,N,N'-tributylpentanamidine and N,N,N'-tributylpentanamidinium bicarbonate in $D_2O$ at 400 MHz are shown.

Figure 8A:
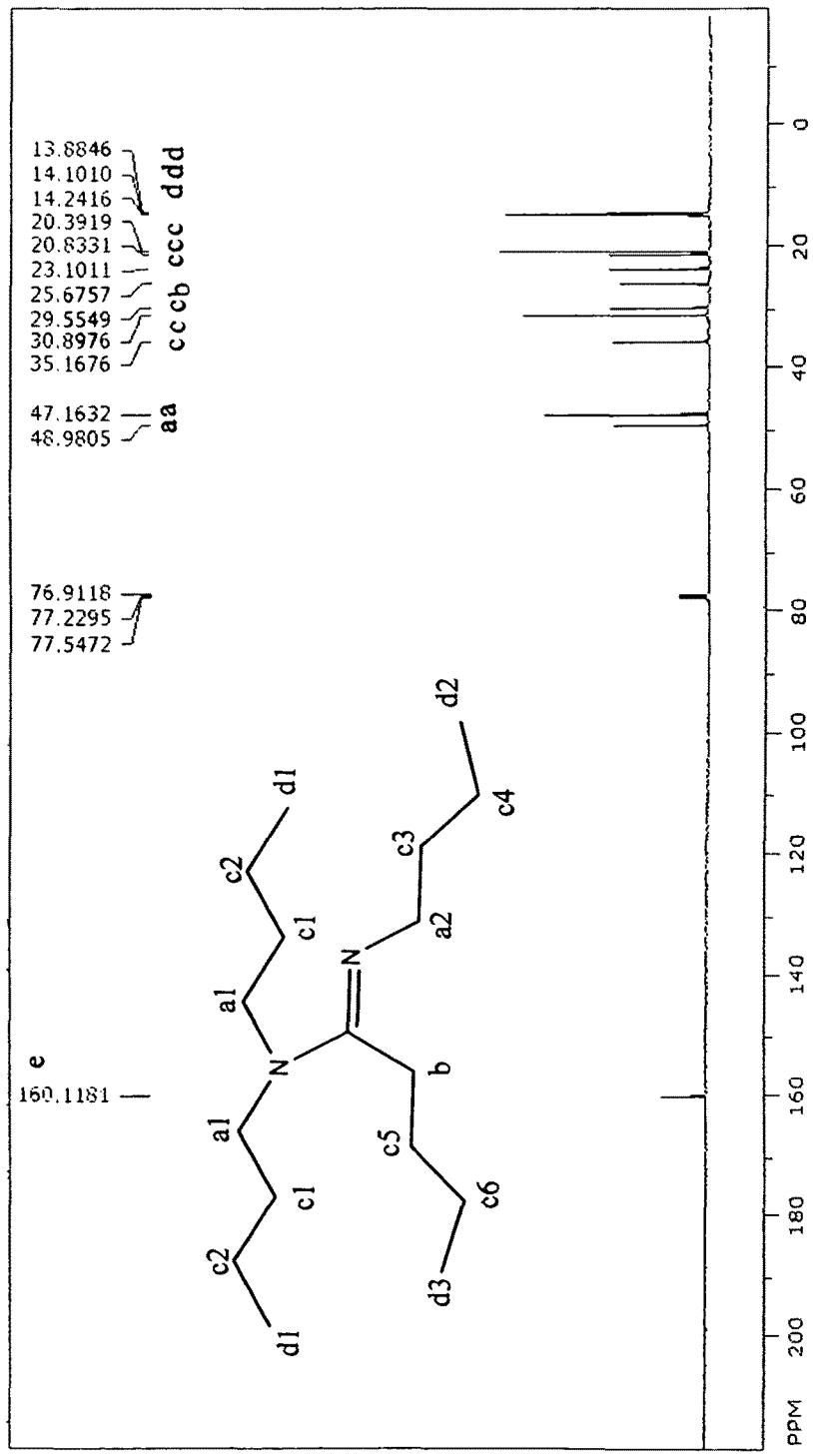
FIG. 8A shows a $^{13}C$ NMR spectrum of N,N,N'-tributylpentanamidine in $CDCl_3$ at 100 MHz.
Figure 8B:
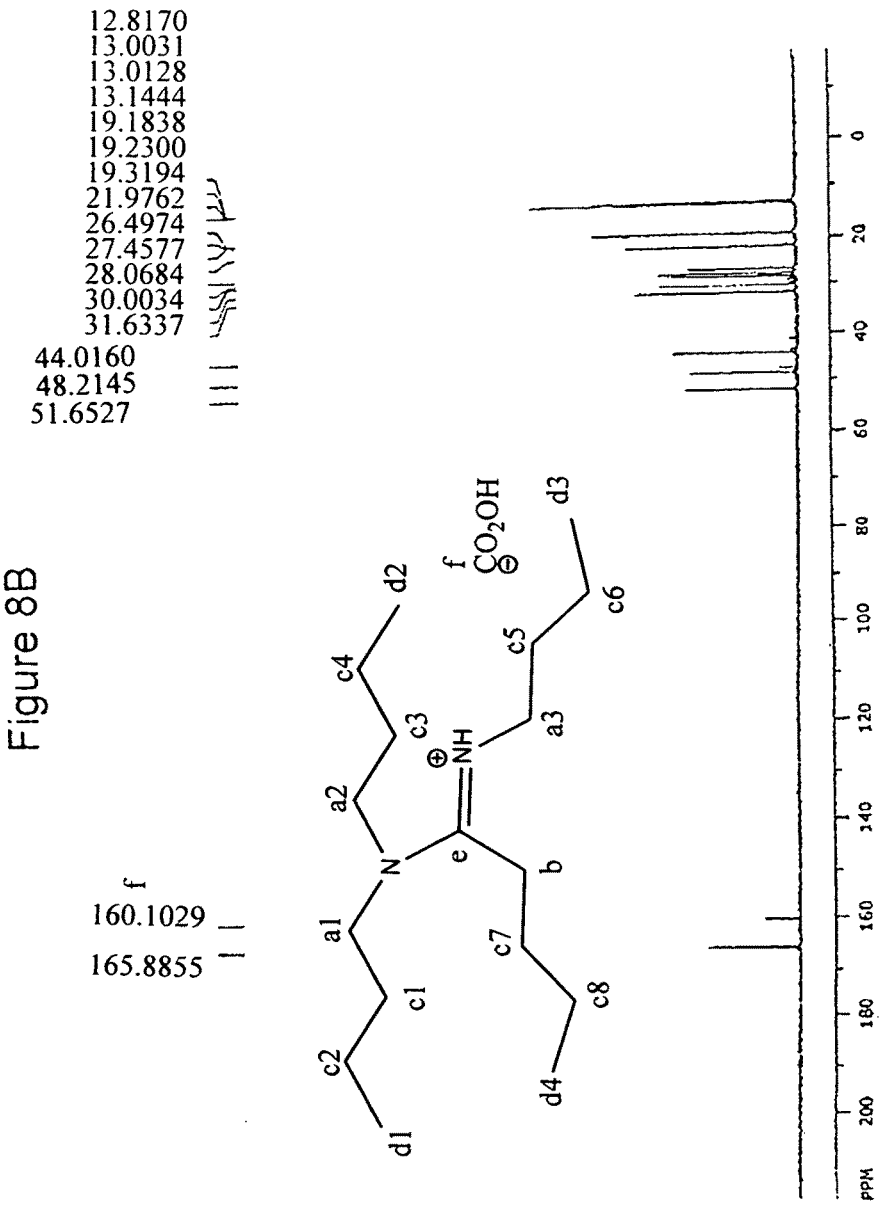
FIG. 8B shows a $^{13}C$ NMR spectrum of N,N,N'-tributylpentanamidinium bicarbonate in $D_2O$ at 100 MHz.

Referring to FIGS. 8A and 8B, $^{13}$C NMR spectra of N,N,N'-tributylpentanamidine and N,N,N'-tributylpentanamidinium bicarbonate in $D_2O$ at 100 MHz are shown.

Figure 9A:
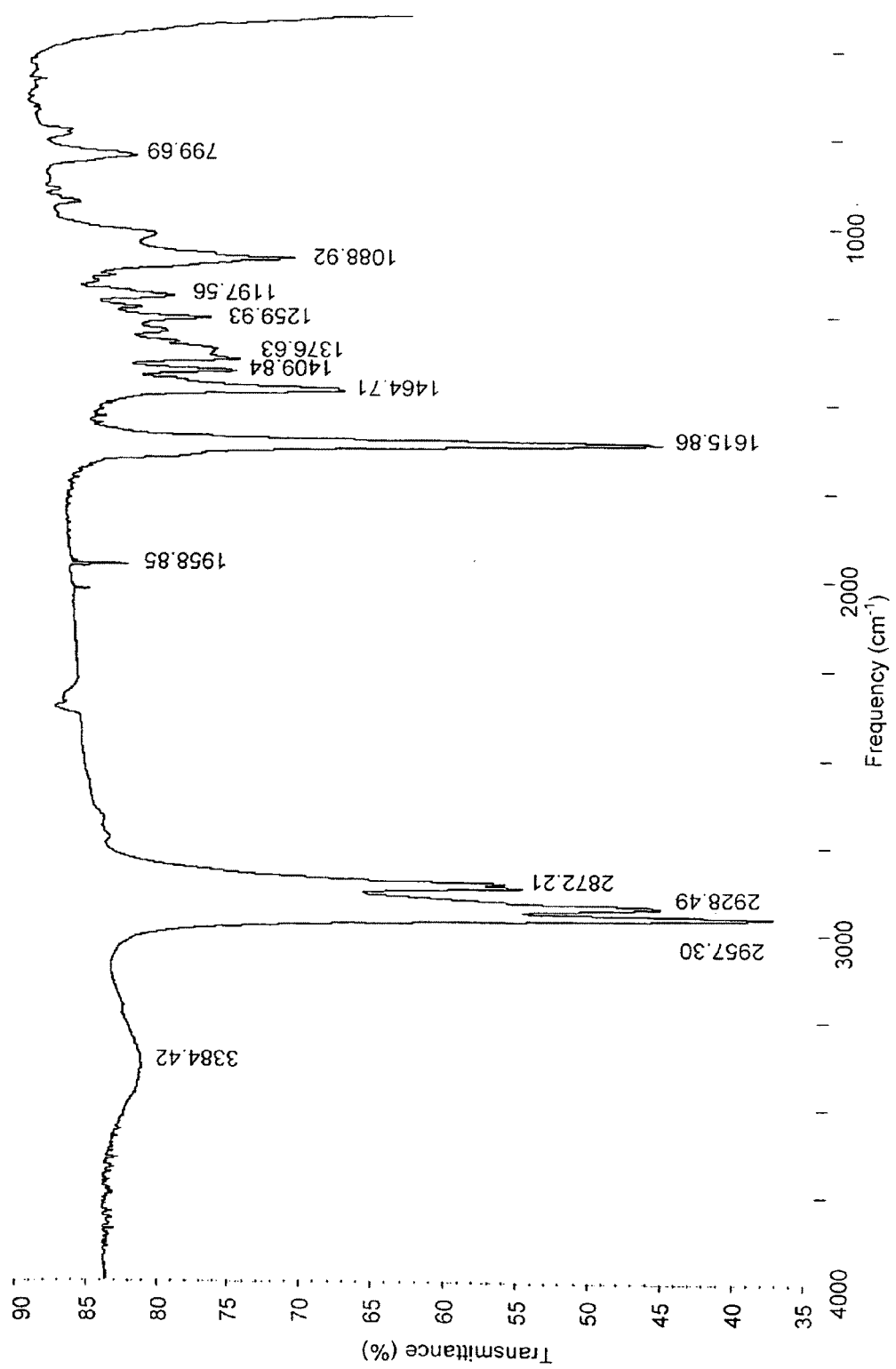
FIG. 9A shows an IR spectrum of N,N,N'-tributylpentanamidine between potassium bromide plates.
Figure 9B:
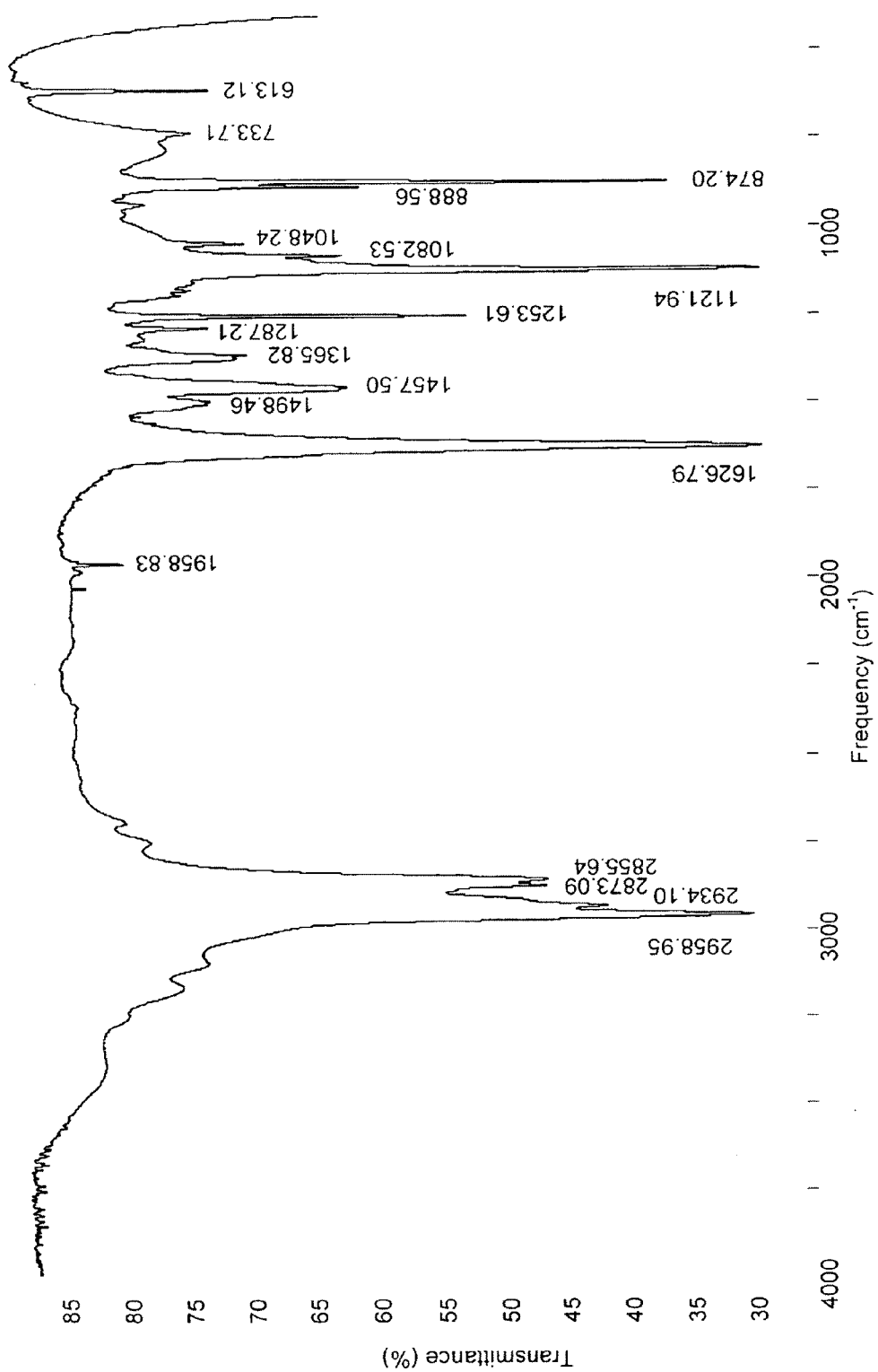
FIG. 9B shows an IR spectrum of N,N,N'-tributylpentanamidinium chloride between potassium bromide plates.

Referring to FIGS. 9A and 9B, IR spectra of N,N,N'-tributylpentanamidine and N,N,N'-tributylpentanamidinium chloride between potassium bromide plates are shown.

Figure 10:
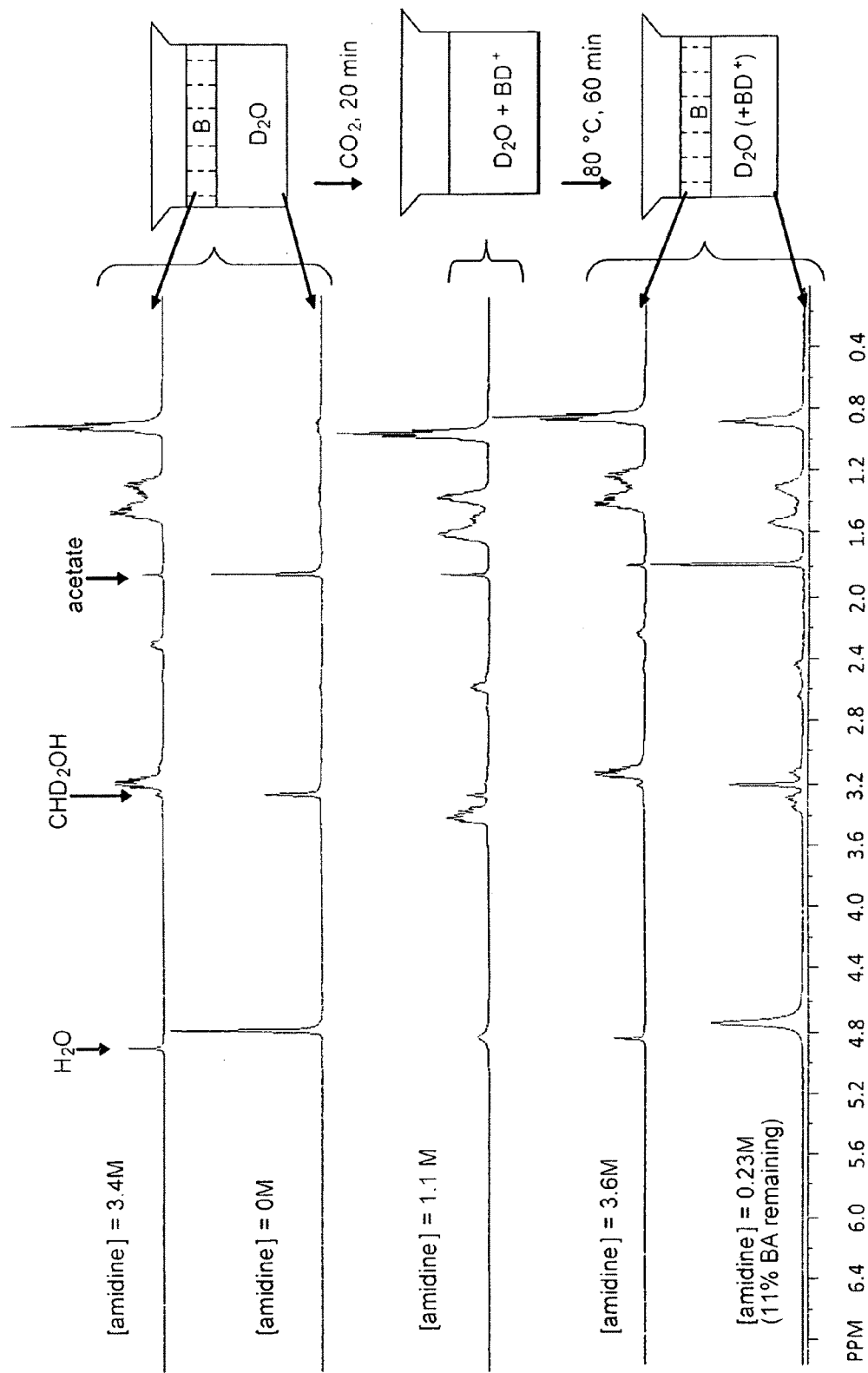
FIG. 10 shows multiple $^1H$ NMR spectra from a N,N,N'-tributylpentanamidine/N,N,N'-tributylpentanamidinium bicarbonate/$D_2O$ switchability study carried out in methanol-$d_4$ at 400 MHz with a sodium acetate internal standard. This is discussed in Example 1D below.

Referring to FIG. 10, multiple $^1$H NMR spectra from a N,N,N'-tributylpentanamidine/N,N,N'-tributylpentanamidinium bicarbonate/$D_2O$ switchability study carried out in methanol-$d_4$ at 400 MHz with a sodium acetate internal standard are shown. This is discussed in Example 1D below.

Figure 11A:
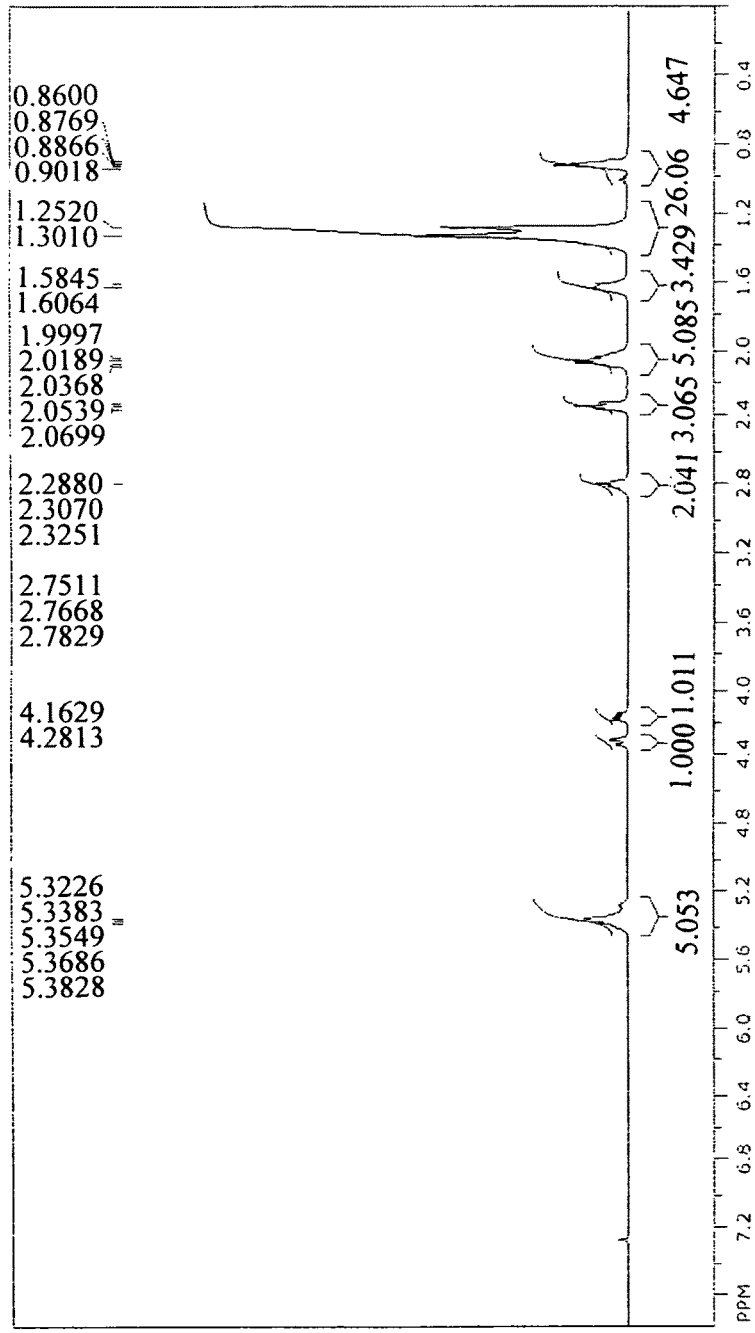
FIGS. 11A-C show multiple $^1H$ NMR spectra in $CDCl_3$ of an extraction study using N,N,N'-tributylpentanamidine with soybean oil (11A), soybean oil and N,N,N'-tributylpentanamidine (11B) and soybean oil after switching (11C). The spectra are discussed in Example 2 below.
Figure 11B:
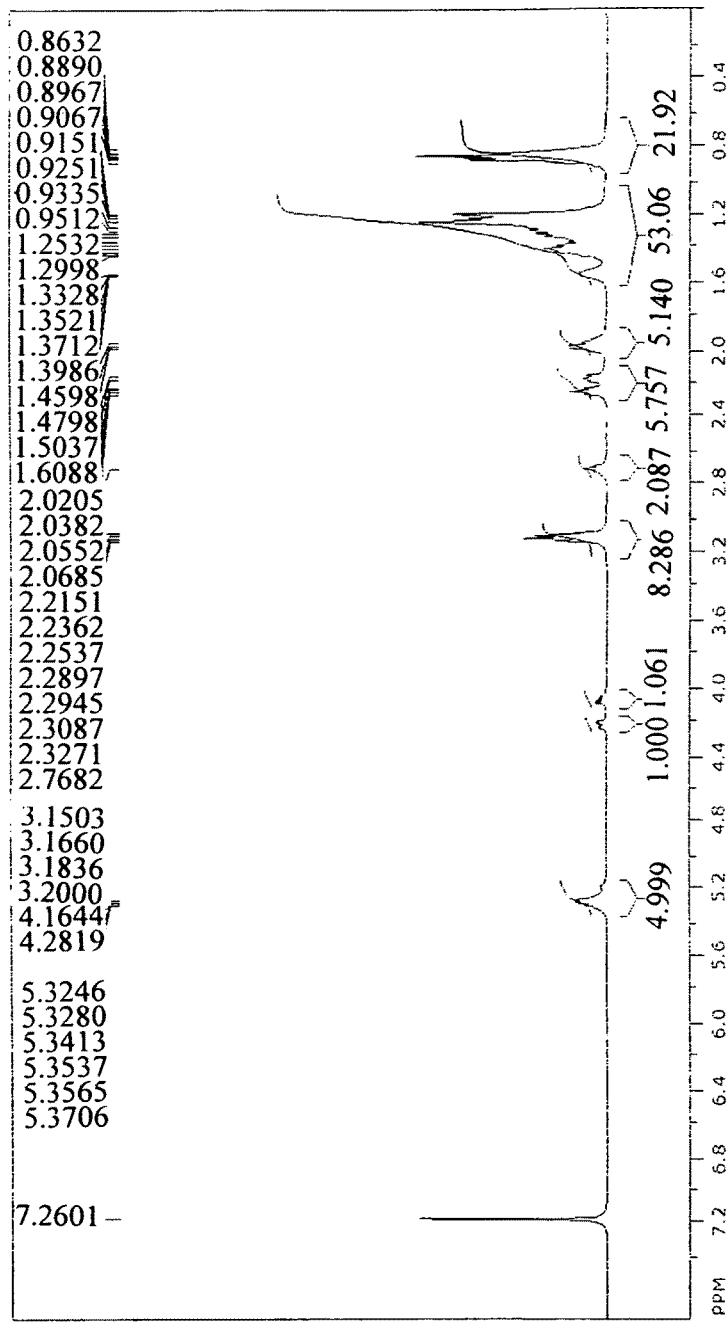
Figure 11C:
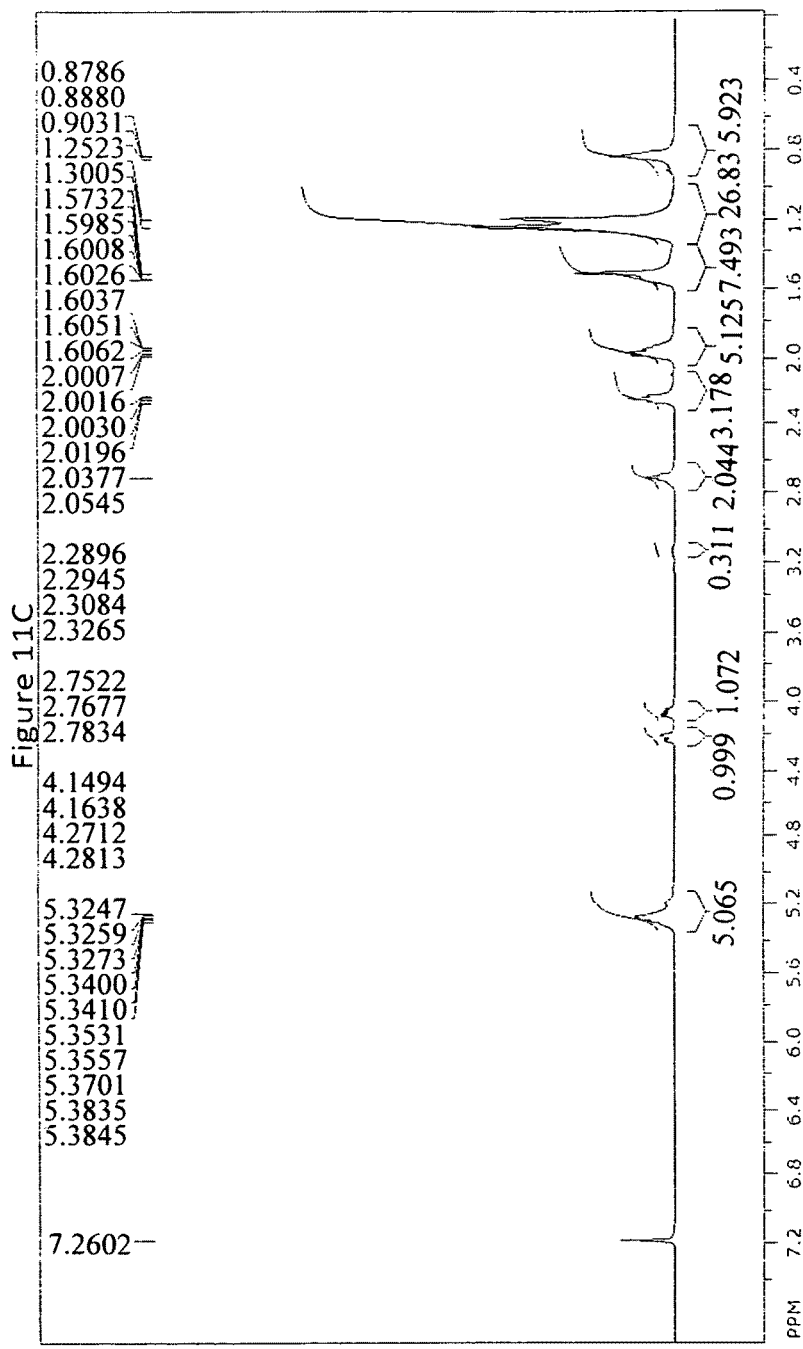

Referring to FIGS. 11A-C, multiple $^1$H NMR spectra in $CDCl_3$ at 400 MHz of an extraction study using N,N,N'-tributylpentanamidine with soybean oil (11A), soybean oil and N,N,N'-tributylpentanamidine (11B) and soybean oil after switching (11C) are shown. The spectra are discussed in Example 2 below.

Figure 12:
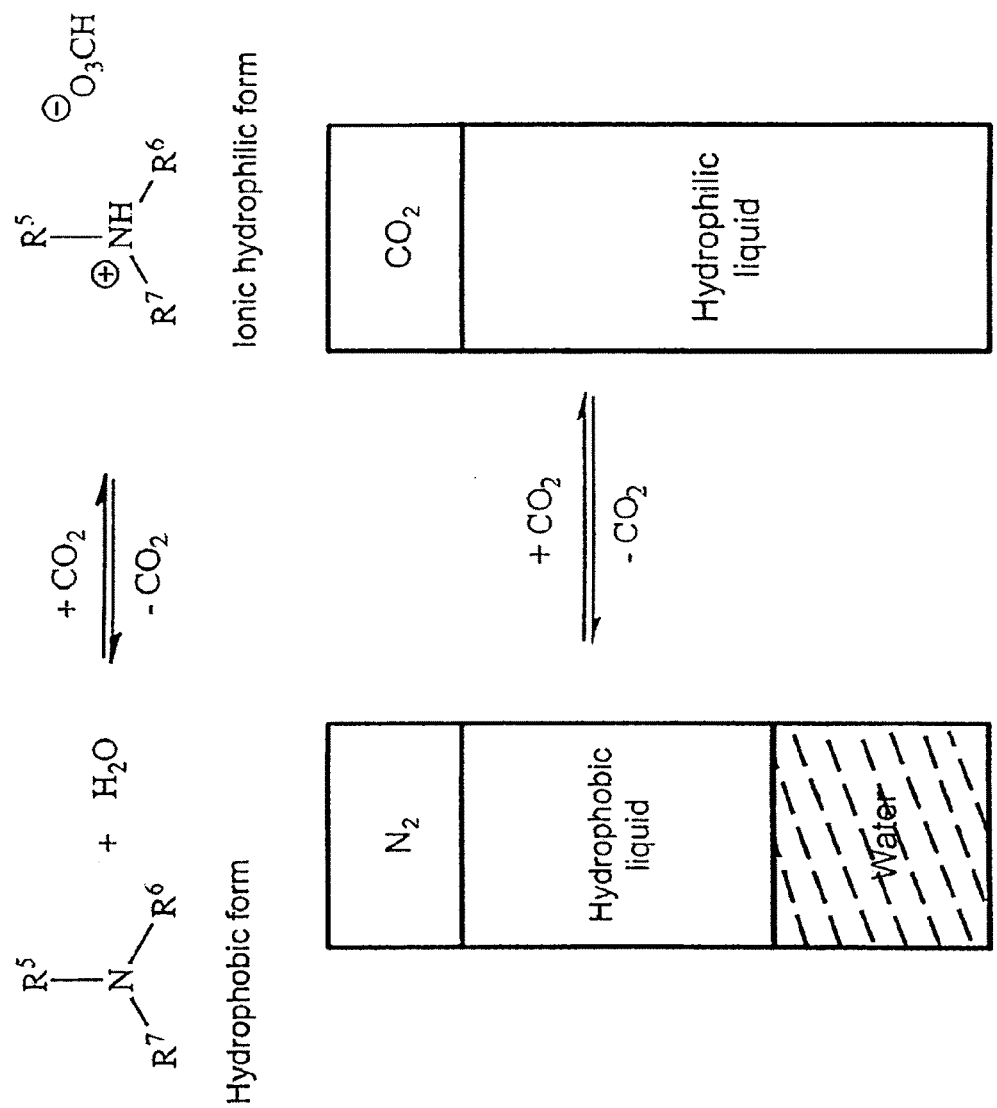
FIG. 12 shows a chemical reaction equation and a schematic of the switching reaction between hydrophobic and hydrophilic forms of an amine.

Referring to FIG. 12, a chemical scheme and schematic drawing are shown for a switchable hydrophilicity solvent system of amine and water. Such a system is further discussed in relation to N,N-dimethylcyclohexane and N-ethylpiperidine, which are examples of water-immiscible compounds of formula (10), in the Examples below. The chemical reaction equation shows an amine (hydrophobic form) and water on the left hand side and ammonium bicarbonate (ionic and thus hydrophilic form) on the right hand side. This reaction can be reversed, as indicated. The schematic also shows the same reaction wherein the two-phase mixture of the compound of formula (10) that is water-immiscible (amine) and water is on the left side under a blanket of $N_2$. The aqueous solution of the salt comprising ammonium bicarbonate is shown on the right side under a blanket of carbon dioxide.

Figure 13:
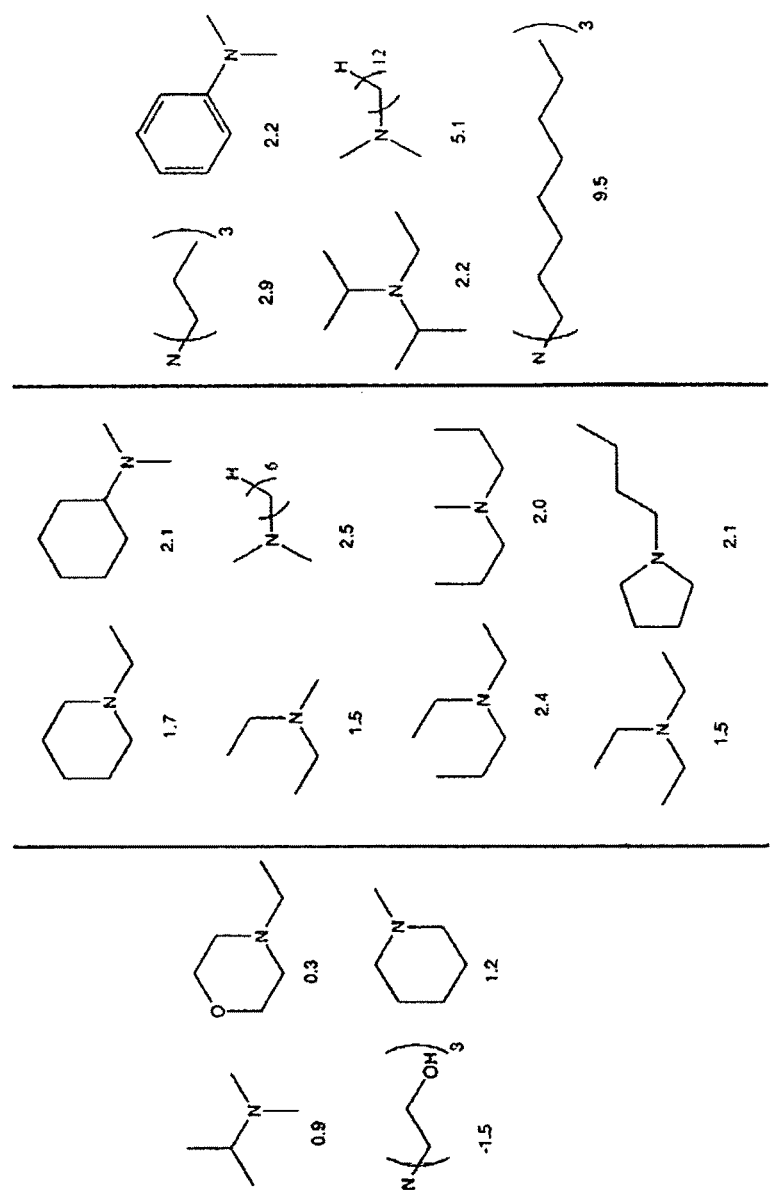
FIG. 13 shows structural formulae and calculated log P values for three groups of various amines. Those in the left group are miscible with water under air or nitrogen and are therefore not switchable hydrophilicity solvents under experimental conditions described herein. Those on the right are immiscible with water even after $CO_2$ gas is bubbled through the liquid mixture and are therefore not switchable hydrophilicity solvents under experimental conditions described herein. Those in the middle section of the figure are immiscible with water under air or nitrogen but become miscible with water after $CO_2$ is bubbled through the liquid mixture and are therefore switchable hydrophilicity solvents under experimental conditions described herein.

Referring to FIG. 13, the hydrophilicity/hydrophobicity of various amine liquids is provided by indicating calculated log P values for each liquid. The compounds are shown segregated into three groups. Those on the left are miscible with water under air or nitrogen and are therefore not switchable hydrophilicity solvents under experimental conditions described herein. Those on the right are immiscible with water even after $CO_2$ gas is bubbled through the liquid mixture and are therefore not switchable hydrophilicity solvents under experimental conditions described herein. It should be understood that under different conditions, such as higher partial pressure of $CO_2$ these compounds may become miscible. Those in the middle section of the figure are immiscible with water under air or nitrogen but become miscible with water after $CO_2$ is bubbled through the liquid mixture and are therefore switchable hydrophilicity solvents under experimental conditions described herein.

Figure 14:
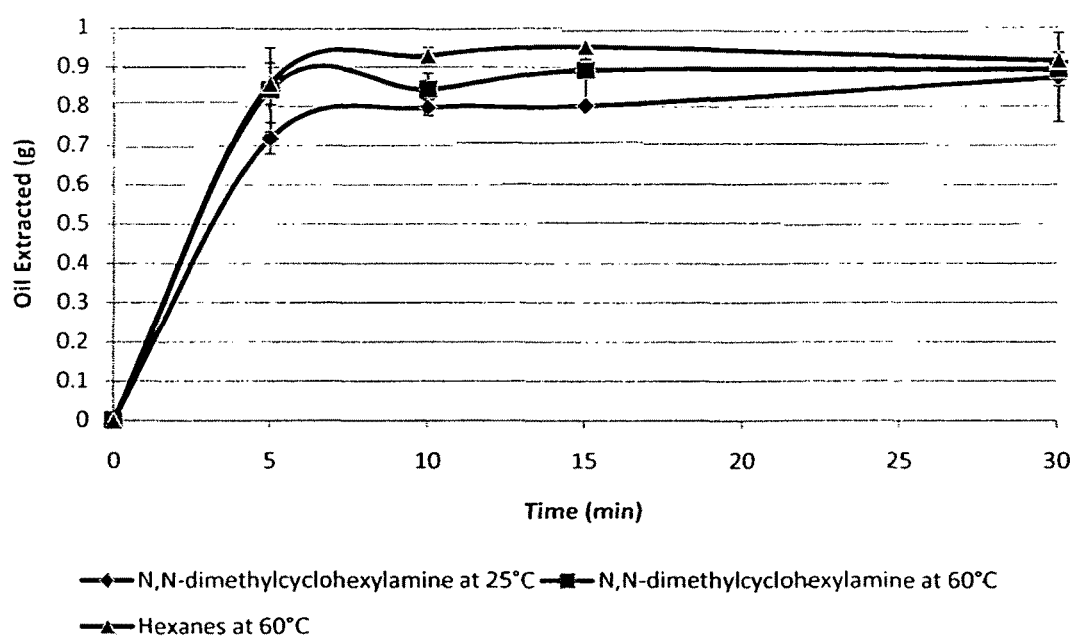
FIG. 14 graphically shows change in mass of soybean flakes vs. time during soybean oil extraction using N,N-dimethylcyclohexylamine at 25° C. and 60° C., contrasted to extraction using hexanes at 60° C., as described in Example 2B.

Referring to FIG. 14, a plot is shown comparing the efficiency of soybean oil extraction by a SHS system using N,N-dimethylcyclohexylamine at 25° C. and 60° C., versus extraction using hexanes at 60° C. As shown, SHS systems are comparably effective, while offering the added advantage of eliminating the need for costly and environmentally-unfriendly distillation of the solvent.

Figure 15:
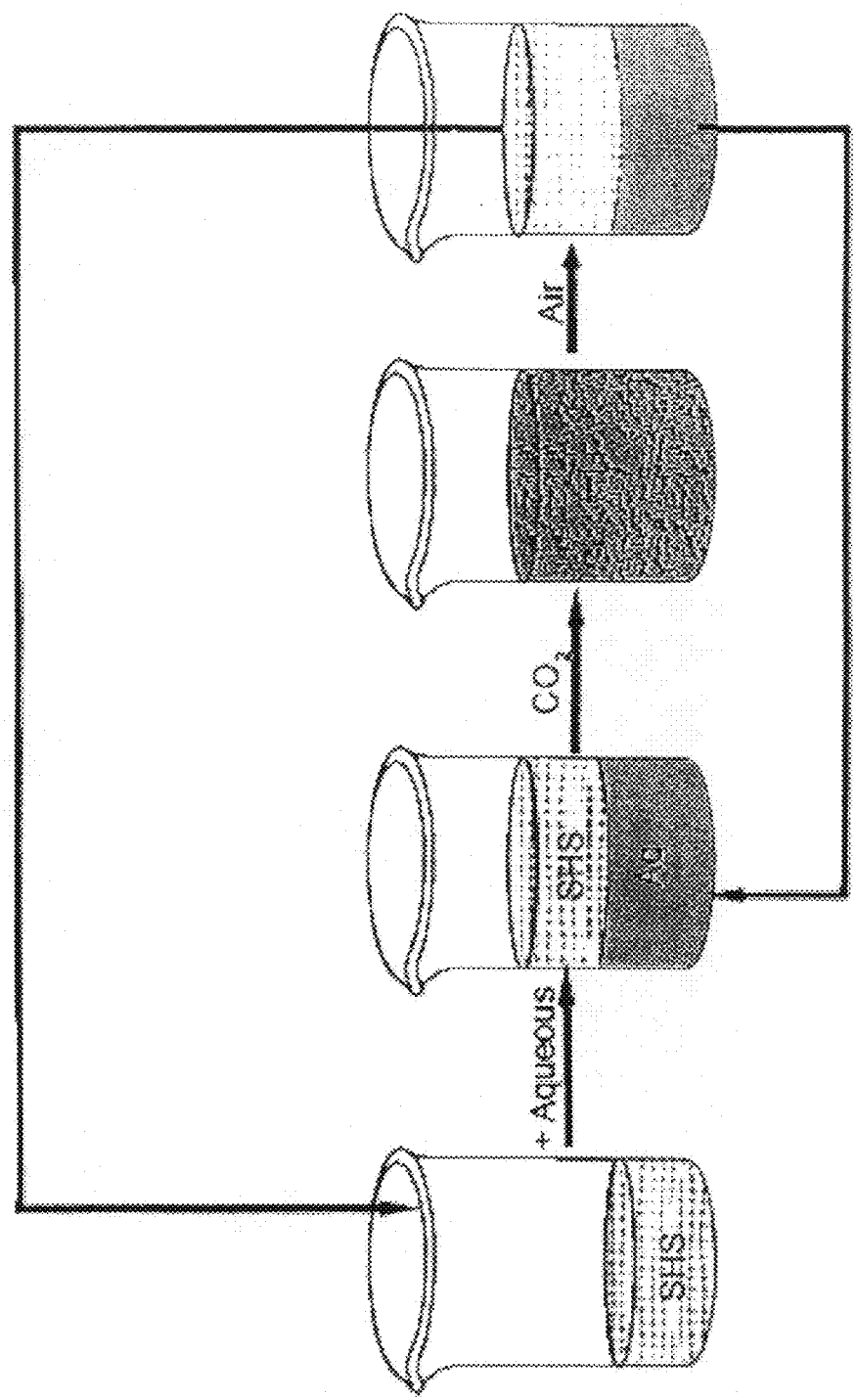
FIG. 15 is a schematic depiction of a system of the invention emptying a switchable hydrophilicity solvent (SHS).

Referring to FIG. 15, a schematic depiction is shown of a system of the invention wherein in the left-most beaker is shown a switchable hydrophilicity solvent (SHS) that is a liquid. When the SHS is exposed to an aqueous solution (e.g., water, salty water, an aqueous solution that includes a dye for analytical tracking to monitor process) a two-layer liquid mixture is formed, as shown in the beaker at the left of centre. When this two-layer aqueous liquid mixture is exposed to $CO_2$ it becomes a single-layer aqueous liquid mixture as shown in the beaker at the right of centre. When this single-layer aqueous mixture has $CO_2$ expelled by exposure to a flushing gas (e.g., air), or heat, or both heat and a flushing gas, $CO_2$ is dispelled from the single-layer liquid mixture, it reverts to a two-layer liquid mixture. As shown by the large arrows, the two layer solutions can be separated from one another, e.g., by decantation, and can be reused in the system. As noted above, in some embodiments the aqueous layer is a salty water solution. Salt water may be an advantage in obtaining a "clean" separation of the two layers and/or diminishing formation of an emulsion.

Figure 16:
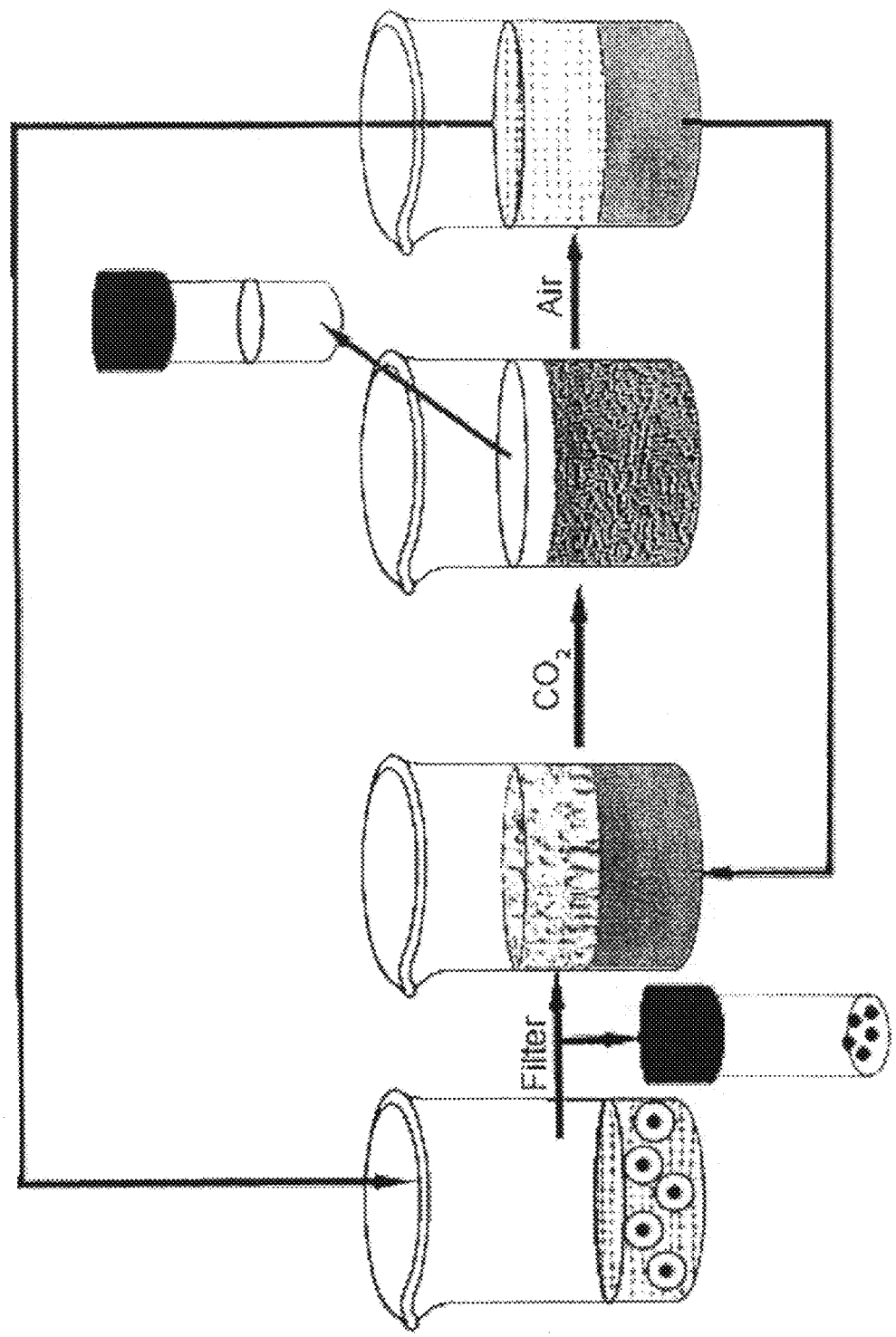
FIG. 16 is a schematic depiction of a system of the invention for removing particles of contaminated solid.

Referring to FIG. 16, a schematic depiction is shown of a system of the invention for removing a hydrophobic contaminant (e.g., cleaning) from particles of contaminated solid, wherein in the left-most beaker is shown (i) a switchable hydrophilicity solvent (SHS) that is a water-immiscible liquid, and (ii) suspended particles of solid that are depicted, for example, as being coated in a hydrophobic contaminant material. The contaminant dissolves in the SHS, and the clean particles can be recovered, e.g., by filtration (as shown in the lower vial). Following removal of the clean particles, the filtrate SHS can be mixed with an aqueous solution as shown in the beaker that is second from the left. Here, a two-layer liquid mixture is shown, the top layer is SHS together with the dissolved contaminant, while the bottom layer is an aqueous solution. Upon exposure to $CO_2$, this two-phase liquid mixture changes to a different two-phase liquid mixture. Specifically, upon exposure to $CO_2$ in the presence of water, the SHS is switched to its protonated form, which is miscible with the aqueous solution and has migrated to the aqueous layer and so the volume of the aqueous layer has increased. The hydrophobic contaminant, which is no longer solubilized by the SHS, has formed a top layer in the third beaker from the left. The contaminant is therefore isolatable from the SHS and aqueous layer by e.g., decantation (as shown in the upper vial). When the contaminant has been removed, the protonated form of the SHS and the aqueous layer can be separated by triggering the water-miscible form of the SHS to switch to the water-immiscible form of the SHS. This is shown by exposing the single-layer aqueous liquid mixture of the third beaker from the left to air. Thus the right-most beaker holds a two-phase liquid mixture. The SHS and the aqueous layer can then be reused as shown by the large arrows. FIG. 16 is intended to represent a system for removing hydrophobic contaminant(s) that is suitable for removal of dirt or odorous compound(s) from plastics (e.g., HDPE, PVC) (see Example 11), removal of drilling fluids and oil from drilling fines (see Example 10), removal of oil from oil sands (see Example 9), degreasing, and remediation of soil contaminated by hydrophobic material.

Figure 17:
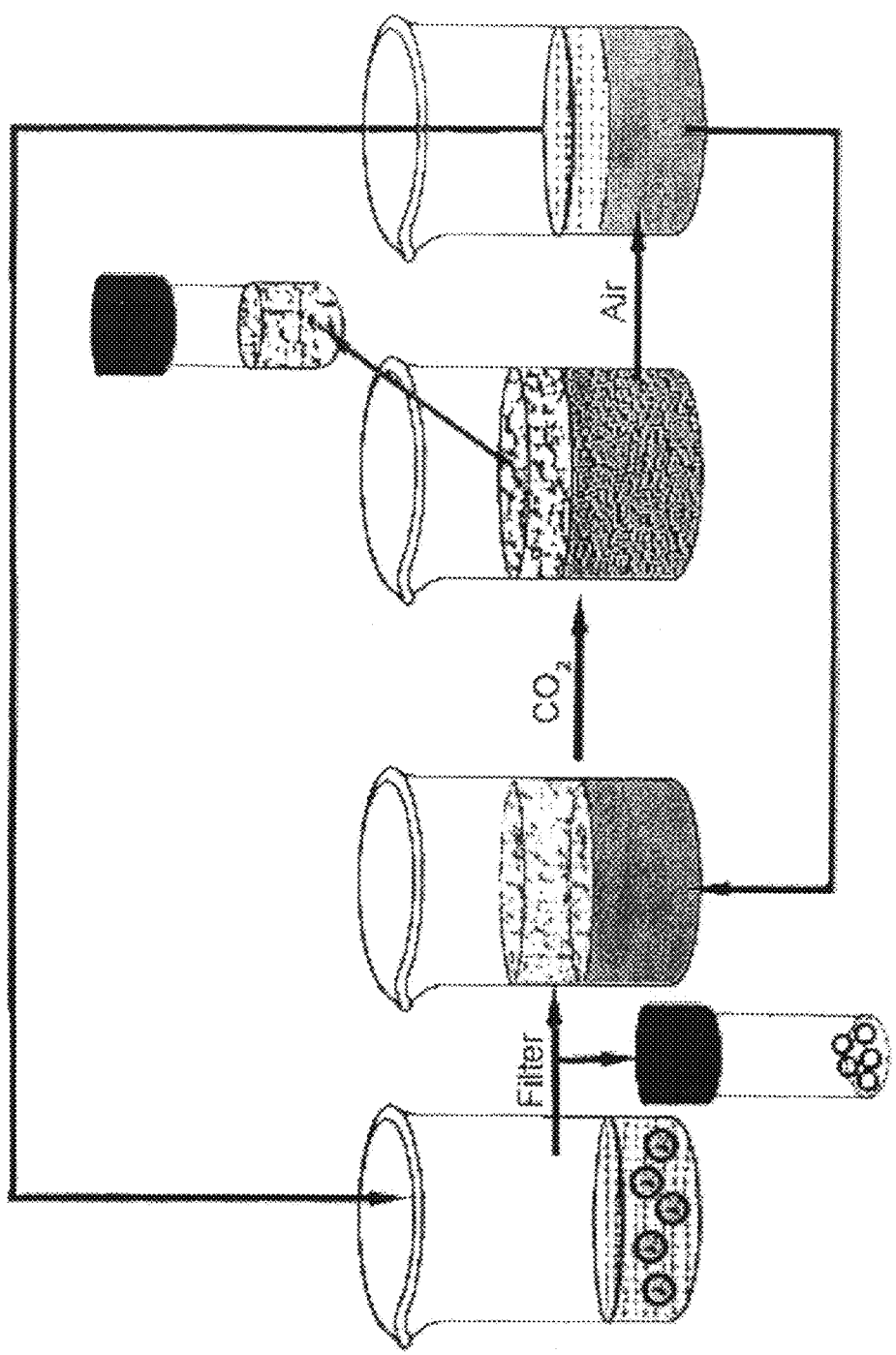
FIG. 17 is a schematic depiction of a system of the invention for extraction of a selected material from a solid.

Referring to FIG. 17, a schematic is shown of a system of the invention for extraction of a selected material (that may be a compound or a group of compounds) from a solid. In the left-most beaker is shown (i) a switchable hydrophilicity solvent (SHS) that is a water-immiscible liquid, and (ii) suspended particles of solid that are impregnated with a hydrophobic selected material. For example, such particles may be seeds impregnated with seed oil, nuts impregnated with nut oil, soy flakes impregnated with soy oil, etc. The hydrophobic selected material is soluble in the SHS, and the barren particles (e.g., oil-less nut flakes, oil-less soy flakes, etc) can be removed by filtration (as shown in the lower vial). Following removal of the barren particles, the filtrate (SHS plus extract) can be mixed with an aqueous solution as shown in the beaker that is second from the left. Here, a two-layer liquid mixture is shown, the top layer is SHS together with the extracted selected material, while the bottom layer is an aqueous solution. Upon exposure to $CO_2$, this two-phase liquid mixture changes to a different two-phase liquid mixture. Specifically, upon exposure to $CO_2$ in the presence of water, the SHS is switched to its protonated form, which is miscible with the aqueous solution and it has migrated to the aqueous layer, and so the volume of the aqueous layer has increased. The hydrophobic extract, which is no longer solubilized by the SHS, has formed a top layer as shown in the third beaker from the left. The extract is therefore isolatable from the SHS and from the aqueous layer by, e.g., decantation (as shown in the upper vial). When the extract has been removed, the protonated form of the SHS and the aqueous layer can be separated by triggering the water-miscible form of the SHS to switch to its water-immiscible form. This is shown by exposing the single-layer aqueous liquid mixture, shown in the bottom layer of the third beaker from the left, to air. Thus the right-most beaker holds a two-phase liquid mixture of the SHS and the aqueous layer. These layers can then be separated by, e.g., decantation, and reused in the appropriate steps as shown by the large arrows. This extraction example is suitable for extraction of seed oils, bean oils, nuts oils, algae oils, and plastic made by bacteria. Such a system for extraction of a selected hydrophobic material is also suitable for extraction of bitumen from oil sands.

Figure 18:
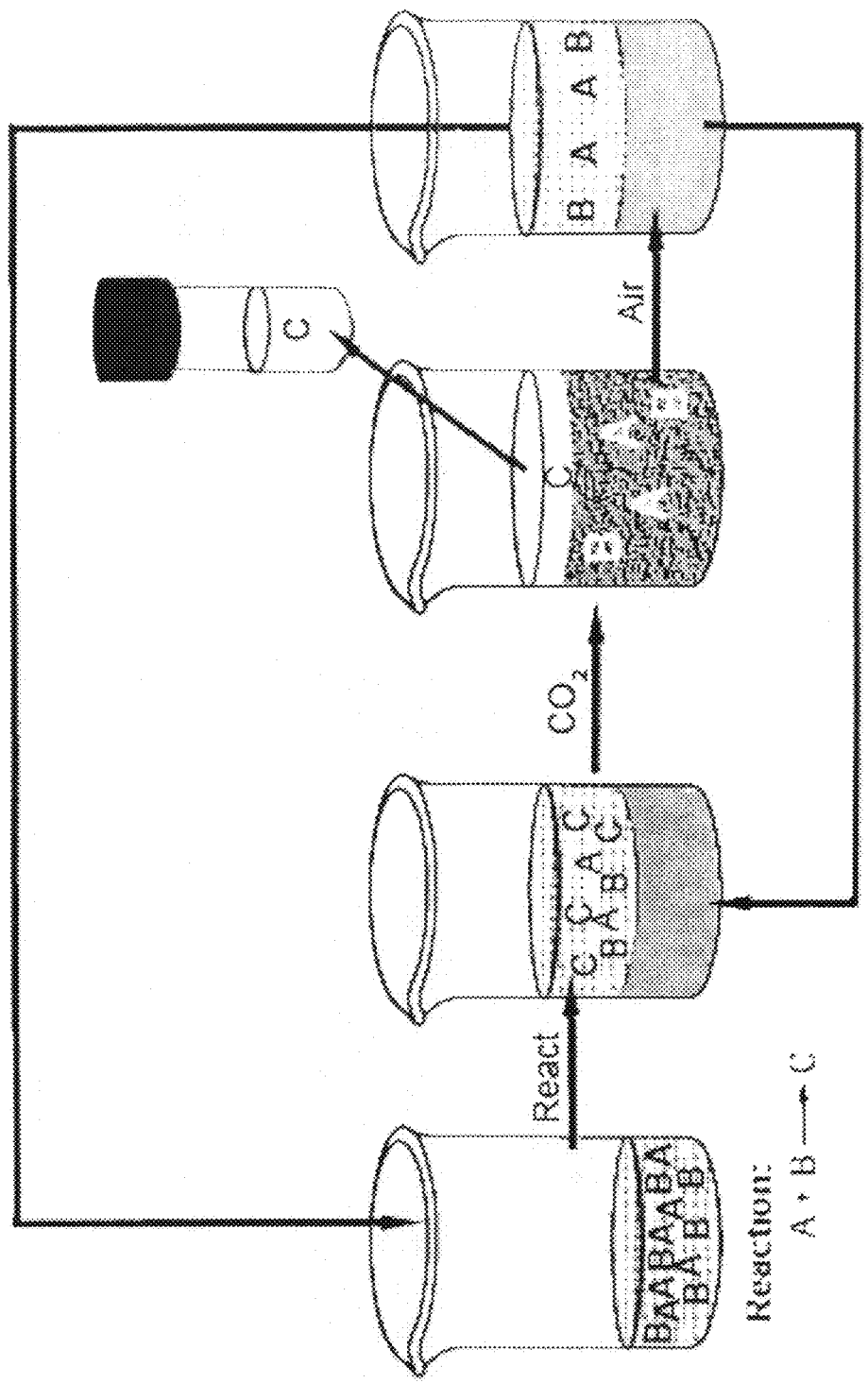
FIG. 18 is a schematic depiction of a system of the invention for isolation of a component in a chemical synthesis.

Referring to FIG. 18, a schematic depiction is shown of a system of the invention for isolation of a component in a chemical synthesis. In the left-most beaker is shown (i) a switchable hydrophilicity solvent (SHS) that is a water-immiscible liquid, and (ii) dissolved reagents (A and B) of chemical reaction A+B→C. In no specified order, the chemical reaction occurs and an aqueous liquid is added. Accordingly, reaction product C is now depicted as dissolved in the SHS (shown as top layer of beaker that is second from the left). Upon exposure to $CO_2$ in the presence of water, the two-phase liquid mixture in the beaker that is second from the left changes to a different two-phase liquid mixture shown in the beaker that is third from the left. Specifically, upon exposure to $CO_2$ in the presence of water, the SHS switched to its protonated form. In this form, it is miscible with the aqueous solution, and it has migrated to the aqueous layer. Accordingly, the volume of the aqueous layer has increased. In this example, reaction reagents A and B are now also in the aqueous layer. Notably, the reaction product C forms a hydrophobic layer and so it is isolatable from the aqueous layer by, e.g., decantation (as shown in the upper capped vial). When this hydrophobic layer has been removed, the protonated form of the SHS and the aqueous layer can be separated by triggering the water-miscible form of the SHS to switch to its water-immiscible form. This is shown by exposing the single-layer aqueous liquid mixture, shown in the bottom layer of the third beaker from the left, to air. Thus the right-most beaker holds a two-phase liquid mixture of the SHS and solubilised reagents A and B, and the aqueous layer. These layers can then be separated by, e.g., decantation and reused in the appropriate steps as shown by the large arrows. This figure is shown to depict a system suitable for isolation of a component of a chemical reaction. The isolated component may be a chemical product, or it may be a side product. This system allows for chemical separation, which may be product isolation, without distillation.

Figure 19:
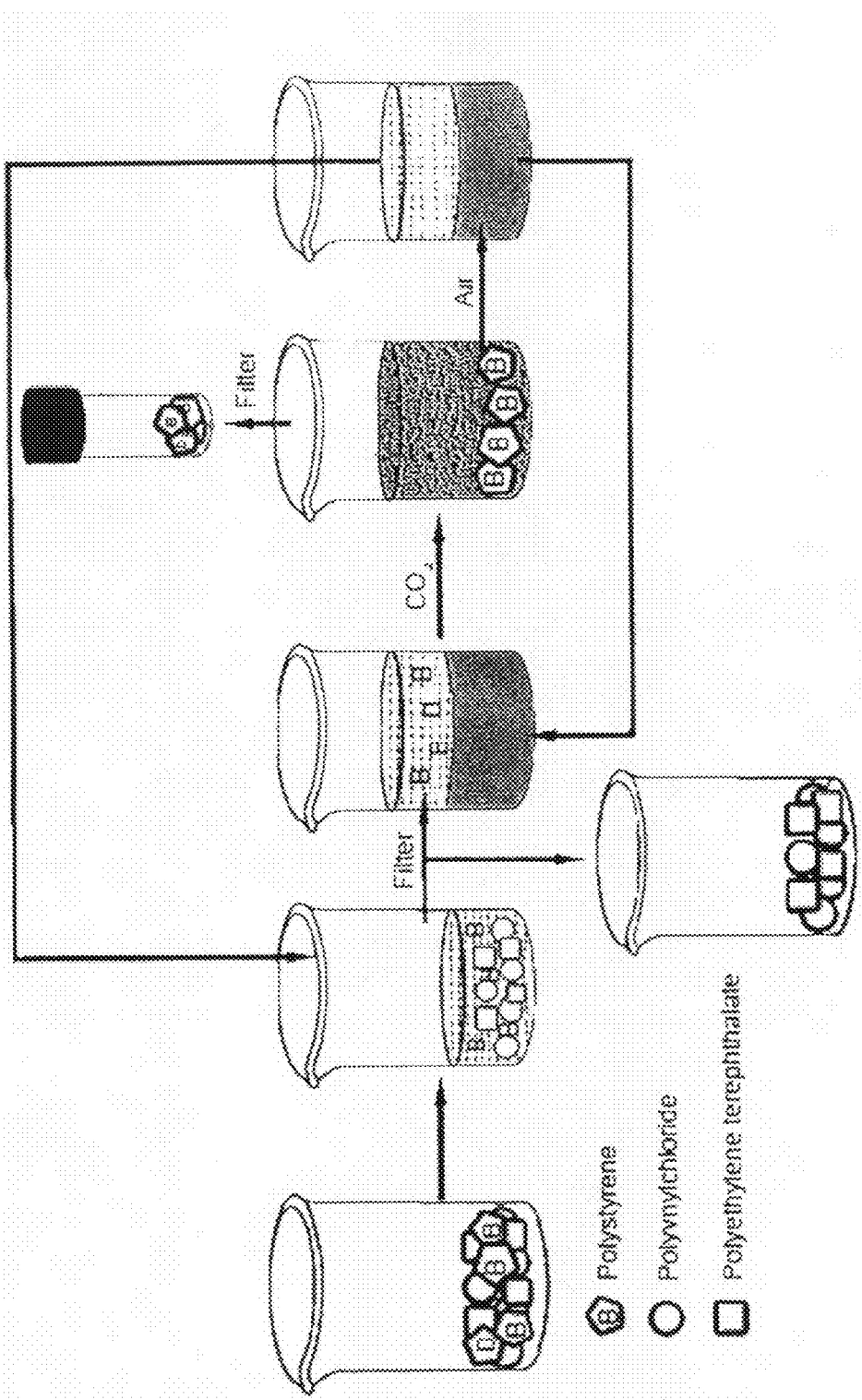
FIG. 19 is a schematic depiction of a system of the invention for isolation of a plastic from a mixture of plastics.

Referring to FIG. 19, a schematic depiction is shown of a system of the invention for isolation of a plastic from a mixture of plastics. In the left-most beaker is shown a mixture of plastics including polystyrene (PS), polyvinylchloride and polyethylene terephthalate. Moving to the right, a switchable hydrophilicity solvent (SHS) that is a water-immiscible liquid, is added and the PS dissolves. Remaining undissolved solids are then removed by filtration to give solids that are polyvinylchloride and polyethylene terephthalate and a liquid filtrate that is SHS and dissolved PS. An aqueous solution is added to the filtrate and a two-layer liquid mixture is shown in the third beaker from the left. This two layer liquid mixture is exposed to $CO_2$ in the presence of water, and a single-layer liquid mixture is formed that is an aqueous solution of protonated SHS. Since PS does not dissolve in aqueous solutions, solid polystyrene precipitates from this single-layer aqueous solution and is isolated by, e.g., filtration or decantation (as shown in the upper capped vial). When the single-layer aqueous mixture is exposed to a flushing gas such as air to dispel $CO_2$ from the liquid, it reverts to a two-layer aqueous liquid mixture. As shown by the large arrows, the two layer solution can be separated by, e.g., decantation and reused. This schematic is provided to show a system wherein polystyrene can be dissolved, optionally separated from other plastics, and collected. A mixture of plastics is intended to include a bale where different types of plastic are bundled together, for example, for recycling. Notably, polystyrene dissolution and recapture is possible in the absence of distillation. As described herein, it is also possible to dissolve a polystyrene foam, thereby removing the gaseous portion of the foam, and collect substantially pure polystyrene.

Figure 20:
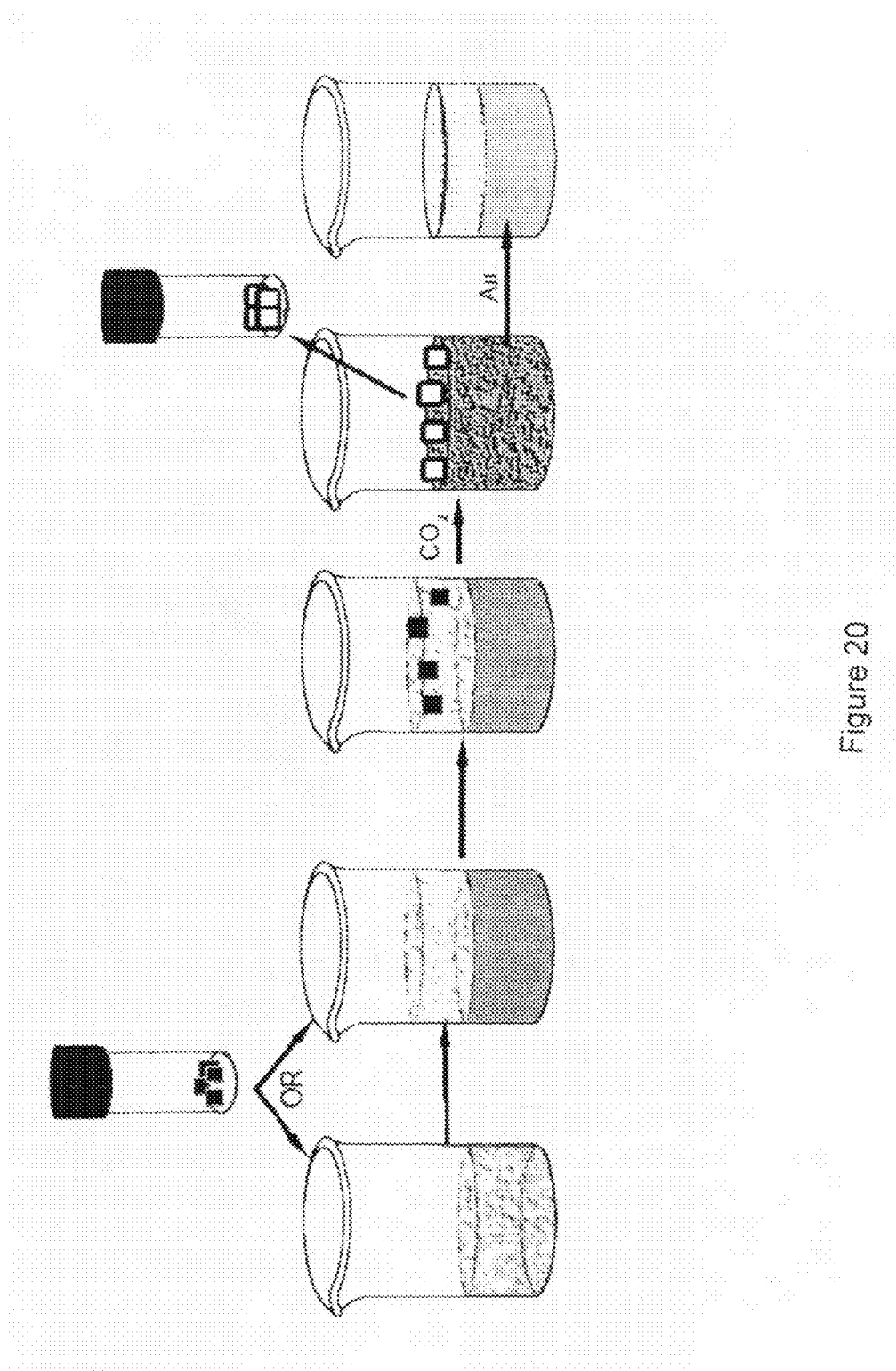
FIG. 20 is a schematic depiction of a system of the invention for adding a hydrophobic compound or compounds to a material.

Referring to FIG. 20, a schematic is shown depicting a system of the invention for adding a hydrophobic compound or compounds to a material. In the left-most beaker is shown a single-layer liquid that is a SHS and dissolved hydrophobic compound or compounds. Solid particles may be added to this left-most beaker, or they may be added to the beaker that is second from left, which holds a two-layer liquid mixture of the SHS+hydrophobic compound, and an aqueous solution. In either case we come to the third beaker from the left which holds a two phase liquid mixture wherein the solid particles are in contact with the SHS+hydrophobic compound. The solid particles become changed and are coated or impregnated by the hydrophobic compound. The SHS can be removed form the solid particles by exposing the two phase mixture in the third beaker from the left to $CO_2$. As shown in the fourth beaker from the left, the liquid becomes a single-layer liquid mixture and the changed solid particles can be isolated by, e.g., filtration or decantation (as shown in the upper capped vial). When the single-layer aqueous mixture is exposed to a flushing gas such as air to dispel $CO_2$ from the liquid, it reverts to a two-layer aqueous liquid mixture. The layers can be separated by, e.g., decantation and reused. This system is depicted to exemplify how a system using SHS can be employed to add dye to textile (e.g., fabric)(see Example 12), functionalize surfaces of, for example, vesicles, or polymer beads, add corrosion inhibitor (i.e., anticorrosion material), surface stabilizers, mordants, antioxidants, preservatives, enzymes, antigens or brighteners, and/or impregnate particles. Impregnation of particles may be applied in the field of, for example, drug-delivery.

As described in the working examples, several salts of formulas (2) and (3) have been formed by reacting carbon dioxide with water-immiscible amidine compounds of formula (1) in the presence of water. Aqueous mixtures advantageously provide a rapid rate of reaction to form water-soluble amidinium bicarbonate compounds from water-immiscible compounds of formula (1), and allow dissolution of the amidinium bicarbonate compounds should they be solid at reaction conditions.

Compounds of embodiments of the invention may have higher aliphatic ($C_5$-$C_{10}$) groups. Monocyclic, bicyclic, or tricyclic ring structures, may also be used. However, too many higher aliphatic groups may cause a compound to be waxy and non-liquid at room temperature. Preferred embodiments of the invention are liquid at room temperature. Also, as the length of an aliphatic group increases, the difference between the hydrophobicity of a water-immiscible compound of formula (1) or of formula (10) and the hydrophilicity of its corresponding ionic form is diminished. The larger this difference, the better the hydrophobic interaction of a water-immiscible compound with the selected substance to be separated, and the better the hydrophilic interaction of its corresponding salt second form with water after switching. For these reasons, preferred aliphatic chain length is 1 to 6. In some embodiments, the compound of formula (1) or (10) has two or more protonatable sites, with the result that the hydrophobicity of somewhat longer aliphatic chains, extra rings, or other hydrophobic structural features can be overcome in the ionic form.

A compound of formula (1) or (10) having a group that includes an ether or ester moiety is also encompassed by the invention. In preferred embodiments, an aliphatic group is alkyl. Aliphatic groups may be substituted with one or more moieties such as, for example, a substituent is independently alkyl, alkenyl, alkynyl, aryl, aryl halide, heteroaryl, non-aromatic rings, Si(alkyl)$_3$, Si(alkoxy)$_3$, halo, alkoxy, amino, ester, amide, amidine, thioether, alkylcarbonate, phosphine, thioester, or a combination thereof. Reactive substituents such as alkyl halide, carboxylic acid, anhydride and acyl chloride are not preferred.

In other embodiments of the invention the $R^{1-7}$ groups of a compound of the invention may not be higher aliphatic; but instead are lower aliphatic groups, and are preferably small, nonpolar and non-reactive. Examples of such groups include lower alkyl ($C_1$ to $C_4$) groups. Preferred examples of the lower aliphatic groups are $CH_3$, $CH_2CH_3$, $CH(CH_3)_2$, $C(CH_3)_3$, $Si(CH_3)_3$, and phenyl. Monocyclic, or bicyclic ring structures, may also be used. If one R group is a higher aliphatic group, such as hexyl or cyclohexyl, then it may be necessary for other R groups to be lower aliphatic groups in order to prevent the compound from being so hydrophobic that the ionic form is not soluble or miscible in water.

It will be apparent that in some embodiments the substituents $R^{1-4}$ may be selected from a combination of lower and higher aliphatic groups. Furthermore, in certain embodiments where there is only one protonatable site in the molecule, the total number of carbon and silicon atoms in all of the substituents $R^1$, $R^2$, $R^3$ and $R^4$ (including optional substituents) of a water-immiscible compound of formula (1) may be in the range of 10 to 20. This provides a good balance of hydrophobicity and hydrophilicity between the two forms.

In this way, a calculated log P value of the compound of formula (1) that is water-immiscible can be provided in the range of about 3 to about 7.

It will be apparent that in some embodiments the substituents $R^{5-7}$ may be selected from a combination of lower and higher aliphatic groups. Furthermore, in certain embodiments where there is only one protonatable site in the molecule, the total number of carbon and silicon atoms in all of the substituents $R^5$, $R^6$ and $R^7$ (including optional substituents) of a water-immiscible compound of formula (10) may be in the range of from 5 to 12 or from 5 to 9. This provides a good balance of hydrophobicity and hydrophilicity between the two forms. In this way, a calculated log P value of the compound of formula (10) that is water-immiscible can be provided in the range of about 1.3 to about 3. In certain embodiments where there is more than one protonatable site in the molecule, the total number of carbon and silicon atoms in $R^5$, $R^6$, and $R^7$ (including optional substituents) may be higher than 9, although not higher than 9 per protonatable site, and the range of acceptable log P values may extend to higher than 3. For amines having two protonatable sites (e.g. diamines), preliminary tests show that the high end of the log P range should be slightly above 4.

In certain embodiments, the amidine compound of formula (1) that is water-immiscible does not have any N—H bonds. If N—H bonds are present, this will lead to an increase in the hydrophilic nature of the amidine. In order to provide an amidine that can be reversibly switched, it is preferred to balance the presence of N—H bonds with longer chain aliphatic groups, such as higher aliphatic groups, to provide an amidine with the desired level of hydrophobic character, i.e., an amidine which is sufficiently hydrophobic to be water-immiscible but not so hydrophobic that the corresponding amidinium carbonate salt is water-immiscible or water-insoluble.

In preferred embodiments, conversion of the compound of formula (1) or formula (10) that is water-immiscible to the salt is complete. In certain embodiments, the conversion to salt is not complete; however, a sufficient amount of the liquid mixture is converted to the salt form to change the properties of the liquid and make it substantially water-miscible. Analogously, in some embodiments, the conversion of salt form back to the hydrophobic compound of formula (1) or formula (10) that is water-immiscible may not be complete; however a sufficient amount of the salt is converted to the hydrophobic compound of formula (1) or formula (10) that is water-immiscible and water to cause the hydrophobic compound to form a separate phase from the aqueous phase.

It should be understood that the invention further encompasses amidines or amines that react to form salts in the presence of water and in the presence of $CO_2$, $CS_2$, COS, or a combination thereof, as discussed herein.

Amidine compounds of formula (1) having a calculated log P value of less than about 3 are less preferred for use in the present invention because they are more hydrophilic in character such that the amidine form may be miscible with water. However, the defining characteristic is immiscibility in water; an amidine that is water-immiscible and yet has a log P below 3 is still acceptable.

Hydrophobicity data for a number of amidines in hydrophobic form is presented in FIG. 2. The amidines A-D exhibit calculated log P values in the range of 1.2 to 2.0. This represents relatively hydrophilic character. The amidines A-D are unsatisfactory for use as a switchable hydrophilicity solvent because they are insufficiently hydrophobic in their amidine form. They were found to be soluble in water in both their hydrophobic amidine form and their hydrophilic salt form as amidinium bicarbonates. Since such amidines are not separable from water after switching from their hydrophilic to hydrophobic forms, they are unsuitable for use in the present invention.

Amidines E and F, representing N,N,N'-tripentylhexanamidine and N,N,N'-trihexylheptanamidine respectively have calculated log P values of 7.8 and 9.1 respectively. The calculated log P values of further amidines (not shown in FIG. 2) have also been determined. N,N-diphenyl, N'-butylpentanamidine (compound of formula (1); $R^1$=$R^2$=butyl; $R^3$=$R^4$=pentyl) has a calculated log P value of 7.0. N-butyl, N-pentyl, N'-butylpentanamidine (compound of formula (1); $R^1$=$R^2$=butyl; $R^3$, $R^4$=butyl, pentyl) has a calculated log P value of 6.5. N-butyl, N-pentyl, N'-pentylhexanamidine (compound of formula (1); $R^1$=$R^2$=pentyl; $R^3$, $R^4$=butyl, pentyl) has a calculated log P value of 7.4. N,N-dipentyl, N'-butylhexanamidine (compound of formula (1); $R^1$=butyl; $R^2$=pentyl; $R^3$=$R^4$=pentyl) has a calculated log P value of 7.4.

Amidine compounds of formula (1) having a calculated log P value in excess of 7 are less preferred for use in the present invention because they are more hydrophobic in character such that the hydrophilic amidinium bicarbonate form would be less readily miscible with water. This may increase the difficulty of separating the salt form from the selected substance it was used to take up in hydrophobic form.

In contrast, the amidines PA and BA, which represent N,N,N'-tripropylbutyramidine (PA) and N,N,N'-tributylpentanamidine (BA) respectively exhibit calculated log P values in the preferred range of about 3 to about 7. These compounds were immiscible with water in their hydrophobic amidine forms, but became miscible after the introduction of a carbon dioxide trigger and water which converted them to their ionic amidinium carbonate forms.

The amidine compounds of formula (1) such as PA and BA, having hydrophobicity in the preferred range exhibited the correct balance of hydrophilicity distributed between hydrophobic and hydrophilic forms. It will be apparent that by varying the $R^{1-4}$ substituent groups, the log P value of the amidines can be adjusted. For instance, using lower chain length substituents will increase the hydrophilicity of the amidine, thus lowering the calculated log P value.

Variations to the structure of compounds PA and BA are well within the skill of the person of ordinary skill in the art pertaining to the invention. These include minor substitutions, varying the length of a hydrocarbon chain, and the like.

Those amidines with log P values in the region of greater than 3 to less than 5 are already relatively hydrophilic (in their amidine form), such that a substantially incomplete switching reaction is sufficient for them to be rendered water-miscible. In addition, because of the greater hydrophilic character of these amidines, greater concentrations may remain in the aqueous phase after the hydrophilic amidinium form is switched back to the hydrophobic amidine. When the hydrophilic amidinium form is switched to the hydrophobic amidine form, a substantial amount must be converted (but not necessarily complete conversion) before a phase separation of the amidine from water is observable.

In the case of embodiments of the invention that involve amidines with log P values in the region of 5 to 7, which are relatively hydrophobic in their amidine form, the switching reaction to form the hydrophilic form must be substantially complete before a single-phase is observable. It will be apparent that this is not a kinetic barrier, but one based upon the relatively hydrophobic nature of the amidine. Also for such embodiments, when the hydrophilic amidinium form is switched back to the hydrophobic amidine form, substantially incomplete conversion to the amidine form will be sufficient for a phase separation to be observable. In addition, because of the greater hydrophobic character of these amidines, lower concentrations may remain in the aqueous phase after the hydrophilic amidinium form is switched back to the hydrophobic amidine.

Amine compounds of formula (10) having calculated log P values of less than about 1.3 are less preferred for use in the present invention because they are more hydrophilic in character such that the amine form may be miscible with water. However, as described herein, immiscibility in water is a defining characteristic; that is an amine that is water-immiscible and yet has a log P below 1.3 is still be acceptable.

Hydrophobicity data for a number of amines in hydrophobic form is presented in FIG. 13. The amines shown in the left column of the figure had calculated log P values in the range of −1.5 to 1.2. This represents relatively hydrophilic character. These amines are unsatisfactory for use as switchable hydrophilicity solvents because they are insufficiently hydrophobic in their amine form. Experimentally, they were found to be soluble in water in their hydrophobic amine form. Since such amines are not separable from water, after switching from their hydrophilic to hydrophobic forms, they are unsuitable for use in the present invention.

Amines shown in the right section of FIG. 13 have calculated log P values of 2.2 to 9.5 respectively. This section shows compounds whose ionic forms have been shown experimentally to be immiscible with water. The ionic form of a switchable hydrophilicity solvent will naturally be more hydrophilic than the non-ionic form, but if the ionic form of a particular amine is not sufficiently hydrophilic (i.e., it is immiscible with water) then the amine is not suitable as a switchable hydrophilicity solvent.

Amine compounds of formula (10) having a calculated log P value in excess of about 3 are less preferred for use in the present invention because they are more hydrophobic in character such that the hydrophilic ammonium bicarbonate form would be less readily miscible with water. This may increase the difficulty of separating the salt form from the selected substance that was solubilized by the corresponding hydrophobic form of the solvent.

Amines shown in the centre column of FIG. 13, including N-ethylpiperidine, N,N,N-triethylamine, N,N-diethyl-N-methylamine, N,N-dimethyl-N-cyclohexylamine, dimethylhexylamine, diethylbutylamine, dipropylmethylamine, N,N-diethyl-N-cyclohexylamine, and N-butylpyrrolidine had calculated log P values in a preferred range of about 1.3 to about 3. Experimentally, these compounds were immiscible with water in their hydrophobic amine forms, but became water-miscible after being subjected to carbon dioxide in the presence of water under which conditions they were converted to their ionic ammonium bicarbonate forms. Accordingly, these compounds are suitable as switchable hydrophilicity solvents of the invention.

Non-limiting examples of amine compounds of formula (10) include N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N,N,N',N'-tetraethylbutane-1,4-diamine and N-butylpyrrolidine. Such compounds and their corresponding ammonium ionic forms have hydrophobicity in the preferred range where their hydrophobic uncharged form is water-insoluble or water-immiscible and their hydrophilic ionic forms are water-soluble or water-miscible. By varying the $R^{5-7}$ substituent groups, the log P value of the amines can be adjusted. For instance, using substituents of shorter chain length increases the hydrophilicity, thus lowering the calculated log P value. Notably, N,N,N-triethylamine and diethylmethylamine are quite volatile. In some embodiments, it is advantageous to have a switchable hydrophilicity solvent that is volatile and so can be readily removed from a mixture. In other embodiments, a switchable hydrophilicity solvent would have low volatility so that the solvent would not have a significant smell, it would not contribute to smog formation or inhalation hazards, and it would not suffer loss due to evaporation during the switching process.

Variations to the structure of compounds N-ethylpiperidine, N,N-dimethylcyclohexylamine, diethylmethylamine, dimethylhexylamine, diethylbutylamine, dipropylmethylamine, triethylamine, and N-butylpyrrolidine are well within the skill of the person of ordinary skill in the art pertaining to the invention. These include minor substitutions, varying the length of a hydrocarbon chain, and the like.

Those amines with log P values in the region of greater than 1.3 to less than 2.0 are already relatively hydrophilic (in their amine form), such that a substantially incomplete switching reaction is sufficient for them to be rendered water-miscible. In addition, because of the greater hydrophilic character of these amines, greater concentrations may remain in the aqueous phase after the hydrophilic ammonium form is switched back to the hydrophobic amine. When the hydrophilic ammonium form is switched to the hydrophobic amine form, a substantial amount must be converted (but not necessarily complete conversion) before a phase separation of the amine from water is observable.

In the case of embodiments of the invention that involve amines with log P values in the region of 2 to 3, which are relatively hydrophobic in their amidine form, the switching reaction to form the hydrophilic form must be substantially complete or close to complete before a single-phase is observable. It will be apparent that this is not a kinetic barrier, but one based upon the relatively hydrophobic nature of the amine. Also for such embodiments, when the hydrophilic ammonium form is switched back to the hydrophobic amine form, substantially incomplete conversion to the amine form will be sufficient for a phase separation to be observable. In addition, because of the greater hydrophobic character of these amines, lower concentrations may remain in the aqueous phase after the hydrophilic ammonium form is switched back to the hydrophobic amine.

Exposure of a 1:1 by volume mixture of two immiscible liquids, hydrophobic PA and water, to gaseous $CO_2$, at 1 atmosphere, caused a conversion to a hydrophilic liquid comprising an aqueous solution of N,N,N'-tripropylbutyramidinium bicarbonate (PAB) (see FIG. 1 for the chemical scheme in which $R^{1-4}$ are propyl). NMR data for the PA/water system is presented in FIGS. 4 and 5 and IR data in FIG. 6. FIGS. 4A and 5A show $^1H$ and $^{13}C$ NMR data for PA. After switching, the detection of the N,N,N'-tripropylbutyramidinium bicarbonate salt was confirmed by $^1H$ and $^{13}C$ NMR as shown in FIGS. 4B and 5B.

Similarly, exposure of a 1:1 by volume mixture of two immiscible liquids, hydrophobic BA and water, to gaseous $CO_2$, at 1 atmosphere, caused a conversion to a hydrophilic liquid comprising an aqueous solution of N,N,N'-tributylpentanamidinium bicarbonate (BAB) (see FIG. 1 for the chemical scheme in which $R^{1-4}$ are butyl). NMR data for the PA/water system is presented in FIGS. 7 and 8 and IR data in FIG. 9. FIGS. 6A and 7A show $^1H$ and $^{13}C$ NMR data for BA. After switching, the detection of the N,N,N'-tributylpentanamidinium bicarbonate salt was confirmed by $^1H$ and $^{13}C$ NMR as shown in FIGS. 6B and 7B. The hydrophilic aqueous solution of BAB was converted back into hydrophobic BA and water by heating at 80° C.

Conversion between a hydrophobic liquid (amidine) and a hydrophilic liquid (aqueous solution of amidinium bicarbonate) results in a change in the properties of the solvent. As described in the Working Examples, the hydrophobic liquid amidine (BA) was miscible with soy oil, an organic compound. The hydrophilic liquid that was formed from BA/water/$CO_2$ was immiscible with soy oil. Thus $CO_2$ and removal of $CO_2$ can be used as triggers of immiscibility and miscibility, respectively.

FIG. 3A presents a comparison of the polarity of BA (hydrophobic liquid form), shown as an open square, and BAB (aqueous solution of ionic form), shown as a black square, as measured by maximum wavelength of absorption of a solvatochromatic dye Nile Red, with other solvents and switchable systems. The complete experiment for BA is described in Example 3 of the Working Examples. Solvatochromatic dyes change color as a result of changes in solvent polarity. The color change is caused by the change in the interaction of the polar ground and excited states of the chromophore in the dye with solvents of differing polarities.

Nile Red, when dissolved in water-saturated BA exhibits a maximum wavelength of absorption of 510 nm. It is evident from FIG. 3A that BA is less polar than many solvents such as toluene, acetone, acetonitrile (MeCN), chloroform ($CHCl_3$), dimethyl formamide (DMF), methanol (MeOH) and ethylene glycol. However, after switching BA to BAB with $CO_2$ in the presence of water, the maximum wavelength of absorption shifts to 570 nm, indicating a relatively high polarity solution having a polarity greater than methanol and ethylene glycol. FIG. 3A further compares the changes in polarity as a result of a $CO_2$ trigger of BA in a water system with other switchable solvents. In particular BA exhibits a dramatic change in polarity upon switching which is significantly greater than 1,8-diazabicyclo[5.4.0]undec-7-ene/propanol (DBU/PrOH), 1,1,3,3-tetramethyl-2-butylguanidine/methanol (TMBG/MeOH), N,N-methylbenzylamine (NHMeBn) and N,N-ethylbenzylamine (NHEtBn). The significant change in properties exhibited by an amidine of the invention upon switching gives rise to a wide range of potential applications.

In some embodiments, the mole ratio of non-gaseous reactants (amidine and water or amine and water) is at least about equimolar. Equimolar ratios can be used when the salt (amidinium bicarbonate or ammonium bicarbonate) is a liquid. It will be apparent to one skilled in the art of the invention that when the salt form is prepared from this mixture, there will remain little or no unreacted reactant(s).

In other embodiments, the ratio of non-gaseous reactants is greater than equimolar, i.e. the number of moles of water is greater than the number of moles of amidine or amine. This provides additional, unreacted water which is not consumed in the switching reaction. This may be necessary to ensure that a single-phase aqueous solution of the salt is obtained. It is preferred that sufficient water is present to dissolve the salt formed after switching, should this be a solid, thereby providing a single-phase aqueous solution. In some embodiments, the volumetric ratio of 1:1 hydrophobic liquid (amidine or amine) to water is preferred.

If insufficient water is present to solubilize a solid amidinium bicarbonate or ammonium bicarbonate salt formed after switching, unsolubilized salt will be present as a precipitate. For instance, should the ratio of amidine (or amine) to water be equimolar, substantially all the water would be consumed in a complete switching reaction. If the salt was a solid rather than an ionic liquid, this would form as a precipitate. The formation of the salt as a precipitate may be advantageous in some circumstances because it is easily recoverable, for instance by filtration.

Solid salts such as bicarbonate salts of switchable hydrophilicity solvents (e.g., see formula (2) and (20) are also convenient for shipping as they are lightweight compared to liquids. Accordingly, in some embodiments of the invention, the salt form of SHS is provided and a user prepares the neutral hydrophobic form either by heating, adding a base, adding water, adding water and heating, degassing and/or flushing with a flushing gas to expel $CO_2$ from the solution. After heating, degassing or flushing an aqueous solution, two layers would be apparent, a layer comprising the hydrophobic SHS and an aqueous layer. These layers are isolatable by, e.g., decantation. Once isolated in this manner, the hydrophobic SHS is obtained and is suitable for many uses as described herein such as removal of contaminant, cleaning, extraction, dyeing, etc.

As described previously and depicted in FIGS. 15 to 20, the water-immiscible hydrophobic SHS can be converted to its water-miscible form by exposure to $CO_2$ in the presence of water. In this fashion, reversibly switchable systems and methods described herein are cyclical and, like the chicken and the egg, can be entered from either starting point (i.e., ionic or neutral forms). For clarity herein, a starting point is designated; however, it is also possible to start with the other form.

In other embodiments, carbon dioxide may be substituted by carbon disulfide ($CS_2$) or carbonyl sulfide (COS). Carbon disulfide is not preferred because of its flammability, its toxicity, and its negative impact on the environment. Carbonyl sulfide is not preferred because of its flammability, its negative impact on human health (irritant, damage to nervous system), and its negative impact on the environment. Both carbonyl sulphide and carbon disulfide may produce hydrogen sulfide upon dissolution in water in the presence of an amidine or amine. Hydrogen sulfide is considerably more toxic than carbonyl sulphide or carbon disulfide. Nevertheless, $CS_2$ and COS should be capable of triggering the same change in the switchable solvents as can $CO_2$.

Carbon dioxide may be provided from any convenient source, for example, a vessel of compressed $CO_2(g)$ or as a product of a non-interfering chemical reaction. The amidines and amines of the invention are able to react with $CO_2$ at 1 bar or less to trigger the switch to their salt form.

It will be understood by the skilled person that regeneration of a water-immiscible compound of formula (1) from an aqueous solution of an salt of formula (2) (or the regeneration of a water-immiscible compound of formula (10) from an aqueous solution of a salt of formula (20)) can be achieved by either active or passive means. The regeneration may be achieved passively if an insufficient concentration of a trigger for the ionic form form, such as carbon dioxide, is present in the surrounding environment to keep the amidine or amine switched to the ionic form form. In this case, a trigger such as carbon dioxide could be gradually lost from the aqueous solution by natural release. No heating, degassing or active contacting with flushing gases would be required. However, heating, degassing or contacting with flushing gases would be quicker but may be more expensive.

A salt of formula (2) can be converted to an amidine compound of formula (1) that is water-immiscible and water by removing the carbon dioxide, for example, by exposing the mixture to a non-toxic flushing gas that contains substantially no carbon dioxide. Similarly, a salt of formula (20) can be so converted to a compound of formula (10). A flushing gas can be any nonreactive gas or mixture of gases that contains insufficient $CO_2$ (or other gas which generates hydrogen ions)

to cause the switch from an amidine to ionic form, e.g., a gas that contains substantially no carbon dioxide. Preferably, the gas is non-toxic. Preferred gases that are substantially free of $CO_2$ include, for example, argon, $N_2$, argon, air that has insufficient carbon dioxide to switch neutral forms that are water-immiscible to ionic salts, and air with the carbon dioxide component removed. In some cases, normal air, without any removal of the existing $CO_2$ content, will suffice as a flushing gas. Conveniently, such exposure is achieved by bubbling the gas through the aqueous solution of ionic form or by any other means of providing efficient contact between the liquid and gas phases. However, it is important to recognize that heating the ionic form is an alternative method of driving off the $CO_2$, and this method of converting the aqueous solution of the ionic form form to its corresponding uncharged form that is water-immiscible is also encompassed by the invention. In certain situations, especially if speed is desired, both bubbling (or other means of providing efficient contact) and heat can be employed. Heat may be supplied from an external heat source, preheated nonreactive gas, exothermic dissolution of gas in the aqueous solution of ionic salt, or an exothermic process or reaction occurring inside the liquid.

Similarly, if the ionic form of formula (2) or formula (20) is isolated as a solid, then heating, degassing and/or contacting with flushing gas can be used to convert the ionic form to the hydrophobic form (amine or amidine).

In some embodiments, the amine or amidine has sufficiently low volatility that the process of switching back the ionic form of formula (2) or formula (20) to the amine or amidine does not result in significant evaporation or distillation of the amine or the amidine.

In initial studies, the trigger used to expel $CO_2$ from solution and to switch from ionic salt to amidine or amine was heat. However, $CO_2$ was also shown to be expelled, and the amidinium ionic salt was converted to the amidine by contacting with a flushing gas, air (see example 1C). It is also expected that $CO_2$ may also be expelled from the ionic form solution merely by passively exposing the solution to air.

Switchable hydrophilicity solvents include water-immiscible amidine compounds of formula (1) with aliphatic portion(s) as discussed below. In certain embodiments, the amidine is peralkylated. The term "peralkylated" as used herein means that the amidine has alkyl or other groups connected to the N atoms so that the molecule contains no N—H bonds. This lack of N—H groups is intended to avoid the amidine form, which should be hydrophobic and water-immiscible, from becoming too hydrophilic because of the hydrogen-bond donating character of the N—H bonds.

An advantage of switchable hydrophilicity solvents is that they facilitate organic syntheses and separations by eliminating the need to remove and replace solvents after each reaction step. With triggers that are capable of causing a drastic change in the hydrophilicity of the solvent while it is still in the reaction vessel, it may be possible to use the same solvent for several consecutive reaction or separation steps. This would eliminate the need to remove and replace the solvent.

Reuse and recycling of solvents of the invention provide economic benefits. The time required to switch between the hydrophilic ionic salts of formula (2) or formula (20) and hydrophobic compounds of formula (1) or formula (10) that are water-immiscible according to the invention is short. For instance, Example 1B shows that an incomplete switch between a BAB ionic salt and BA compound of formula (1) can occur in 20 minutes with heating. Example 1D shows that in excess about 90% of the BAB ionic form can be converted back to the BA compound, which is an example of a water-immiscible compound of formula (1), after heating for 1 hour.

It is advantageous to convert from hydrophobic form to hydrophilic ionic form and then back again (or vice-versa). The solvent in its hydrophobic form could be miscible with another hydrophobic liquid, and then the solvent could be switched to its hydrophilic ionic form to allow for separation of the resulting two liquid components. The liquid components may or may not appear as distinct layers. Separation of the components may include decanting, or centrifuging. After separation, it is desirable to convert a hydrophilic ionic form back to its hydrophobic form and water. Because the hydrophobic form is immiscible with water, it can be separated from the aqueous layer. Thus the solvent can be reused.

The invention provides a convenient system to control the hydrophilicity of an amidine compound of formula (1) or an amine compound of formula (10), which compounds can each be used as a solvent. Thus, it is useful in many industrial applications. For example, a chemical reaction that requires a hydrophobic solvent could be performed in the switchable solvent while in its hydrophobic form. Once the reaction is complete, the solvent could be switched to its ionic form which is substantially incapable of dissolving the product of the reaction. This would force the product to precipitate, if solid, or become immiscible, if liquid. The hydrophilic solvent could then be separated from the product by physical means such as, for example, filtration or decantation. The hydrophilic solvent could then be switched back to its hydrophobic form and reused. This method allows the use of a hydrophobic solvent without the requirement for an energy-intensive distillation step to remove the solvent. Such distillation steps may be complex because both the solvent and the product may have similar boiling points.

Switchable solvents of the invention can be useful in water/solvent separations in biphasic chemical reactions. Separation of a hydrophobic liquid from a switchable solvent may be effected by switching the switchable solvent to its hydrophilic ionic form. This ability to separate solvents may be useful in many industrial processes where upon completion of a reaction, the solvent can be switched to its hydrophilic ionic form with the addition of water and a trigger allowing for facile separation of the two distinct phases. Thus a switchable hydrophilicity solvent may be used in its hydrophobic form as a medium for a chemical reaction. Upon completion of the reaction, the chemical product is readily separated from solution by switching the solvent to its hydrophilic ionic form. The solvent can then be recovered and reused.

In the following Working Examples, two amidines of formula (1), N,N,N'-tributylpentanamidine (BA) and N,N,N'-tripropylbutyramidine (PA), were synthesized in three step procedures. Overall yields for the products were typically 22% (BA) and 31% (PA). The amidines were characterized by $^1H$ NMR and $^{13}C$ NMR spectroscopies.

Both BA and PA show hydrophobic behavior, and were converted to amidinium bicarbonates by bubbling $CO_2$ through an aqueous layer. The hydrophilic amidinium carbonate forms of both amidines were characterized by $^1H$ NMR and $^{13}C$ NMR spectroscopy. Using information from $^1H$ NMR peak integrations, it was determined that BA behaves reversibly in hydrophilic switching; when the amidinium bicarbonate solution is heated as described, allowing 89% of the BA to be recovered.

BA was found to be miscible with soybean oil, and was effectively (96%) removed from the oil by only a single wash with carbonated water. Thus, BA is an example of an switchable hydrophilicity solvent of the present invention with utility in a new process for extracting oil from soybeans.

Initial studies have been conducted to identify applications for switchable hydrophilicity solvents. These studies are described in the working examples and include extraction of residual oil from plastic (e.g., polyethylene) containers. These studies are described to provide an example of the way that switchable hydrophilicity solvents may be used. Accordingly, amounts of solvent or number of washes are provided as a guide and are not limited to those provided in the working examples. In certain cases, less switchable hydrophilicity solvent could be used. In other cases more switchable hydrophilicity solvent could be used. Likewise, the number of washings used is intended as a guide.

In the case of plastic containers and residual oil, such oil may include, for example, vegetable oil, petroleum oil, or a combination of oils. Plastic bottles that are used to house oil are often discarded after use. Recycling plastic chips made from shredding such containers is difficult due to residual oil that sticks to the plastic. Washing such chips with water does not effectively remove the oil, and although addition of surfactant leads to cleaner plastic chips, it makes recovery of the oil difficult and energy intensive. Accordingly, experiments were conducted that showed that switchable hydrophilicity solvents were effective at cleaning plastic chips and led to recovery of the extracted oil with minimal energy input. See Example 7 for details. In brief, switchable hydrophilicity solvents have the ability to extract residual oil from oil-contaminated plastic such as discarded bottles of engine oil, thus allowing the cleaned plastic to be recycled. Plastic chip washing can be done in a batch process or a continuous process. Extracted oil can be readily separated from the switchable hydrophilicity solvent by converting the switchable hydrophilicity solvent, through contact with water and carbon dioxide, to its charged water-soluble form. The charged SHS species is changed back into its neutral form upon removal of carbon dioxide from the system.

Another application for switchable hydrophilicity solvents is its use in converting mixtures of polystyrene and gas (e.g., foam, extruded foam, expanded foam, foam packing material such as pellets or blocks) into high density polystyrene. See Example 8 for full details. Polystyrene foam (also known as STYROFOAM™) has an air content of about 90%; transporting waste polystyrene foam for recycling is consequently very energy intensive. The presence of so much air in the polystyrene foam can also cause problems in the recycling process itself. Being able to remove the air and then transport and recycle a denser polystyrene is advantageous. Polystyrene foam treated in this manner can include expanded polystyrene foam, extruded polystyrene foam, rigid polystyrene foam, high impact thin polystyrene, or polystyrene foam packing chips.

As described in the working examples, switchable hydrophilicity solvent exhibited the ability to dissolve polystyrene foam quickly. During the dissolution, trapped air from the foam was released as visible bubbles of air which escape the liquid. Addition of a mixture of dissolved polystyrene in switchable hydrophilicity solvent to carbonated water facilitated precipitation of denser polystyrene. The switchable hydrophilicity solvent switched to its water soluble ionic form upon contact with water and carbon dioxide. Following separation of the denser polystyrene, the ionic form was then changed back into its hydrophobic water-immiscible neutral form by removing carbon dioxide from the aqueous solution. It was then possible to decant off the switchable hydrophilicity solvent from the aqueous layer for reuse.

The inventors envision a dissolving unit comprising a vat housing a system that uses switchable hydrophilicity solvent to dissolve polymer foam, thereby liberating trapped gas, and then switching the SHS such that the polymer precipitates and is collected. Suitable polymeric foams comprise one or more polymers that are soluble in SHS but that are not soluble in aqueous solution. Examples of such polymers include expanded polystyrene foam (EPS), extruded polystyrene foam (XPS), and Styrofoam™. Currently, recycling of such foams is negligible because the economics of transporting such large volume but lightweight materials is discouraging. A dissolving unit of this type could be a portable dissolving unit such as a truck that holds a system that uses SHS. Such a portable dissolving unit would include means for adding polystyrene foam into the SHS (e.g., a chipper), and optionally, means for mixing. Mixing may include stirring, shaking or otherwise agitating. In certain embodiments, when a desired concentration of polymeric foam in solvent has been achieved, the contents of the vat could be transferred (e.g., pumped out) for processing. A pump may be a separate unit or a pump may be included on the dissolving unit. In other embodiments, the system could be equipped to process the mixture. Such units would include means for bubbling $CO_2$ in the presence of water through the liquid mixture of SHS and dissolved polystyrene to change the liquid mixture into a suspension of hydrophilic (i.e., protonated-SHS) form of the solvent, and solid polystyrene. Such a portable dissolving unit would also have means for removal of the solid polystyrene and means for regenerating the hydrophobic form of the solvent by heating, degassing and/or flushing with a flushing gas such that the solvent can be used over and over again. In some embodiments, the dissolving unit has a chipper to increase the surface area of the polymeric foam thereby increasing the dissolution rate of the foam. In some embodiments, the dissolving unit has a stirrer to maintain a consistent concentration throughout the solvent.

Another application for a switchable hydrophilicity solvent is its use for extraction of oils from natural feedstocks, such as soybean oil from soybeans, algae oil from algae, nut oils from nuts, seed oils from seeds, vegetable oils from vegetables. Examples include extraction of canola oil from canola plants, almond oil from almonds, and hemp seed oil from hemp seed. Such oils may be used for a vast number of uses including human or animal consumption, lubricants, and cosmetics. Switchable hydrophilicity solvents may assist with recycling of materials, such as removing the wax coating from milk cartons so that the cardboard can be reused. As described in detail in Example 2 using exemplary switchable hydrophilicity solvent N,N,N'-tributylpentanamidine, once hydrophobic soybean oil is extracted from soybeans using the uncharged hydrophobic form of the switchable hydrophilicity solvent, the extracted oil can be readily separated from the uncharged switchable hydrophilicity solvent by switching the switchable hydrophilicity solvent to its ionic water-soluble form. The charged form of the solvent then partitions into the aqueous phase and the bean oil can be decanted off from the liquid mixture. Conveniently, the ionic form of the switchable hydrophilicity solvent can be recovered for reuse by switching it back into its neutral hydrophobic form by removing $CO_2$.

Another application for a switchable hydrophilicity solvent is its use as a medium for biodiesel synthesis. Biodiesel is made from vegetable (e.g., corn, soybean, algae) oil or animal fats. Methods of making biodiesel are described in Ma, F. et al. (1999) "Biodiesel Production: a review" *Bioresource Technology* 70: 1-15. Advantageously, when biodiesel is synthesized in a hydrophobic switchable hydrophilicity solvent medium, the biodiesel is miscible in the switchable hydrophilicity solvent. Thus they are homogeneous single-layer liquid mixture and optionally, it is possible to separate immiscible by-products. Then switchable hydrophilicity solvent can be readily separated from the biodiesel by extracting the solvent from the biodiesel. Specifically, the switchable hydrophilicity solvent can be switched from its neutral hydrophobic form to its ionic water-soluble form by applying a trigger. An example of such a trigger is an addition of carbonated water. Once switched, a two-layer liquid mixture forms since the aqueous solution of ionic form of the switchable hydrophilicity solvent is immiscible with biodiesel. Once separated, ionic switchable hydrophilicity solvent can be switched back into its neutral hydrophobic form and reused.

Yet another application for switchable hydrophilicity solvents is its use in dissolving and then readily isolating a water-immiscible compound from a mixture. This may include deinking paper to facilitate recycling of paper including newsprint. It may also include dissolving a selected polymer that is in a mixture of reclaimed and recycled material. For example, in a mixture of polystyrene and polyethylene, the polystyrene would dissolve in a liquid comprising a compound of formula (10), but polyethylene would not dissolve. Thus it would be possible to readily separate them, and as described herein, the dissolved polystyrene could then be readily separated from the solution by switching the compound to its water-soluble ionic form.

Another example of using a switchable hydrophilicity solvent to dissolve and then isolate a water-immiscible compound from a mixture is extracting biopolymers from their source cells' biomass. One example of such a biopolymer is a family of polyesters is called "polyhydroxyalkanoate" or more simply "PHA". PHAs are polyesters synthesized and accumulated by many microorganisms such as *Cupriavidus necator* and *Pseudomonas putida*. Switchable hydrophilicity solvents are expected to facilitate collection and purification of such biopolymers by selectively dissolving the hydrophobic polymers. Removal of solid debris is possible via centrifugation to form a supernatant and pellet or via filtration to form a solid and a filtrate. The SHS in the supernatant or filtrate is then switched to its hydrophilic form by contacting the liquid with $CO_2$ in the presence of water. In its hydrophilic form, protonated-SHS migrates to the aqueous layer and a substantially pure layer of biopolymer forms. Accordingly, the biopolymer can be collected using, for example, decantation. Optionally, chemical or mechanical mastication of the bacterial cells can be done to break open the cell walls and facilitate solubilization of the biopolymers by the SHS.

Remediation of water contaminated with hydrophobic compound(s) is also possible using switchable hydrophilicity solvents. This may include waste-water, or water used in industrial processes.

Remediation of soil contaminated by a water-immiscible hydrophobic material is also possible using switchable hydrophilicity solvents. Recovery of oil from oil sands, otherwise known as tar sands or bituminous sand, is possible using switchable hydrophilicity solvents. For example, a spill of oil (e.g., petroleum) on soil could be readily dissolved and then regenerated in a clean and usable form without the use of surfactants, by using switchable hydrophilicity solvents to dissolve the oil and leave behind the clean soil, and then the oil could be readily separated from the solution by switching the solvent to its ionic form. Other examples of such extraction and then separation include hydrophobic material (e.g., oil, drilling fluid) from porous rock, spilled oil from contaminated surfaces, desirable hydrophobic compounds from biological material (plant or animal), ink from paper, hydrophobic compound from clothing, cleaning of machinery (e.g., degreasing, removal of lubricants, etc.). In each case, the extracted substance can be recovered from the switchable hydrophilicity solvent by switching the solvent to its water-soluble or water-miscible form.

Another application of switchable hydrophilicity solvents is extraction of oil from drilling fines. Drilling fines are obtained when subterranean holes are made in search of fossil fuel reserves. Such fines include rock, sand, soil, water, and oil. Typically, drilling fines are contaminated with up to 40% oil. Prior to development of the switchable hydrophilicity solvents described herein, such fines were transported from off-shore drilling platforms to shore by barge. Once on-shore, fines were stored and oil was removed from the fines by bacterial digestion. This procedure was very costly and time intensive.

Using the switchable hydrophilicity solvents described herein, drilling fines can be cleaned and the contaminant oil readily recovered in a short period of time.

In some embodiments, drilling fines would be transported to shore and treated with the SHS to remove the contaminant. This would eliminate the need for long-term storage.

In other embodiments, treatment of the fines would be done on-site. A portion of the platform would be used to treat the fines directly on the drilling platform, which would eliminate the costly transportation and storage. A system for removing oil from drilling fines would include means for washing, mixing and rinsing the fines using a SHS. The rock and sand would then be returned to the site of their removal in a clean oil-free state. As described herein, contacting the oil-contaminated SHS with $CO_2$ in the presence of water would allow for the oil to be readily separated from the liquid mixture. The SHS could then be regenerated and separated from the water by removal of the $CO_2$ by exposure to air. The SHS could then be reused in the drilling fines cleaning system repeatedly.

Aspects of the present invention may be supplied as a kit. In an embodiment of this aspect, the kit includes a compound of formula (1) or a compound of formula (10) in a suitable container.

For example, suitable containers include simple bottles that may be fabricated from glass, organic polymers such as polycarbonate, polystyrene, etc., ceramic, metal or any other material typically employed to hold reagents or food that may include foil-lined interiors, such as aluminum foil or an alloy. Other containers include vials, flasks, and syringes.

Kits may also include instruction materials. Instructions may be printed on paper or other substrates, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

Kits of the invention allow dissolution of a hydrophobic material from a mixture and convenient separation of the hydrophobic material as described herein.

WORKING EXAMPLES

The following chemicals were used as received: dibutylamine (98+%, Sigma-Aldrich ("Aldrich"), Oakville, Canada), butylamine (>98%, Aldrich), Nile Red (Aldrich), valoryl chloride (>98%, Fluka, available from Aldrich), dipropylamine (99%, Acros Organics, available through Fischer Scientific), propylamine (98%, Aldrich), butyryl chloride (98%, Aldrich), dimethylsulfate (99.8%, Aldrich), anhydrous diethyl ether (99.9%, Fischer Scientific, Ottawa, Canada), hexane (99.9%, Fischer Scientific), ethyl acetate (99.9% Fischer Scientific) hydrochloric acid (~12 M, Fischer Scientific), sodium acetate (Fischer Scientific), potassium hydroxide (Fischer Scientific), triethylamine (≥99%, Sigma- Aldrich), 1,4-dioxane (99+% Aldrich), magnesium sulfate (99.5%+, Alfa Aesar, Ward Hill, USA), HCl in dioxane (~4 M, Fluka), triethylamine (>99%, Aldrich), N-ethylpiperidine (99%, Aldrich), N,N-dimethylcyclohexylamine (99% Aldrich, also available through Acros Organics which are distributed through Fisher Scientific, Pittsburgh, Pa., USA), N,N-diethyl-N-cyclohexylamine (available through Pfaltz & Bauer, distributed through Fisher Scientific, Pittsburgh, Pa., USA), N,N-dimethylhexylamine (98%, Aldrich), N,N-dimethylbutylamine (>98%, Fluka), N,N-diethylbutylamine (97%, Aldrich) methyldipropylamine (98%, Aldrich), N-butylpyrrolidine (98%, Aldrich), trioctylamine (98%, Aldrich), tripropylamine (>98%, Fluka), N,N-dimethyldodecylamine (97%, Aldrich), N,N-diisopropylethylamine (99.5%, Aldrich), N,N-dimethylaniline (99%, Aldrich), methanol-$d_4$ (99.8+ atom % d, Aldrich), chloroform-d (99.8+ atom % d, Aldrich), $D_2O$ (99.9+ atom % d, Aldrich), DMSO-$d_6$ (99.9+ atom % d, Cambridge Isotope Labs, St Leonard, Canada), industrial grade RBD (refined, bleached, deodorized) soybean oil (Bunge, St Louis, USA).

Diethyl ether was purified using a double-column solvent purification system (Innovative Technologies Incorporated, Newbury Port, USA). Compressed gasses were from Praxair (Mississauga, Canada): 4.0 grade $CO_2$ (99.99%) and 5.0 grade Ar (99.999%).

Thin layer chromatography (TLC) was carried out on aluminum-backed silica gel 60 $F_{524}$ (available from EMD, Gibbstown, N.J., USA). $^1H$ NMR and $^{13}C$ NMR spectra were collected at 300 K on a Bruker AV-400 spectrometer at 400.3 and 100.7 MHz, respectively. IR spectra were collected on a Thermo Electron Nicolet Avatar 360 FT-IR Enhanced Synchronization Protocol (E.S.P.) instrument (Nicolet Instrument Corporation, Madison, Wis., USA) between potassium bromide (KBr) plates. Mass spectra were collected on a Qstar XL QqTOF (available from Applied Biosciences/MDS Sciex, Foster City, Calif., USA). Ultraviolet absorbance spectra were collected on an ultraviolet/visible spectrometer with UV-Visible Chemstation software (available from Agilent Technologies, Santa Clara, Calif., USA).

Example 1

Reversible Solvent Switching in an Amidine and Water System

Example 1A

IR and NMR Spectroscopic Characterization of the Amidines N,N,N'-tripropylbutyramidine and N,N,N'-tributylpentanamidine and their Amidinium Salts The amidines, N,N,N'-tripropylbutyramidine (PA) and N,N,N'-tributylpentanamidine (BA), can be protonated by carbonic acid, forming N,N,N'-tripropylbutyramidinium bicarbonate (PAB) and N,N,N'-tributylpentanamidinium bicarbonate (BAB). In the presence of hydrochloric acid, they form N,N,N'-tripropylbutyramidinium chloride (PAC) and N,N,N'-tributylpentanamidinium chloride (BAC).

The ability of both amidines to form salts in the presence of acid was characterized. IR spectra of PA and BA were collected by applying a neat sample of the amidines between KBr plates. Chloride (not bicarbonate) salts of both amidines were prepared so that IR spectra of the amidinium cations could be studied. If the hydrophilic amidinium bicarbonates were formed, they would revert back to amidines while attempting to remove water, so neat amidinium bicarbonate spectra were not collected.

These salts were formed by dissolving PA or BA (1.0 equivalent) in a 4 M HCl solution in dioxane (2.0 equivalent HCl). The dioxane and excess HCl were removed by vacuum, and the resultant hydrophilic liquid was applied directly to KBr plates. The IR spectra of the amidinium chlorides are shown in FIGS. 6B (PAC) and 9B (BAC). These can be compared to the IR spectra of the unprotonated amidines shown in FIGS. 6A (PA) and 9A (BA). In both of the amidinium chloride spectra, the N—H stretch appears as a broad peak in the 3200 $cm^{-1}$ range.

Based on the changing position of the C=N stretch in IR spectra from 1616 $cm^{-1}$ in the amidines PA and BA to 1626 $cm^{-1}$ for PAC and 1627 $cm^{-1}$ for BAC, this bond changes strength upon the addition of HCl, which corresponds to protonation of the imine nitrogen and delocalization of the pi-bond. Also, the introduction of a broad peak at 3200 $cm^{-1}$ suggests the N atom's protonation (N—H stretch).

For comparison to the amidines, $^1H$ NMR and $^{13}C$ NMR of amidinium bicarbonates, BAB and PAB, were collected. The samples for these spectra were prepared by adding preparing two 4 mL vials containing 1 mL $D_2O$ and several drops of one amidine to each. The vials were then exposed to $CO_2$ until all traces of amidine disappeared from the water's surface.

The $^1H$ NMR spectra of PAB and BAB shown in FIGS. 4B and 7B respectively show a significant downfield shift in protons 'a' and 'b' when compared to the corresponding protons in PA and BA shown in FIGS. 4A and 7A respectively. They are deshielded in the protonated form, because the positive charge introduced by protonation draws electron density from nearby bonds. The 'a' and 'b' protons are closest to the amidinium moieties, so it follows that they should be the most deshielded with reference to their chemical shifts in the amidines. Although the solvent used for PA and BA was $CDCl_3$, while $D_2O$ was used for PAB and BAB, the changes in chemical shift were not solvent-induced, as they are also evident when both amidine forms are dissolved in methanol-$d_4$.

In the $^{13}C$ NMR spectra, additional peaks were observed in both the PAB and BAB spectra of FIGS. 58 and 8B respectively, as compared to PA and BA shown in FIGS. 5A and 8A respectively. Bicarbonate was observed, at 160 ppm for PAB and BAB, supporting the hypothesis that the amidines are in their amidinium bicarbonate forms in aqueous solution. Additionally, the number of peaks in the $^{13}C$ NMR spectra, aside from the bicarbonate peak, has increased by two (to 12) in the case of PAB and by four (to 17) in the case of PAB. This suggests increased inequivalence of the alkyl groups on the amine nitrogen, compared to their equivalence in the unprotonated amidine. This observation indicates that the imine nitrogen has been protonated. The positive charge allows increased contribution from the resonance form that previously involved creating formal negative and positive charges. Now this resonance contributor does not create any more charges, but allows the positive charge to delocalize, so it is favored.

Example 1B

Qualitative Switchability Assessment for N,N,N'-tributylpentanamidine

The BA amidine's ability to act as a switchable hydrophilicity solvent for the separation of a selected substance is dependent on its ability to switch from the hydrophobic form to a hydrophilic form. This is achieved by adding water to provide an aqueous layer and decreasing the pH of the aqueous layer, namely by dissolving $CO_2$ in the aqueous layer. When carbon dioxide dissolves in water, it forms carbonic acid with $pKa_1$ of 6.4. The resultant dissociation is sufficient to protonate a hydrophobic amidine, causing it to become charged forming a hydrophilic amidinium bicarbonate (BAB). In this preliminary switching study, the amidine's ability to act as a base and its ability to switch hydrophilicity were studied.

Switching behavior was studied for BA over various periods of time. A glass vial (4 mL) was prepared, containing distilled water (1.0 mL) and BA amidine (0.5 mL).

$CO_2$ was bubbled through the vial for roughly 30 minutes, until the top layer had disappeared showing that a hydrophilic solution of BAB in water had been formed.

A magnetic stirrer was placed in the vial. The vial was suspended in an 80° C. oil bath and stirred. The vial was intermittently removed from the bath and monitored for the presence of a second layer after 20, 50 and 75 minutes. The formation of a second layer (hydrophobic BA) was noted after 20 minutes in the oil bath. The volume of the second layer was found to increase over time. This result showed that the conversion of BA from its hydrophobic form to hydrophilic BAB form was reversible with heating.

Example 1C

Regeneration of N,N,N'-tributylpentanamidine (BA) from an Aqueous Solution of N,N,N'-tributylpentanamidinium bicarbonate (BAB) Using Air In Example 1C, the aqueous solution of BAB was switched back to a mixture of BA and water by heating and stirring at 80° C. In this Example, an alternative method of switching back the BAB is provided.

Switching behavior was studied for an aqueous solution of BAB. A glass vial (4 mL) was prepared, containing distilled water (1.0 mL) and BA (1.0 mL) as a two-phase mixture. $CO_2$ was bubbled through the vial for roughly 30 minutes, until the top layer had disappeared showing that a single-phase solution of BAB in water had been formed.

Air was then bubbled through the same glass vial with the single-phase solution for approximately 5 hours at room temperature to displace $CO_2$ from the solution. The formation of a second layer (hydrophobic BA) was noted. This result showed that the conversion of BA from its hydrophobic form to hydrophilic BAB form was reversible by contacting with a gas that contains substantially no $CO_2$.

Example 1D

Quantitative Switching Study of N,N,N'-tributylpentanamidine

A methanol-$d_4$ solution was prepared containing a sodium acetate internal standard (48.8 mM).

Two 4 mL glass vials containing 1.0 mL $D_2O$ and 0.5 mL BA were prepared and shaken. A 50 µL sample was withdrawn from each layer of one vial and combined with 0.50 mL of the sodium acetate standard solution in each of two NMR tubes: the top layer (BA) in a first tube; the bottom layer (aqueous) in a second tube.

Carbon dioxide was bubbled through the unsampled vial until the BA had completely converted to BAB, as evidenced by the disappearance of the top layer. The pH of the solution was measured using pH paper to be approximately 8-9. A 50 µL sample was withdrawn from the BAB/$D_2O$ solution and added to 0.50 mL of the sodium acetate standard solution in a third NMR tube.

The 4.0 mL vial from which the last NMR sample was withdrawn was then heated at 80° C. for 1 h and stirred by a magnetic stirrer. Bubbles of $CO_2$ were observed escaping from the solution and a top layer, hydrophobic amidine, appeared. After cooling the vial to room temperature, a 50 µL sample was withdrawn from each layer and combined with 0.50 mL of the sodium acetate standard in two NMR tubes: the top layer (BA) in a fourth tube; the bottom layer (aqueous) in a fifth tube.

The NMR spectra of all five samples are shown in FIG. 10 with the first to fifth tubes shown from top to bottom. Although the peaks corresponding to the 'a' and 'b' protons showed the greatest change in chemical shift upon protonation of the amidine, the other signals were used for quantitative NMR studies of the switching behavior. This is because all appropriate solvents interfered with the 'a' protons' signal, while the 'b' protons showed a tendency to exchange with protic solvents, such as methanol-$d_4$ or the $D_2O$ used in switching experiments. In addition, using the 'c' and 'd' protons provided stronger signals, to improve accuracy. Based on the strength of the 'c' and 'd' signals, 11% of the BA remained in the aqueous phase as BAB after the experiment Using dioxane as the internal standard gave the same results (11% BAB retention in the aqueous phase) as sodium acetate.

The same experiment was repeated except that the temperature of the heating of the 4.0 mL vial was increased from 80° C. to 90° C. A similar retention of BAB in the aqueous phase (12%) was observed.

Example 2

Separation of Bean Oil Using Switchable Hydrophobicity Solvents N,N,N'-tributylpentanamidine (BA), N,N-dimethylcyclohexylamine, or N1,N1,N4,N4-tetraethylbutane-1,4-diamine Example 2A Separation of Bean Oil Using Switchable Hydrophobicity Solvent N,N,N'-tributylpentanamidine (BA)

A 4 mL vial was prepared containing 1.0 mL $D_2O$, 0.5 mL BA and 0.5 mL soybean oil. The vial was shaken thoroughly and allowed to settle, showing a 1.0 mL upper layer (soybean oil and BA) and a 1.0 mL lower layer ($D_2O$). $^1H$ NMR samples (50 µL) were withdrawn from each layer and mixed with methanol-$d_4$ (0.5 mL) containing a dioxane internal standard (51.5 mM). Another sample was withdrawn from the upper layer for $^1H$ NMR analysis in $CDCl_3$, because soybean oil is not miscible with methanol. The same volume was discarded from the bottom layer to maintain the initial ratio.

$CO_2$ was bubbled through the system for 1.5 h, at which time the top layer appeared to have halved in volume. Using the same system, $^1H$ NMR analysis was again conducted on both layers, the bottom layer in methanol-$d_4$ and the top layer in $CDCl_3$.

A 1.0 mL portion of the bottom layer was withdrawn and transferred to a new 4.0 mL vial. A magnetic stirrer was added and the vial was stirred at 80° C. for 1 h. Samples were withdrawn from both layers for $^1$H NMR analysis in methanol-$d_4$ with reference to the dioxane internal standard.

The switching behavior of BA in the presence of soybean oil was studied qualitatively and by $^1$H NMR spectroscopy as shown in FIGS. 11A-C. The spectrum of FIG. 11A is that of soy oil. The spectrum of FIG. 11B is that of the upper (organic) phase after the mixing of the BA, soy oil and $D_2O$. This upper phase comprises soy oil and BA. The spectrum of FIG. 11C is that of the upper (organic) phase after the addition of the $CO_2$ trigger and comprises predominantly soy oil and any residual solvent.

The most informative $^1$H NMR spectra in this experiment were those showing the separation of the soy oil and BA. Based on the integration of the peak corresponding to BA at 3.17 ppm in these spectra, 96% of the amidine was removed from the upper soybean oil layer after switching to its hydrophilic BAB form. Other spectra (not shown), collected in methanol-$d_4$ with a dioxane internal standard, confirmed the switching behavior presented in Example 1 above, showing 11% retention of BA in the aqueous phase after heating.

The soybean oil experiment showed that BA is a switchable hydrophilicity solvent for soybean oil extraction. BA is miscible with soybean oil and can be removed by carbonation of the aqueous phase. The amount of amidine BA removed from the soybean oil may be further improved by increased time, smaller $CO_2$ bubbles or agitation. Final traces of the amidine could be removed from soybean oil with an acidic rinse, if necessary.

Example 2B

Separation of Bean Oil Using Switchable Hydrophobicity Solvent N,N-dimethylcyclohexylamine For this study N,N-dimethylcyclohexylamine, 99%, was purchased from Acros Chemicals and used as received. Soy flakes were obtained from Bioenterprise Corporation (Guelph, ON, Canada) and used as received. Hexanes (ACS grade) were purchased from Fisher Scientific (Pittsburgh, Pa., USA) and used as received. In order to simulate reverse flow extraction that is employed in industry, extractions were done at low stir-rates of 200 rpm. Using the same set-up, baseline values were established using hexanes as the solvent.

General Procedure:

To a 100 mL round bottom flask charged with a stir bar was added soy bean flakes (5 g). N,N-dimethylcyclohexylamine (30 g) was then added to the flask and immediately placed in a pre-heated silicone oil bath (25 or 60° C.). The extraction was performed for a range of times of 5, 10, 15, and 30 minutes, a separated experiment was performed for each time interval. Immediately after the timed interval was reached, the flask was removed from the oil bath and the contents were suction filtered using a glass frit until the flakes were dry. The dried flakes were then transferred to a pre-weighed vial, and the weight of the flakes was recorded as mass of oil extracted.

Occasionally, the amine from the oil/amine mixture was removed by solvent removal using compressed air flow. The resulting oily residue was characterized by the use of $^1$H NMR spectroscopy techniques to confirm that the extracted soybean oil wasn't altered by the amine during the extraction process.

Larger Scale Procedure:

To a 500 mL round bottom flask charged with a stir bar was added soy bean flakes (50 g). N,N-dimethylcyclohexylamine (300 g) was then added to the flask and immediately placed in a pre-heated silicone oil bath (60° C.). The extraction was performed for 15, and 30 minutes, a separated experiment was performed for each time interval. Immediately after the timed interval was reached, the flask was removed from the oil bath and the contents were suction filtered using a glass frit until the flakes were dry. The dried flakes were then transferred to a pre-weighed vial, and the weight of the flakes was recorded as mass of oil extracted. The filtrate (amine/oil mixture) was added to a 10 wt % (to amine) piperazine solution (714 mL), see above for discussion of piperazine as a $CO_2$ absorption activator. $CO_2$ was bubbled through the biphasic mixture for about 45 min. The mixture was allowed to settle after which the oil was decanted. $^1$H NMR spectroscopy techniques were used to determine the purity of the soy oil.

Effectiveness of SHS for soybean oil extraction was explored at 25° C. and 60° C. and compared to the industry standard of using hexanes at 60° C. An amount of oil extracted was determined at different time intervals, 5, 10, 15 and 30 min. The solvent/flake mixture was suction filtered to remove the solvent/oil and the residue flakes were left under suction until dry. The extractions performed at 60° C. reached the maximum amount (within error) of oil extracted within 15 min. When the temperature was reduced to 25° C. it took at least 30 min to reach a similar amount of oil extracted as at 60° C. The majority of the oil was extracted within the first 5 min of the extraction process (25° C.-82%; 60° C.-94%), see FIG. 14. Accordingly, best conditions to be used for larger scale extractions is N,N-dimethylcyclohexylamine at 60° C. Increasing the scale 10-fold shows similar results, the extraction time increased slightly to 30 min. The SHS/oil mixture was added to a 10 wt % piperazine solution (relative to SHS). $CO_2$ gas was bubbled through the biphasic solution for about 45 min in order to switch the hydrophobic version of the solvent to its hydrophilic version to extract it from oil into the water phase. The system was allowed to sit for 24 h and the oil was decanted. Analysis of the oil by use of $^1$H NMR spectroscopy techniques showed an SHS content of 11%.

We have shown that the SHS can be used to efficiently to extract soy oil from flaked soy beans. For the soy meal residue to be useful as cow feed and not be a waste product it needs to be free of trace solvents. Thus the following study was conducted.

Amine Removal from Soy Meal

To determine whether the amine could be removed from the soy meal resulting from the oil extraction procedure, dried soy flakes were added to an aqueous 10 wt % piperazine solution. The mixture was stirred and $CO_2$ bubbled through the solution for 3.5 hours. The soy meal was filtered through a J-Cloth™ (a loosely woven cloth made for dishwashing) and was squeezed dry. The soy meal was then rinsed with distilled water and stirred in distilled water for 20 min. The flakes were again filtered through a J-Cloth™ and rinsed a further 3 times with distilled water. The flakes were added to a vial, along with a small amount of d-chloroform and shaken. A $^1$H NMR spectrum using d-chloroform as the solvent was acquired confirming the removal of residual amine on the soy meal after the extraction. This shows that the soy meal can be used as a cattle feed stock after extraction of the soy oil using a switchable hydrophilicity solvent, and that it is not a waste product.

Example 2C

Separation of Bean Oil Using Switchable Hydrophobicity Solvent N1,N1,N4,N4-tetraethylbutane-1,4-diamine N1,N1,N4,N4-tetraethylbutane-1,4-diamine was found to be miscible with soybean oil and can be separated from soybean oil by using carbonated water. It was possible to remove a high percentage of N1,N1,N4,N4-tetraethylbutane-1,4-diamine from the soybean oil be mixing with carbonated water. The percentage removal was 98.65%. In contrast, 96% of BA was removed from the soybean oil. These studies showed that SHS can replace hexane in soybean oil extraction and eliminate energy-intensive distillation thereby having advantages in cost, safety and environmental implications.

Example 3

Polarity study of N,N,N'-tributylpentanamidine (BA)

The maximum wavelength of absorption, $\lambda_{max}$, of a switchable hydrophilicity solvent, N,N,N'-tributylpentanamidine (BA), was analyzed in its hydrophobic and hydrophilic forms using the solvatochromatic dye, Nile Red.

A 1 Dram vial was prepared containing 1 mL of distilled water to which 1 mL of BA was added. The contents were stirred at room temperature for 1 hour. This ensured saturation of the BA phase with water. The top phase comprising the BA liquid was pipetted into a quartz cuvette (Semi-Micro Cells, Self Masking Black Walls Spectrosil® Quartz, Starna Cells, Atascadero, Calif., USA) and 1 mg of Nile Red was added, to provide a bright orange-magenta solution. The ultraviolet absorbance spectrum was acquired on an Agilent Technologies ultraviolet/visible spectrometer 50-60 Hz with UV-Visible Chemstation software. The $\lambda_{max}$ was 510 nm.

Distilled water (1.0 mL) was then added to the quartz cuvette and carbon dioxide was slowly bubbled into the mixture for 1 hour to switch the BA to its ionic form, N,N,N'-tributylpentanamidinium bicarbonate (BAB), after which the homogenous mixture turned purple. The ultraviolet absorbance spectrum of the aqueous solution of the dye and ionic salt was then acquired as discussed in the previous paragraph. The $\lambda_{max}$ was 570 nm.

This polarity study shows that the polarity of BA (hydrophobic form) is significantly lower than that in the aqueous solution of BAB (hydrophilic ionic form). The $\lambda_{max}$ of 510 nm for water saturated BA indicated that it is quite nonpolar, for example exhibiting a polarity between that of diethyl ether and toluene. After switching to the water soluble ionic form, the dramatic increase in $\lambda_{max}$ to 570 nm indicated that it became significantly more polar, for example exhibiting a polarity greater than ethylene glycol.

Example 4

Synthesis of Amidines N,N,N'-tripropylbutyramidine (PA) and N,N,N'-tributylpentanamidine (BA) and amines N1,N1,N4,N4-tetraethylbutane-1,4-diamine and 1,1',1''-(benzene-1,3,5-triyl)tris(N,N-dimethylmethanamine)

The two amidines N,N,N'-tripropylbutyramidine (PA) and N,N,N'-tributylpentanamidine (BA) were synthesized in the following three-step amidine syntheses.

Example 4A

Synthesis of N,N-dibutylpentanamide and N,N-dipropylbutyramide

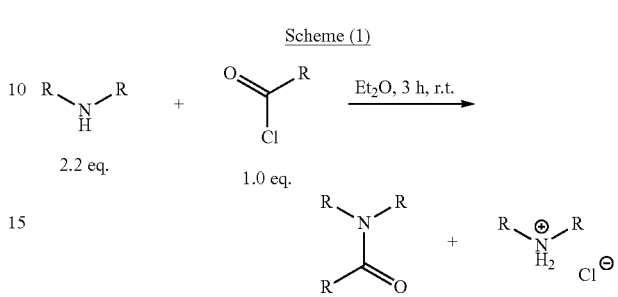

Scheme (1)

N,N-dibutylpentanamide (R=butyl): a round-bottom flask containing a magnetic stirring bar, diethyl ether (400 mL) and N,N-dibutylamine (37 mL, 0.22 mol, 2.2 equiv.) was cooled in ice for 30 minutes. Valeroyl chloride (12.0 mL, 0.099 mol, 1.0 equiv.) was combined with diethyl ether (75 mL) and added dropwise over 30 minutes to the stirring dibutylamine solution on ice. A white precipitate, likely the amine's chloride salt, was observed. The flask was removed from ice and stirred at room temperature for 3 h. Two 500 mL extractions were performed with dilute HCl (10 mL conc. HCl per 500 mL extraction) to remove the excess amine and ammonium chloride byproduct. The diethyl ether layer was retained and dried with $MgSO_4$. Diethyl ether was removed under rotary evaporation and high vacuum, leaving crude N,N-dibutylpentanamide.

Rough characterization was performed on the amide via TLC. A solvent system of hexane:ethyl acetate (80:20 v/v) was prepared. A diethyl ether solution of the product, N,N-dibutylpentanamide, was applied to aluminum-backed alumina TLC plates. The dibutylamine starting material was applied to the plate similarly. The product (amide) appeared with a retention factor of approximately 0.25, while starting material (amine) remained at the origin, as visualized using potassium permanganate solution. If trace amine remained evident in product, it was removed under reduced pressure with stirring at 45° C.

The crude amide was then further characterized by $^1$H NMR spectroscopy before proceeding. N,N-dibutylpentanamide results are presented in Table 1. The isolated yield was, 97%, though typical yields for this reaction range from 94%-99%.

TABLE 1

| $^1$H NMR spectroscopy peak assignments for N,N-dibutylpentanamide | | |
|---|---|---|
| Shift (ppm) | Multiplicity | Integration |
| 3.29 | triplet, $^3J$ = 7.6 Hz | 4.0 (4) |
| 3.20 | triplet $^3J$ = 7.7 Hz | |
| 2.28 | triplet $^3J$ = 7.6 Hz | 1.962 (2) |
| 1.4 | multiplet | 12.49 (12) |
| 0.92 | multiplet | 9.030 (9) |

N,N-dipropylbutyramide: a similar procedure implemented with N,N-dipropylamine (2.2 eq) and butyryl chloride (1.0 eq) results in 95% or higher yield of N,N-dipropylbutyramide (R=propyl). It was characterized by $^1$H NMR spectroscopy a summary of which is presented in Table 2.

TABLE 2

| 1H NMR spectroscopy peak assignments for N,N-dipropylbutyramide | | |
|---|---|---|
| Shift (ppm) | Multiplicity | Integration |
| 3.27 | triplet $^3J$ = 7.7 Hz | 4.0 (4) |
| 3.18 | triplet $^3J$ = 7.7 Hz | |
| 2.27 | triplet $^3J$ = 7.5 Hz | 1.980 (2) |
| 1.6 | multiplet | 6.268 (6) |
| 0.92 | multiplet | 9.036 (9) |

Example 4B

Methylation of N,N-dibutylpentanamide and N,N-dipropylbutyramide

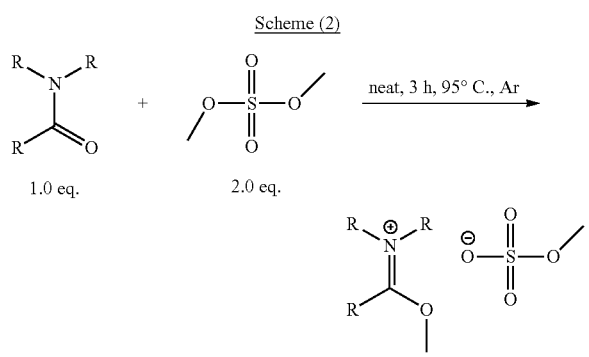

Methylation of N,N-dibutylpentanamide (R=butyl): A round-bottom flask was prepared, containing N,N-dibutylpentanamide (5.0 g, 0.023 mol, 1.0 eq), as synthesized above, and a magnetic stirrer. The flask was fitted to a condenser, flushed with argon and heated to 95° C. Dimethyl sulfate (4.5 mL, 0.046 mol, 2.0 eq.) was added by syringe. The reaction was maintained in the 95° C. oil bath under argon for 3 h. After cooling, two diethyl ether washes, 50 mL each, were performed. The diethyl ether layer took over 30 minutes to become transparent each time and was allowed to clear before diethyl ether was decanted. Residual diethyl ether was evaporated.

Methylation of N,N-dipropylbutyramide (R=propyl): a corresponding procedure was carried out with N,N-dipropylbutyramide (5.0 g, 0.029 mol, 1.0 eq) and identical conditions otherwise.

Example 4C

Amination to N,N,N'-tributylpentanamidine and N,N,N'-tripropylbutyramidine

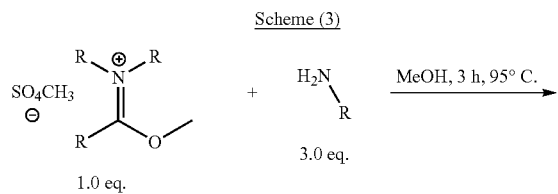

Amination of N,N,N'-tributylpentanamidine (R=butyl): a round-bottom flask was prepared, containing crude methylated N,N-dibutylpentanamide, as synthesized above, and a magnetic stirrer. Butylamine (7.0 mL, 0.070 mol, 3.0 eq) and methanol (40 mL) were added and a condenser was affixed. The flask was heated in a 95° C. oil bath (i.e. at reflux) for 3 h. After cooling, methanol and excess butylamine were removed via rotary evaporation and high vacuum. The residue was dissolved in 100 mL distilled water and acidified with 15 mL concentrated HCl. A diethyl ether wash (100 mL) was performed on the acidic phase to remove residual amide. The aqueous layer was retrieved and basified gradually, using solid KOH, until pH paper indicated a pH>11. A thin organic layer formed on top of the aqueous layer as base was added, presumed to contain amidine, leaving potassium methyl sulfate in the aqueous layer. Diethyl ether (100 mL) was added and dissolved the organic layer. The diethyl ether layer was retained and dried with MgSO$_4$. The diethyl ether was removed via rotary evaporation and high vacuum, leaving crude N,N,N'-tributylpentanamidine.

As the yield in the methylation step was not determined, the isolated yield for consecutive methylation and amination was found instead to be 23%. This value was typical for N,N,N'-tributylpentanamidine synthesis on this scale. The product was characterized by $^1$H NMR, $^{13}$C NMR, electrospray MS and IR spectroscopy.

A $^1$H NMR spectrum was acquired for the sample dissolved in CDCl$_3$ and is shown in FIG. 7A.

A $^{13}$C NMR spectrum was collected in CDCl$_3$ and is shown in FIG. 8A.

An electrospray mass spectrum (positive ion mode) was collected, showing the molecular ion peak (MH$^+$) at m/z=269.041, matching the predicted molecular ion peak for BA.

An infrared spectrum was collected by depositing a drop of neat BA between KBr plates and is shown in FIG. 9A. The strong peak at 1616 cm$^{-1}$ was assigned to the C=N double bond stretch.

Amination of N,N,N'-tripropylbutyramidine (R=propyl): the final step was performed in the parallel manner for N,N,N'-tripropylbutyramidine from its methylation product and propylamine (3.0 eq to initial amide). Isolated yield in consecutive methylation/amination was consistently higher than for N,N,N'-tributylpentanamidine, at 32%. The product was characterized by $^1$H NMR (FIG. 4A), $^{13}$C NMR (FIG. 5A), electrospray MS and IR spectroscopies (FIG. 6A), in the same manner as BA.

An electrospray mass spectrum (positive ion mode) was collected, showing the molecular ion peak (MH$^+$) at m/z=213.027, matching the predicted molecular ion peak for PA.

An infrared spectrum (FIG. 6A) was collected by depositing a drop of neat PA between KBr plates. The strong peak at 1616 cm$^{-1}$ was assigned to the C=N double bond stretch.

Example 4D

Synthesis of N1,N1,N4,N4-tetraethylbutane-1,4-diamine, N,N'-dipropyl-N,N'-diethylbutane-1,4-diamine and N,N,N',N'-tetrapropylbutane-1,4-diamine N1,N1,N4,N4-tetraethylbutane-1,4-diamine synthesis

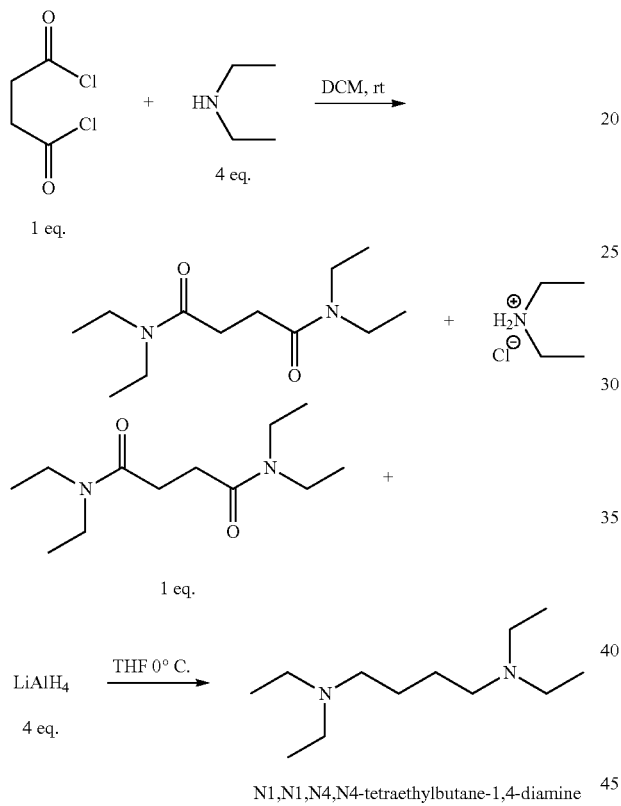

N1,N1,N4,N4-tetraethylbutane-1,4-diamine

N1,N1,N4,N4-tetraethylbutane-1,4-diamine product was synthesized by the reaction of succinyl chloride (1 eq.) and diethylamine (4 eq.) followed by the reduction of diamide with LiAlH$_4$. A round bottom flask containing dichloromethane ("DCM") (100 mL) and diethylamine (26.4 g, 35.3 mL, 0.361 mol) was maintained under argon atmosphere and cooled in an ice bath for 15 min. Succinyl dichloride (12.7 g, 9.2 mL, 0.082 mol) was added dropwise as the reaction was exothermic. The reaction mixture was stirred at room temperature for 3-4 h. The diamide was isolated by adding concentrated HCl (5 mL) and water (150 mL) to separate the ammonium salt and unreacted diethylamine in the aqueous layer. Dichloromethane was dried using anhydrous MgSO$_4$ and was evaporated under reduced pressure using a rotary evaporator to obtain the diamide. The product was characterized by $^1$H and $^{13}$C NMR.

In the second step, LiAlH$_4$ (159 mL of 2 M solution in tetrahydrofuran (THF)) was added dropwise to the solution of diamide (16.5 g in 50 mL of dry THF) and maintained at 0° C. under an argon atmosphere. The reaction mixture was refluxed over an oil bath and maintained at 70° C. for 6 h. The extraction of the product from the mixture was performed by quenching the LiAlH$_4$. In the quenching procedure, for each gram of LiAlH$_4$, 1 ml of water was added followed by 1 ml of 15% sodium hydroxide and 5 mL of water.[5] Then, more THF (100 mL) was added to the mixture. If necessary, the reaction mixture was sonicated for 5 min. The reaction mixture was filtered. The filtrate and washings (30 mL of THF) were passed through MgSO$_4$. THF was removed under reduced pressure to obtain N1,N1,N4,N4-tetraethylbutane-1,4-diamine (yield 89%). The product was characterized by $^1$H and $^{13}$C NMR spectroscopy and also by high resolution mass spectroscopy.

Compounds N,N'-dipropyl-N,N'-diethylbutane-1,4-diamine and N,N,N',N'-tetrapropylbutane-1,4-diamine were made in a similar manner, but using ethylpropylamine or dipropylamine instead of diethylamine to make the diamide.

Example 4E

Synthesis of 1,1',1''-(benzene-1,3,5-triyl)tris(N,N-dimethylmethanamine)

1,1',1''-(benzene-1,3,5-triyl)tris(N,N-dimethylmethanamine) synthesis

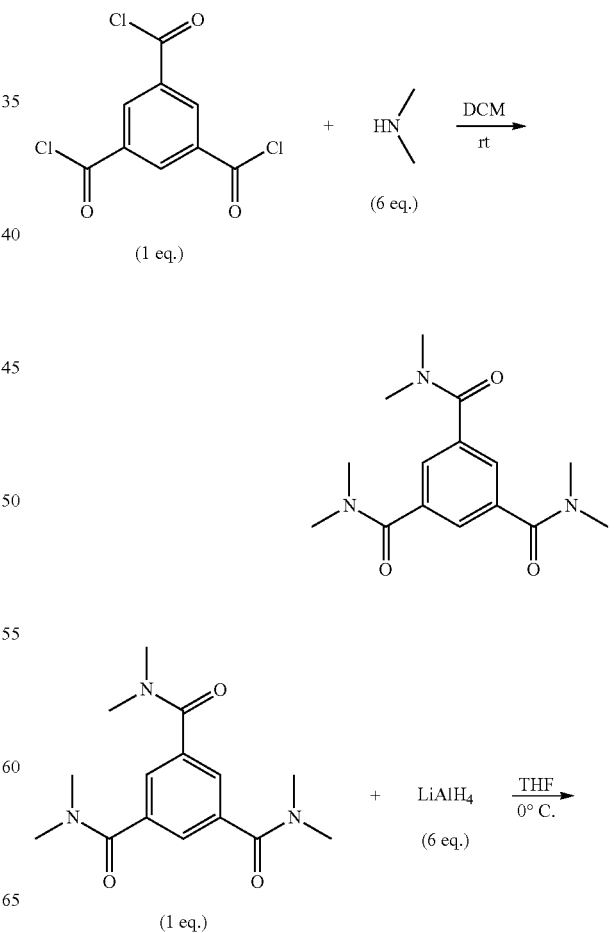

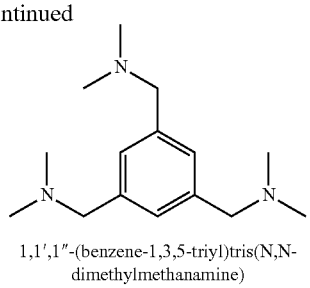

1,1',1"-(benzene-1,3,5-triyl)tris(N,N-dimethylmethanamine)

Triamine 1,1',1"-(benzene-1,3,5-triyl)tris(N,N-dimethylmethanamine) was synthesized in two steps. The first step of this reaction involved a nucleophilic substitution of acyl chloride atoms with nucleophilic nitrogen of dimethylamine. In a round bottom flask, containing a magnetic stir bar, dichloromethane (100 mL) and dimethylamine (54 mL of 2.0 M solution in THF), were cooled over an ice bath for 15 minutes and acid chloride (5.0 g, 3.36 mL, 0.018 mol) was added dropwise. The mixture was stirred overnight at room temperature and a light green solution was obtained. The reaction mixture was evaporated under reduced pressure, to yield a yellow solid. Water (100 mL) was added to this solid to obtain a clear solution. KOH (3.329 g in 6 mL of water) was added to this solution. The resulting solution included an inorganic salt (KCl), water and $NH(CH_3)_2$. Water was evaporated under reduced pressure to yield a solid. Methanol (100 mL) was used as solvent to dissolve the triamide, while inorganic salt (KCl) remained mostly undissolved. The methanolic solution was filtered to separate KCl and evaporated under reduced pressure to yield the triamide. The product was characterized by $^1H$ and $^{13}C$ NMR spectroscopy.

In the second step, $LiAlH_4$ (75.3 mL of 2M solution in THF) was added drop wise to the solution of triamide (6.64 g, 0.0228 mol in 50 mL of dry THF), and maintained at 0° C. under an argon atmosphere. The mixture was refluxed over an oil bath at 70° C. for 6 h after which, no hydrogen evolution was apparent and the reaction mixture became viscous. The separation of the product from the mixture was performed by first quenching $LiAlH_4$. In this quenching method, for each gram of $LiAlH_4$, 1 mL of water was added followed by 1 mL of a sodium hydroxide solution (15%) followed by 5 mL of water.[5] More THF (100 mL) was added and the mixture was sonicated for 15 minutes. The product (in THF) was obtained by filtering this solution to separate it from the white precipitate (oxide/hydroxide of Al). The THF solution (filtrate containing the desired amine) along with the washings (3×30 mL) were dried over anhydrous $MgSO_4$ and evaporated under reduced pressure over a rotary evaporator to obtain the desired 1,1',1"-(benzene-1,3,5-triyl)tris(N,N-dimethylmethanamine) (yield 99%). The product was characterized by $^1H$ and $^{13}C$ NMR spectroscopy and also by high resolution mass spectrometry.

Example 5

Evaluation of the Ability of Amines to Serve as Switchable Hydrophilicity Solvents Example 5A Evaluation of the Miscibility of Amines with Water in the Absence of $CO_2$ 1 mL of an appropriate amine was combined with 1 mL of $H_2O$ in a 4 mL vial, with the 1 and 2 mL volume lines marked.

The vial was manually shaken and left to settle at room temperature. After the mixture settled, the number of phases was observed visually. This procedure was performed for all of the screened amines.

The following amines formed a biphasic mixture with water under air:
triethylamine,
N-ethylpiperidine,
N,N-dimethylcyclohexylamine,
N,N-dimethylhexylamine,
N,N-dimethylbutylamine,
N,N-diethylbutylamine,
methyldipropylamine,
N-butylpyrrolidine,
trioctylamine,
tripropylamine,
N,N-dimethyldodecylamine,
N,N-diisopropylethylamine,
N,N-dimethylaniline,
N1,N1,N4,N4-tetraethylbutane-1,4-diamine,
1,1',1"-(benzene-1,3,5-triyl)tris(N,N-dimethylmethanamine,
1,1',1"-(cyclohexane-1,3,5-triyl)tris(N,N-dimethylmethanamine,
N,N'-dipropyl-N,N'-diethylbutane-1,4-diamine,
N,N,N',N'-tetrapropylbutane-1,4-diamine.

The following amines formed a single-phase liquid mixture with water under air: triethanolamine, N-ethylmorpholine, N-methylpiperidine, N,N,N',N',-tetramethylethylenediamine. These water-miscible amines were not subjected to further experimentation.

Example 5B

Evaluation of the Miscibility of Amines with Water in the Presence of $CO_2$

All of the amines that formed a biphasic mixture in Example 5A were subjected to the following test. Carbon dioxide was bubbled through the amine/water biphasic mixture, via a syringe needle, for at least one hour. Care was taken to regulate the rate of the $CO_2$ bubbling, so as not to cause evaporation of the amine. The liquid-liquid interface was observed over the course of $CO_2$ bubbling, and a photo was taken after 60 minutes.

The following amines formed a single-phase liquid mixture with water after the $CO_2$ treatment:
triethylamine,
N-ethylpiperidine,
N,N-dimethylcyclohexylamine,
N,N-dimethylhexylamine,
N,N-dimethylbutylamine,
N,N-diethylbutylamine,
methyldipropylamine,
N-butylpyrrolidine,
1,1',1"-(benzene-1,3,5-triyl)tris(N,N-dimethylmethanamine,
1,1',1"-(cyclohexane-1,3,5-triyl)tris(N,N-dimethylmethanamine,
N,N'-dipropyl-N,N'-diethylbutane-1,4-diamine,
N1,N1,N4,N4-tetraethylbutane-1,4-diamine.

These amines are considered switchable hydrophilicity solvents.

The following amines formed a biphasic mixture with water after the $CO_2$ treatment:
trioctylamine,
tripropylamine, N,N-dimethyldodecylamine,
N,N-diisopropylethylamine,
N,N',N'-tetrapropylbutane-1,4-diamine, and
N,N-dimethylaniline.
These amines were rejected and not subjected to further experimentation.

Example 5C

Testing of the Conversion of the Amine Switchable Hydrophilicity Solvents Back to their Hydrophobic Forms All of the amines identified as switchable hydrophilicity solvents in Example 5B (except N,N-dimethylbutylamine) were subjected to the following test. The vial containing the single-phase amine/water/$CO_2$ mixture prepared in example 5B was heated in an oil bath at 80° C. for approximately 60 minutes. The mixture was magnetically stirred, and phase separation was observed throughout the course of heating. In the case of the N1,N1,N4,N4-tetraethylbutane-1,4-diamine/water/$CO_2$ mixture, 5 hours of heating was required to switch it back to its hydrophobic form.

The following amines exhibited loss of amine during this procedure, presumably due to excessive volatility: triethylamine, N,N-diethylbutylamine, methyldipropylamine. In some applications, this volatility may be undesired.

Example 5D

Converting an Ammonium Bicarbonate Salt to its Corresponding Amine by Bubbling Air at Room Temperature A homogeneous aqueous solution of dimethylcyclohexylammonium bicarbonate was prepared by mixing N,N-dimethylcyclohexylamine (1 mL), and $H_2O$ (1 mL) and bubbling with $CO_2$ for 90 minutes. The 2.0 mL solution was placed in a 10 mL graduated cylinder with a magnetic stir bar and that was then stoppered with a rubber septum. Air was bubbled through the solution for a total of 28 hours, with constant stirring. After 8 hours, there was no observed phase separation or volume loss. After an additional 20 hours, a two-phase liquid mixture was observed; its bottom layer was transparent and colorless, with a volume of 1.6 mL, and its top layer was clear and slightly oily, with a volume of 0.3 mL. Total volume loss after 28 hours was 0.1 mL.

Example 6

NMR Spectroscopy of Amine Switchable Hydrophilicity Solvents

The following amines were evaluated in this series of experiments: N-ethylpiperidine, N,N-dimethylcyclohexylamine, and N,N-dimethylhexylamine. The sequence of experiments is described for one amine but was performed for all three. The visual observations are described in Table 3. 1,4-Dioxane was used as an internal standard for NMR spectroscopy.

Amine (1 mL) was combined with $D_2O$ (1 mL) in a 10 mL graduated cylinder, which was then capped with a rubber septum. The cylinder was manually shaken and left to settle at room temperature, after which the mixture appeared as two transparent liquid phases. For each amine, this procedure was simultaneously conducted in 3 identical cylinders. From the aqueous (bottom) layer of one of the three cylinders, three 250 µL samples were withdrawn, combined with equal volumes of $D_2O$ and dioxane internal standard, and analyzed by $^1H$ NMR spectroscopy. The spectra were consistent with the amine in the aqueous phase being in its neutral form. The graduated cylinder from which the samples were taken was discarded.

For each of two remaining graduated cylinders, carbon dioxide was bubbled through the amine/water biphasic mixture, via a syringe needle, for at least one hour. Care was taken to regulate the rate of the $CO_2$ bubbling, so as not to cause significant evaporation of the amine. The mixture changed from a biphasic liquid mixture to a single homogeneous liquid phase. From one of the two graduated cylinders, a 300 µL sample of the homogenous liquid phase was withdrawn and mixed with an equal volume of $D_2O$ and a known quantity of dioxane internal standard. The $^1H$ NMR spectrum of the mixture showed a shift in the proton signals, which suggested that the amine had switched to its protonated, bicarbonate salt form. The graduated cylinder from which the sample was taken was discarded.

The remaining graduated cylinder, containing the single-phase amine/water/$CO_2$ mixture prepared above, was heated in an oil bath at 80 deg. C for 1 hour. Phase separation was observed. Three 250 µL samples of the aqueous (bottom) layer were withdrawn, combined with equal volumes of $D_2O$ and a known quantity of dioxane internal standard, and analyzed by NMR spectroscopy.

TABLE 3

| | Observations for Example 6 | | |
|---|---|---|---|
| | Without $CO_2$ | After $CO_2$ bubbling | After heating |
| N-ethyl-piperidine | formed 2 layers; bottom is clear & colorless, top is clear & pale yellow, both with volumes of 1 mL | took 60 min to form one clear, pale yellow homogeneous solution. total volume is 1.9 mL (loss of 0.1 mL) | after 30 min, separated into 2 layers; bottom is clear, pale orange, with volume of 1 mL, and top is clear yellow, with volume of 0.7 mL. NMR spectroscopy showed that approximately 49% of the amine remained in the aqueous phase |
| N,N-dimethyl-N-cyclohexylamine | formed 2 clear, colorless layers, each with 1 mL total volume | took 45 min to form one clear, colorless homogenous solution. no apparent loss of volume | after 30 min, solution has separated into 2 layers; bottom is clear & colorless, with volume of 1 mL, and top is colorless & slightly oily, with volume of 0.8 mL |

TABLE 3-continued

Observations for Example 6

| | Without $CO_2$ | After $CO_2$ bubbling | After heating |
|---|---|---|---|
| N,N-dimethyl-N-hexylamine | formed 2 clear, colorless layers, each with 1 mL total volume | took 75 min to form one clear, colorless homogeneous solution. total volume is 1.9 mL (loss of 0.1 mL) | after 30 min solution has separated into 2 clear, colorless layers, bottom is 1 mL, top is 0.9 mL. . NMR spectroscopy showed that approximately 6% of the amine remained in the aqueous phase. |

Example 7

Extraction of Motor Oil from Shredded Plastic Bottles

When plastic bottles of motor oil (vehicle engine lubricant) are discarded, they contain a significant amount of residual oil. Some such bottles are made of polyethylene. Current practices of shredding the used bottles into plastic chips for recycling results in oil-coated plastic chips. Because the oil sticks to the plastic, if the chips are washed with water, oil remains on the plastic chips. If surfactant is added to, water to wash the chips, separating the water and oil becomes difficult and energy intensive. Studies were conducted to evaluate the ability of switchable hydrophilicity solvents to separate residual oil from such plastic chips.

Carbonated water was prepared by bubbling $CO_2$ through distilled water for at least 30 min.

Oil-coated plastic (e.g., polyethylene) chips (70 g) (approximately 1 inch diameter) that were obtained from NPI (NexCycle Plastics Inc.) of Brampton, Ontario, Canada, were placed into a 1 L vessel with a large magnetic stir bar. N,N-dimethyl-N-cyclohexylamine (210 mL) was added and a lid was placed on the vessel. The contents were stirred for 0.5 h, allowed to sit overnight (~16 h), and then stirred again for 1 h. The plastic chips were separated by filtration from homogeneous reddish-brown filtrate (a liquid mixture comprising N,N-dimethylcyclohexylamine and oil). The plastic chips were washed with carbonated water (300 mL×2) and distilled water (300 mL×1). The washed plastic chips were left to air-dry resulting in clean, dry plastic chips. Combined washings were added to the filtrate to form a two-layer liquid mixture. As described herein, exposure of N,N-dimethylcyclohexylamine to $CO_2$ in the presence of water leads to formation of its corresponding ammonium salt. The two-layer liquid mixture has an aqueous layer comprising water, $CO_2$, and some ammonium salt and a hydrophobic layer comprising N,N-dimethylcyclohexylamine and oil. $CO_2$ gas was bubbled through the filtrate liquid mixture with low agitation to minimize formation of foam. When the amine was protonated it partitioned out of the hydrophobic layer and into the aqueous layer. After bubbling for several hours the hydrophobic layer comprised the brown motor oil (7 mL) and only a small amount of residual amine as shown by NMR. The motor oil was decanted and washed with carbonated water to remove any residual amine. Washings were not combined with the aqueous layer of the decanted mixture. The aqueous layer was then treated to a trigger to switch the N,N-dimethylcyclohexyl-ammonium bicarbonate back to its neutral hydrophobic form. Triggers that were used included heating to 80° C. (to expel $CO_2$) in the absence of a flushing gas, and heating to 35° C. while aerating using compressed air. (Aerating with air at room temperature was not effective in this situation.) Conversion of a substantial portion of the dimethylcyclohexylammonium bicarbonate to N,N-dimethylcyclohexylamine was confirmed by visual inspection (one aqueous homogeneous solution became two-layers) and by NMR. N,N-dimethylcyclohexylamine, was decanted from the aqueous layer and was collected for reuse in this process.

In another study, oil coated plastic chips (~100 g) were placed in a 1 L vessel, a first washing was performed by adding N,N-dimethylcyclohexylamine (300 mL). The vessel was sealed and its contents were shaken for 1 minute. The shaking resulted in plastic chips interspersed in a liquid mixture of N,N-dimethylcyclohexylamine and dissolved oil. The liquid mixture was then decanted off from the solid plastic chips. The chips were then subjected to a second washing by adding fresh N,N-dimethylcyclohexyl-amine (50 mL) to the vessel housing the plastic chips and shaking for approximately 10 seconds. This shaking resulted in a liquid mixture and plastic chips. The liquid mixture from the second washing was isolated and added to the liquid mixture from the first washing. The chips were subjected to a third and a fourth washing by repeating the procedure using fresh N,N-dimethylcyclohexylamine (30 mL×2). All of the washings (410 mL of N,N-dimethylcyclohexylamine plus a certain volume of dissolved oil), were then combined with approximately 1000 mL of water. This combination appeared as a two layer liquid mixture, where one layer was an aqueous phase, which included the water, and the other layer was a hydrophobic phase, which included the N,N-dimethylcyclohexylamine and the dissolved oil. At this point it was desirable to switch the N,N-dimethylcyclohexylamine to its hydrophilic protonated form, thereby making it have a hydrophilicity sufficient to migrate away from the hydrophobic phase and into the aqueous phase. Accordingly, the two layer liquid mixture was bubbled for 1-2 hours with $CO_2$. During the bubbling, it was visually observable that the volume of the hydrophobic phase decreased. After the bubbling, a two layer liquid mixture was still observed; however, the hydrophobic layer of the two layer liquid mixture now was merely comprised of motor oil and a small amount of residual N,N-dimethylcyclohexylamine solvent, as verified by $^1H$ NMR spectroscopy. The hydrophobic phase comprising motor oil was decanted to isolate it from the aqueous phase.

It was then desirable to make the aqueous phase, which appeared as a single layer liquid mixture and which comprised water and the protonated form of N,N-dimethylcyclohexylamine, into a two phase liquid mixture with an aqueous phase, which is water, and a hydrophobic phase, which is N,N-dimethylcyclohexylamine. Accordingly, the aqueous layer, which comprised water and the protonated form of N,N-dimethylcyclohexylamine, was then bubbled using compressed air and was heated to about 50 degrees Celcius for several hours until the solvent has returned to its hydrophobic form.

The plastic chips that had undergone five washings as described above were subsequently washed with pre-carbonated water (3×500 mL) and water (5×500 mL). The washed plastic chips were dried by blowing compressed air over the chips for several hours followed by allowing them to air dry.

Example 8

Making Higher Density Polystyrene from Polystyrene Foam

Recycling of polystyrene foam is problematic because of its very low density which makes shipping it expensive. Shipping and recycling would be less expensive if it could be converted into a high density form. Studies were conducted that determined that switchable hydrophilicity solvents could be used to perform this conversion.

Polystyrene foam packing material (e.g., STYROFOAM™) chunks (2 g) were dissolved in 20 mL of N,N-dimethylcyclohexylamine to make a viscous 10 wt % liquid mixture. Carbonated water was prepared in a separate vessel by vigorously bubbling distilled water with $CO_2$ for 30 minutes, and the $CO_2$ bubbling and vigorous stirring were continued during the experiment. The viscous mixture was then manually into carbonated water (200 mL) injected using a small bore needle. This addition was done slowly (over approximately 40 min) with vigorous stirring (for high shear) to avoid producing large clumps of polystyrene with trapped amine, but rather to produce strings of polystyrene with little to no trapped amine. This addition was performed slowly to allow the N,N-dimethylcyclohexylamine to react with the carbonated water to form its salt form, the salt form being water-soluble. Upon addition of the mixture to the carbonated water, polystyrene thread-like strands were produced while a substantial portion of the N,N-dimethylcyclohexylamine reacted with the carbonated water to form its corresponding water-soluble bicarbonate salt. The polystyrene strands were collected by filtration, washed with carbonated water and air dried. In these initial studies, small amounts of N,N-dimethylcyclohexylamine (up to 10%) were attached to the polystyrene strands, as shown by NMR. Optimization of the precipitation process is expected to reduce the amount of attached amine, for example, use of an extruder would provide appropriate temperatures to drive off residual amine and water. Using the above-described process, the volume of 2 g of expanded polystyrene foam was decreased from 140 $cm^3$ to 2 $cm^3$ of dense polystyrene. This method has also successfully performed using a 40 wt % liquid mixture of polystyrene foam in N,N-dimethylcyclohexylamine.

Example 9

Extraction of Bitumen from Oil Sands

In a fumehood, a sample of oil sands (13.68 g) (obtained from Syncrude Canada Ltd., Fort McMurray, Alberta, Canada) was placed into a tared 250 mL beaker with a cross-shaped stir bar. N,N-Dimethylcyclohexylamine (35 mL, 27.36 g, 0.849 g/mL, 2 g per g of oil sands) was measured in a 100 mL graduated cylinder and added to the oil sands in the beaker inside the fumehood. A stir plate was placed under the beaker, turned on and set at 200 rpm. The solution was stirred for an hour. The stir plate was turned off and the stir bar was removed from the mixture. The solution was vacuum filtered using a ceramic Büchner funnel with a filter paper (Fisher Scientific, diameter 9.0 cm). Solids captured in the filter were washed with N,N-dimethylcyclohexylamine (10 mL) and vacuum was continued for an hour. After the vacuum was turned off, the solids were removed from the filter and placed into a clean, tared 250 mL beaker. The mass of the solids was recorded (11.74 g).

In order to ensure the maximum removal of bitumen from the oil sands, the washing procedure was repeated. Using a 100 mL graduated cylinder, N,N-dimethylcyclohexylamine (27 mL) was measured and added to the solids in the beaker in a fumehood. The beaker was placed on the stir plate and a cross-shaped stir bar was placed in the beaker. The stir plate was turned on and set at 200 rpm. The solution was stirred for an hour. The stir plate was turned off and the stir bar was removed from the solution. The mixture was vacuum filtered using a Büchner funnel. The captured solids were washed with N,N-dimethylcyclohexylamine (10 mL) and the vacuum was continued for an hour. After the vacuum was turned off, the solids were removed from the filter and placed into a clean, tared 250 mL beaker. The mass of the sand was recorded (11.56 g).

Extraction of Residual Oil from the Cleaned Oil Sands Solids

In a fumehood, using a 100 mL graduated cylinder, toluene (30 mL) was measured and then added to the beaker containing the washed solids from the above procedure. The beaker was placed onto a stir plate and a cross-shaped stir bar was added. The mixture was stirred at 150 rpm for one hour. The stir plate was turned off and the stir bar was removed from the mixture. The mixture was vacuum filtered using a Büchner funnel, washed with toluene (10 mL) and the vacuum was continued for an hour. After the vacuum was turned off, the solids were removed from the filter and placed into a clean, tared 30 mL vial. The mass of the sand was recorded (15.26 g).

The toluene solution was placed into a 100 mL round bottom flask and attached to a rotary evaporator. The toluene was removed by rotary evaporation, after which the flask contained only an oily residue having a mass of 18.2 mg. We therefore conclude that the oil sands solids, after the two washes with dimethylcyclohexylamine, contained only 18.2 mg of bitumen.

Extraction of Amine from Oil

Based on the total amount of amine (82 mL, 69.92 g, 0.849 g/mL) used to wash the oil, a similar amount of distilled water (70 mL) was measured into a 100 mL graduated cylinder and placed into a 250 mL Erlenmeyer flask. In a fumehood, the flask was secured to a retort stand and a gas dispersion tube (available as model number 7202-20 from Ace Glass of Vineland, N.J., USA) was placed into the flask. The water was carbonated by bubbling carbon dioxide through the dispersion tube for an hour at a flow rate of approximately 500 mL/min. A separatory funnel ring was attached to a retort stand in the fumehood. The carbonated water was added to a tared 500 mL separatory funnel. The amine/oil solution from the oil sands extraction was also added to the separatory funnel. The dispersion tube was then placed into the separatory funnel and carbon dioxide was bubbled through the solution until the separated oil was visibly thick and stuck to the sides of the separatory funnel. The aqueous phase (lower layer) was then released into a tared 250 mL Erlenmeyer flask. The oil was allowed to sit in the separatory funnel overnight. Any amine/water that separated overnight was then released into the same flask the next day.

The separatory funnel was then washed with toluene so that all of the oil was dissolved into the toluene. The toluene solution was then emptied from the separatory funnel into a tarred 250 mL round bottom flask. The round bottom flask was then placed on a rotary evaporator and the toluene was evaporated off of the oil. The mass of the residual oil was then recorded (1.94 g).

Separation of Amine from Aqueous Phase

Distilled water (900 mL) was added to a 1000 mL beaker and placed on a stir plate. A cross-shaped stir bar was added to the water. The stir plate was set to heat to a temperature of 60° C. and to stir at 250 rpm. This assembly served as a hot water bath. Using a clamp, the Erlenmeyer flask containing the aqueous phase from the previous procedure was set in the hot water bath and secured to the retort stand. A dispersion tube was placed into the solution and nitrogen gas was bubbled through the solution at a flow rate of approximately 500 mL/min. After some time, the liquid contents separated into two liquid phases, the upper (organic) phase was yellow. The lower (aqueous) phase was also initially yellow. The solution was kept in the bath at 60° C. and bubbled with nitrogen until the lower phase became colourless, after which the stir plate and nitrogen were turned off. The flask was taken out of the hot water bath and allowed to cool to room temperature and to sit overnight. The amine phase (top layer) was pipetted off into a clean, tared 250 mL beaker. Recovered amounts of amine (48.64 g, 70% of the original amount) and the aqueous phase (77.49 g, 111% of the original amount of water) were recorded. Thus, over half of the amine was recovered and some of the amine clearly remained in the water (this is evident because the mass of the aqueous phase was greater than the original mass of water used).

Example 10

Extraction of Oil from a Contaminated Rock Sample from Drilling Fines

A contaminated rock sample of "cuttings" or drilling fines was obtained from Newalta (of Calgary, Alberta, Canada, but this sample originated from an offshore drilling site near Nova Scotia, Canada, where such samples are currently transported to mainland and treated in ponds using microbes). Drilling fines samples were cleaned using hexanes, and using switchable hydrophilicity solvent. Prior to treatment, the drilling fines appeared as a wet thick mud that clung to the sides of its vessel quite resembling peanut butter. The resultant products of both treatments appeared the same and were transparent light yellow liquid and clumps of dry dirt that were lightly packed into glass tubes with air pockets appearing in between the clumps. Although the products were substantially the same, the techniques were different. The hexanes method required that the solvent be distilled; in contrast, the SHS method required no distillation.

Hexanes Method

In a 250 mL beaker, a sample of contaminated rock (25 g) was stirred into 100 mL of hexanes for 0.5 h. The mixture was vacuum filtered using a Büchner funnel and the clean rock sample was air-dried over night. The resulting filtrate was filtered through a Celite bed to remove fine particles. The clean filtrate was then placed on a rotary evaporator to remove the hexanes. This resulted in a clear, yellow oil, corresponding to 19 wt % of the original rock sample.

SHS Method

In a 60 mL jar, a sample of contaminated rock (5.0 g) was stirred (400 rpm) with 30 mL of N,N-dimethylcyclohexylamine for 0.5 h. The resulting mixture was vacuum filtered using a Büchner funnel having 4 layers of filter paper, followed by filtering through a small bed of Celite, to remove any fine particles. The isolated clean rock sample was air-dried over night. The resulting amine/fluid mixture was combined with 60 mL of 2 M aqueous $(NH_4)_2SO_4$ containing 10 wt % piperazine (with respect to the amine) in a 150 mL graduated jar and bubbled with $CO_2$ (500 mL/min), using a fritted dispersion tube (145-175 µm porosity), for 0.5 h, with stirring. This resulted in 0.86 g of a clear, yellow oil that corresponds to 17 wt % of the original sample.

Example 11

Extraction of an Odorous Compound from Plastic

Odorous plastic chips were received from Entropex (Sarnia, Ontario, Canada). The plastic chips were made from shredded plastic bottles. The bottles previously stored cleaners and detergents. The source of the odour was believed to be limonene.

In a 1 L jar, 400 g of odorous plastic chips were washed with 100 mL of dimethylcyclohexylamine for 1 min. The chips were filtered through Celite and washed with an additional 50 mL of dimethylcyclohexylamine. Following this the chips were washed with 200 mL of carbonated water and 1 L of distilled water. The resulting chips were placed on paper towel and air-dried.

In preliminary studies the percentage removal of the odorous compound(s) was not quantified. However, it is noted that prior to treatment for removal of the odorous compounds, exposure to the odorous plastic chips caused one experimenter to have a headache that lasted for the remainder of the day and evening, while after treatment for removal of the odorous compound(s), the same experimenter could perceive no odour, and no headache was experienced.

In this study it was found that the SHS could be used several times before the organic contaminants needed to be removed from the solvent. The process of removing the contaminants was as described for prior examples (see FIG. 16). Briefly, the contaminated solvent was combined with water and exposed to $CO_2$. After exposure to $CO_2$ in the presence of water, the SHS migrated into the aqueous phase while the organic contaminant(s) remained insoluble and were then isolated by filtration or decantation. The aqueous phase was then exposed to air and heated slightly to remove dissolved $CO_2$ and was reused for more washing.

Example 12

Addition of Dye to Textile

Switchable hydrophilicity solvents are useful in dyeing of textiles (see FIG. 20). A dye is added to and solubilized in a hydrophobic-form liquid SHS. Initially, the dye preferentially remains solubilized in the hydrophobic solvent, relative to adhering to the textile. Then, an aqueous solution is added to the solvent and a two layer liquid mixture is formed. Optionally, the aqueous solution is pre-carbonated (i.e, includes dissolved $CO_2$). The dye stays in the hydrophobic layer of the two layer mixture. In the situation where the aqueous solution is not pre-carbonated, $CO_2$ is bubbled through the aqueous liquid mixture. Under these conditions, and under the conditions of the aqueous solution being pre-carbonated, the SHS protonates and migrates to the aqueous layer of the mixture. The dye is not solubilized by the aqueous layer and has little to no hydrophobic solvent remaining. Accordingly, the dye becomes more and more insoluble and accordingly adheres to the textile. Textile and its adhered dye can be removed from the aqueous liquid and further processed (e.g, dried).

It will be understood by those skilled in the art that this description is made with reference to the preferred embodiments and that it is possible to make other embodiments employing the principles of the invention which fall within its spirit and scope as defined by the claims appended hereto.

We claim:

1. A composition comprising:
   water or an aqueous liquid;
   dissolved $CO_2$ from a source other than air; and
   a switchable hydrophilicity solvent (SHS) that is an amine, wherein the SHS reversibly interconverts from a water-miscible, protonated form to a water-immiscible, liquid, unprotonated form when the amount of the dissolved $CO_2$ is insufficient to maintain the protonated form of the SHS;
   wherein the dissolved $CO_2$ can be removed by exposing the composition to (i) heat, (ii) a flushing gas, (iii) reduced pressure, or (iv) any combination thereof.

2. The composition of claim 1, wherein the aqueous liquid comprises salty water.

3. The composition of claim 1, wherein exposing to heat is heating to about 60° C.

4. The composition of claim 1, wherein the SHS comprises a compound of formula (10)

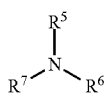
(10)

that is water-immiscible;
where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof;
with the proviso that at least one of $R^5$, $R^6$, and $R^7$ is not H.

5. The composition of claim 1, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

6. A method for separating a selected substance from a mixture, comprising:
   adding a water-immiscible compound of formula (10) that is in a liquid state to a mixture comprising a selected substance that is water-immiscible,
   allowing the compound to solubilize the selected substance;
   optionally isolating waste solid(s) from the mixture;
   contacting the mixture with water and $CO_2$ thereby converting the compound to a salt and forming a composition according to claim 1;
   allowing the mixture to separate into two distinct phases; and
   separating the two distinct phases to provide an isolated aqueous phase comprising the salt and an isolated non-aqueous phase comprising the selected substance;
   wherein the selected substance is not reactive with the compound, $CO_2$, or a combination thereof;
   wherein the compound of formula (10) is:

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n +m is a number from 1 to 10; a substituted or unsubstituted $0_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof; with the proviso that at least one of $R^5$, $R^6$, and $R^7$ is not H.

7. The method of claim 6, further comprising:
   removing $CO_2$ from the isolated aqueous phase to reform the water-immiscible compound of formula (10); and
   isolating the compound.

8. The method of claim 7, wherein removing $CO_2$ comprises:
   heating the isolated aqueous phase;
   placing the isolated aqueous phase under reduced pressure;
   contacting the isolated aqueous phase with a nonreactive gas that contains substantially no $CO_2$; or
   both heating and contacting the isolated aqueous phase with a nonreactive gas that contains substantially no $CO_2$.

9. A method for converting a salt to a water-immiscible liquid comprising:
   providing the composition of claim 1, wherein said protonated form of the SHS is a salt of formula (20)

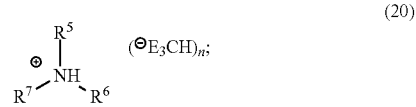

removing $CO_2$ from the composition to form a mixture comprising water and a water-immiscible compound of formula (10)

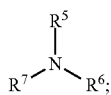  (10)

allowing the mixture to separate into two distinct phases; and isolating an aqueous phase and a non-aqueous phase comprising the compound of formula (10);

wherein for formula (10) and formula (20): $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n + m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;

with the proviso that at least one of $R^5$, $R^6$, and $R^7$ is not H; and wherein n is a number from 1 to 6 sufficient to balance the overall charge of the ammonium cation, and E is O.

10. The method of claim 9, wherein removing $CO_2$ comprises:

heating the composition;

placing the composition under reduced pressure;

contacting the composition with a nonreactive gas that contains substantially no $CO_2$;

both heating the composition and contacting the composition with a nonreactive gas that contains substantially no $CO_2$; or both heating the composition and placing the composition under reduced pressure.

11. The method of claim 7, wherein $CO_2$ is removed by contacting with a gas that contains substantially no $CO_2$, $CS_2$, or COS.

12. A method of extracting a hydrophobic material from a solid that is at least partially coated by the hydrophobic material, comprising:

combining a solid that is at least partially coated by a hydrophobic material and a solvent comprising a water-immiscible compound of formula (10) to form a mixture of the solid in a homogeneous single-phase liquid, said liquid comprising the compound and the hydrophobic material

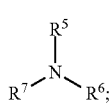  (10)

separating the solid from the single-phase liquid; and combining in any order the single-phase liquid, water, and $CO_2$ to form a two-phase liquid mixture wherein a first phase is hydrophobic and comprises the hydrophobic material and a second aqueous phase is a composition as defined in claim 1 and comprises water and a water-soluble or water-miscible bicarbonate salt of formula (20)

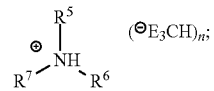  (20)

wherein for formula (10) and formula (20):

$R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n + m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;

with the proviso that at least one of $R^5$, $R^6$, and $R^7$ is not H; and wherein n is a number from 1 to 6 sufficient to balance the overall charge of the ammonium cation, and E is O.

13. The method of claim 12, wherein the hydrophobic material is soluble or miscible in a compound of formula (10), but is not soluble nor miscible in a compound of formula (20).

14. The method of claim 12, wherein the hydrophobic material is oil (e.g., motor oil) and the solid is plastic (e.g., polyethylene).

15. A method of removing gas from polymeric foam, comprising:

dissolving a polymeric foam in a switchable hydrophilicity solvent as defined in claim 1 to form a solution;

combining in any order the solution, water, and $CO_2$ to form a suspension comprising solid polymer and an aqueous liquid comprising a protonated switchable hydrophilicity solvent; and separating the suspension to obtain the solid polymer.

16. The method of claim 15, wherein the switchable hydrophilicity solvent is a water-immiscible compound of formula (10)

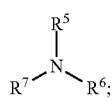  (10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n + m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;

with the proviso that at least one of R$^5$, R$^6$, and R$^7$ is not H.

17. The method of claim 16, wherein the polymeric foam is expanded polystyrene, extruded polystyrene foam, rigid polystyrene containers, high impact thin polystyrene, polystyrene foam packing chips, Styrofoam™, rigid polystyrene foam, or Styrofoam™ packing chips.

18. A method of obtaining substantially pure polymer from polymeric foam, comprising:
dissolving a polymeric foam in a switchable hydrophilicity solvent (SHS) as defined in claim 1 to form a solution;
combining in any order the solution, water, and CO$_2$ to form a suspension comprising solid polymer and an aqueous liquid comprising a protonated form of the SHS; and
separating the suspension to obtain the solid polymer.

19. A method of reducing air or gas content of a polymeric material or a mixture of polymeric materials, comprising:
dissolving a polymeric material in a liquid comprising a water-immiscible compound of formula (10) to form a solution

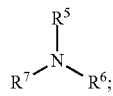
(10)

combining in any order the solution, water, and CO$_2$ to form a composition as defined in claim 1 which is a suspension comprising solid polymer and an aqueous liquid comprising bicarbonate salt of formula (20)

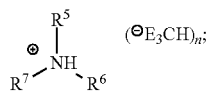
(20)

separating the suspension to obtain the solid polymer;
wherein for formula (10) and formula (2):
R$^5$, R$^6$, and R$^7$ are independently H; a substituted or unsubstituted C$_1$ to C$_{10}$ alkyl group that is linear, branched, or cyclic; a substituted or unsubstituted C$_n$Si$_m$ group where n and m are independently a number from 0 to 10 and n + m is a number from 1 to 10; a substituted or unsubstituted C$_5$ to $_{10}$ aryl group; a substituted or unsubstituted heteroaryl group having 4 to 10 ring atoms;
wherein, optionally, any combination of R$^5$, R$^6$ and R$^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;
with the proviso that at least one of R$^5$, R$^6$, and R$^7$ is not H; and
wherein n is a number from 1 to 6 sufficient to balance the overall charge of the ammonium cation, and E is 0.

20. The method of claim 19, wherein the polymeric product comprises a mixture of polymers.

21. A method for separating a selected water-immiscible compound from a mixture, comprising:
adding a liquid comprising a water-immiscible compound of formula (10) to a first mixture, said first mixture comprising a selected water-immiscible compound that is soluble in the liquid, to form a second mixture

(10)

combining in any order the second mixture, water, and CO$_2$ to form a two-phase liquid mixture having a first hydrophobic phase comprising the selected water-immiscible compound and a second aqueous phase which is a composition as defined in claim 1 comprising bicarbonate salt of formula (20)

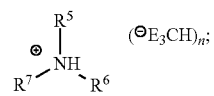
(20)

separating the two phases;
wherein the selected water-immiscible compound is not reactive with the liquid, carbon dioxide or a combination thereof;
wherein for formula (10) and formula (20):
R$^5$, R$^6$, and R$^7$ are independently H; a substituted or unsubstituted C$_1$ to C$_{10}$ alkyl group that is linear, branched, or cyclic; a substituted or unsubstituted C$_n$Si$_m$ group where n and m are independently a number from 0 to 10 and n +m is a number from 1 to 10; a substituted or unsubstituted C$_5$ to C$_{10}$ aryl group; a substituted or unsubstituted heteroaryl group having 4 to 10 ring atoms;
wherein, optionally, any combination of R$^5$, R$^6$ and R$^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;
with the proviso that at least one of R$^5$, R$^6$, and R$^7$ is not H; and
wherein n is a number from 1 to 6 sufficient to balance the overall charge of the ammonium cation, and E is 0.

22. The method of claim 21, wherein the selected water-immiscible compound is soluble or miscible in a water-immiscible compound of formula (10) but is not soluble nor miscible in a compound of formula (20).

23. The method of claim 21, further comprising separating from the second mixture one or more components of the first mixture that is insoluble in the liquid.

24. The method of claim 21, wherein the first mixture is: a mixture of two or more solids wherein a first solid is soluble in the liquid and a second solid is not; or paper bearing ink wherein the ink is soluble in the liquid.

25. The method of claim 6, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

26. A kit comprising a switchable hydrophilicity solvent (SHS), and instructions for use;
wherein the SHS is in the form of a solid bicarbonate salt of formula (20) as defined in claim 9, and wherein the instructions recite steps for removal of $CO_2$ to switch the salt to its neutral hydrophobic form by:
heating the solid bicarbonate salt of formula (20),
placing the solid bicarbonate salt of formula (20) under reduced pressure,
contacting the solid bicarbonate salt of formula (20) with a nonreactive gas that contains substantially no $CO_2$;
both heating the solid bicarbonate salt of formula (2) and contacting the solid bicarbonate salt of formula (20) with a nonreactive gas that contains substantially no $CO_2$; or
both heating the solid bicarbonate salt of formula (20) and placing the solid bicarbonate salt of formula (20) under reduced pressure.

27. The composition of claim 1, further comprising a hydrophobic contaminant,
wherein at least a portion of the hydrophobic contaminant dissolves in the water-immiscible liquid unprotonated form of the SHS; and
wherein when the amount of the dissolved $CO_2$ is sufficient to maintain a substantial amount of the SHS in protonated form, a two-phase liquid mixture results, said two-phase liquid mixture having a hydrophobic liquid phase comprising the hydrophobic contaminant, and an aqueous liquid phase comprising the protonated form of the SHS, said aqueous liquid phase being separable from the hydrophobic liquid phase.

28. The composition of claim 27, wherein the hydrophobic contaminant comprises hydrocarbons or an odorous compound.

29. The composition of claim 27, wherein the SHS comprises a water-immiscible compound of formula (10)

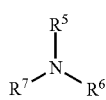
(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;
with the proviso that at least one of $R^5$, $R^6$, and $R^7$ is not H.

30. The composition of claim 27, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

31. The composition of claim 27, further comprising at least one plastic that:
is soluble in the water-immiscible liquid unprotonated form of the SHS, and
forms a precipitate when the amount of the dissolved $CO_2$ is sufficient to maintain the protonated form of the SHS.

32. The composition of claim 31, wherein the at least one plastic comprises polystyrene.

33. The composition of claim 31, wherein the SHS comprises a water-immiscible compound of formula (10)

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof; with the proviso that at least one of $R^5$, $R^6$, and $R^7$ is not H.

34. The composition of claim 31, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,Nt-dipropyl-N,N$^1$-diethylbutane-1,4-diamine, N1,N1,N4,N4-tetraethylbutane-1,4-diamine, or any combination thereof.

35. The composition of claim 1, further comprising a polymeric foam that is soluble in the water-immiscible liquid unprotonated form of the SHS.

36. The composition of claim 35, wherein the polymeric foam is expanded polystyrene, extruded polystyrene foam, polystyrene foam packing chips, Styrofoam™, rigid polystyrene foam, high impact thin polystyrene, or Styrofoam™ packing chips.

37. The composition of claim 35, wherein the SHS comprises a water-immiscible compound of formula (10)

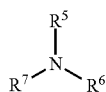

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof; with the proviso that at least one of $R^5$, $R^6$, and $R^7$ is not H.

38. The composition of claim 35, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

39. The composition of claim 35, wherein the polymeric foam forms a precipitate when the amount of the dissolved $CO_2$ is sufficient to maintain the protonated form of the SHS.

40. The composition of claim 1, further comprising a selected water-immiscible substance,
wherein the selected water-immiscible substance dissolves in the water-immiscible liquid unprotonated form of the SHS; and
wherein when the amount of the dissolved $CO_2$ is sufficient to maintain a substantial amount of the SHS in protonated form, a two-phase liquid mixture results, said two-phase liquid mixture having a non-aqueous liquid phase comprising the selected water-immiscible substance, and an aqueous liquid phase comprising the protonated form of the SHS, said aqueous liquid phase being separable from the non-aqueous liquid phase,
wherein the selected water-immiscible substance is not reactive with the SHS, $CO_2$, or a combination thereof.

41. The composition of claim 40, wherein the SHS comprises a water-immiscible compound of formula (10)

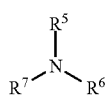

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof;

with the proviso that at least one of $R^5$, $R^6$, and $R^7$ is not H.

42. The composition of claim 40, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

43. The composition of claim 1, further comprising a hydrophobic material,
wherein the hydrophobic material dissolves in the water-immiscible liquid unprotonated form of the SHS; and
wherein when the amount of the dissolved $CO_2$ is sufficient to maintain a substantial amount of the SHS in protonated form, a two-phase liquid mixture results, said two-phase liquid mixture having a hydrophobic liquid phase comprising the hydrophobic material, and an aqueous liquid phase comprising the protonated form of the SHS.

44. The composition of claim 43, wherein the SHS comprises a water-immiscible compound of formula (10)

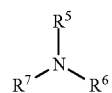

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof;

with the proviso that at least one of $R^5$, $R^6$, and $R^7$ is not H.

45. The composition of claim 43, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

46. The composition of claim 43, wherein the hydrophobic material is oil (e.g. motor oil).

47. The composition of claim 43, wherein said hydrophobic material has been solubilized from a solid material at least partially coated by said hydrophobic material.

48. The composition of claim 1, further comprising a polymeric material or a mixture of polymeric materials, wherein the polymeric material or mixture of polymeric materials is soluble in the water-immiscible liquid unprotonated form of the SHS and forms a precipitate when the amount of the dissolved $CO_2$ is sufficient to maintain the protonated form of the SHS.

49. The composition of claim 48, wherein the SHS comprises a water-immiscible compound of formula (10)

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n +m is a number from 1 to 10; a substituted or unsubstituted $C_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;
with the proviso that at least one of $R^5$, $R^6$, and $R^7$ is not H.

50. The composition of claim 48, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

51. The composition of claim 1, further comprising a selected water-immiscible compound,
wherein the selected water-immiscible compound dissolves in the water- immiscible liquid unprotonated form of the SHS; and
wherein when the amount of the dissolved $CO_2$ is sufficient to maintain a substantial amount of the SHS in protonated form, a two-phase liquid mixture results, said two-phase liquid mixture having a hydrophobic liquid phase comprising the selected water-immiscible compound, and an aqueous liquid phase comprising the protonated form of the SHS, said aqueous liquid phase being separable from the hydrophobic liquid phase,
wherein the selected water-immiscible compound is not reactive with the SHS, $CO_2$, or a combination thereof.

52. The composition of claim 51, wherein the SHS comprises a water-immiscible compound of formula (10)

(10)

where $R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n +m is a number from 1 to 10; a substituted or unsubstituted $C_5$ to $C_{10}$ aryl group; a substituted or unsubstituted heteroaryl group having 4 to 10 ring atoms;
wherein, optionally, any combination of $R^5$, $R^6$ and $R^7$, taken together with the nitrogen atom to which they are attached, are joined to form a ring;
wherein a substituent is independently alkyl, alkenyl, alkynyl, aryl, aryl halide, heteroaryl, non-aromatic ring, Si(alkyl)$_3$, Si(alkoxy)$_3$, halo, alkoxy, amino, ester, amide, thioether, alkylcarbonate, phosphine, thioester, or a combination thereof;
with the proviso that at least one of $R^5$, $R^6$, and $R^7$ is not H.

53. The composition of claim 51, wherein the SHS comprises N-ethylpiperidine, N,N,N-triethylamine, N,N-diethyl-N-methylamine, N,N-dimethyl-N-cyclohexylamine, N,N-diethyl-N-cyclohexylamine, N,N-dimethyl-N-hexylamine, N,N-diethyl-N-butylamine, N,N-dipropyl-N-methylamine, N-butylpyrrolidine, N,N'-dipropyl-N,N'-diethylbutane-1,4-diamine, N1,N1,N4,N4-tetraethylbutane-1,4-diamine, or any combination thereof.

54. The composition of claim 51, wherein the selected water-immiscible compound is obtained from a mixture of two or more solids wherein a first solid is soluble in the liquid unprotonated form of the SHS and a second solid is not, or paper bearing ink wherein the ink is soluble in the liquid unprotonated form of the SHS.

55. A composition comprising:
water or an aqueous liquid;
dissolved $CO_2$ from a source other than air;
a switchable hydrophilicity solvent (SHS) that is an amine, wherein the SHS reversibly interconverts from a water-miscible, protonated form to a water-immiscible, liquid, unprotonated form when the amount of the dissolved $CO_2$ is insufficient to maintain the protonated form of the SHS; and
a selected water-immiscible compound;
wherein the dissolved $CO_2$ can be removed by exposing the composition to (i) heat, (ii) a flushing gas, (iii) reduced pressure, or (iv) any combination thereof;
wherein the selected water-immiscible compound dissolves in the water- immiscible liquid unprotonated form of the SHS;
wherein when the amount of the dissolved $CO_2$ is sufficient to maintain a substantial amount of the SHS in protonated form, a two-phase liquid mixture results, said two-phase liquid mixture having a hydrophobic liquid phase comprising the selected water-immiscible compound, and an aqueous liquid phase comprising the protonated form of the SHS, said aqueous liquid phase being separable from the hydrophobic liquid phase;
wherein the selected water-immiscible compound is not reactive with the SHS, $CO_2$, or a combination thereof; and
wherein the selected water-immiscible compound is obtained from oil-contaminated soil or oil-sands.

56. A composition comprising:
water or an aqueous liquid;
dissolved $CO_2$ from a source other than air;
a switchable hydrophilicity solvent (SHS) that is an amine, wherein the SHS reversibly interconverts from a water-miscible, protonated form to a water-immiscible, liquid, unprotonated form when the amount of the dissolved $CO_2$ is insufficient to maintain the protonated form of the SHS; and a selected water-immiscible compound;

wherein the dissolved $CO_2$ can be removed by exposing the composition to (i) heat, (ii) a flushing gas, (iii) reduced pressure, or (iv) any combination thereof;

wherein the selected water-immiscible compound dissolves in the water-immiscible liquid unprotonated form of the SHS;

wherein when the amount of the dissolved $CO_2$ is sufficient to maintain a substantial amount of the SHS in protonated form, a two-phase liquid mixture results, said two-phase liquid mixture having a hydrophobic liquid phase comprising the selected water-immiscible compound, and an aqueous liquid phase comprising the protonated form of the SHS, said aqueous liquid phase being separable from the hydrophobic liquid phase;

wherein the selected water-immiscible compound is not reactive with the SHS, $CO_2$, or a combination thereof; and wherein the selected water-immiscible compound is obtained from drilling fines.

57. A method for separating a selected water-immiscible compound from a mixture, comprising:

adding a liquid comprising a water-immiscible compound of formula (10) to a first mixture, said first mixture comprising a selected water-immiscible compound that is soluble in the liquid, to form a second mixture

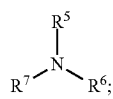

(10)

combining in any order the second mixture, water, and $CO_2$ to form a two-phase liquid mixture having a first hydrophobic phase comprising the selected water-immiscible compound and a second aqueous phase which is a composition as defined in claim 1 comprising bicarbonate salt of formula (20)

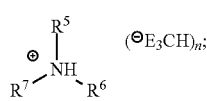

(20)

separating the two phases;

wherein the selected water-immiscible compound is not reactive with the liquid, carbon dioxide or a combination thereof;

wherein for formula (10) and formula (20):

$R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n +m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, $R^6$ and $R^7$, taken together with the nitrogen atom to which they are attached, are joined to form a ring;

wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof;

with the proviso that at least one of $R^5$, $R^6$, and $R^7$ is not H; and wherein n is a number from 1 to 6 sufficient to balance the overall charge of the ammonium cation, and E is O; and wherein the first mixture is oil-contaminated soil or oil-sands.

58. A method for separating a selected water-immiscible compound from a mixture, comprising:

adding a liquid comprising a water-immiscible compound of formula (10) to a first mixture, said first mixture comprising a selected water-immiscible compound that is soluble in the liquid, to form a second mixture

(10)

combining in any order the second mixture, water, and $CO_2$ to form a two-phase liquid mixture having a first hydrophobic phase comprising the selected water-immiscible compound and a second aqueous phase which is a composition as defined in claim 1 comprising bicarbonate salt of formula (20)

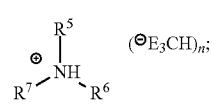

(20)

separating the two phases;

wherein the selected water-immiscible compound is not reactive with the liquid, carbon dioxide or a combination thereof;

wherein for formula (10) and formula (20):

$R^5$, $R^6$, and $R^7$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n +m is a number from 1 to 10; a substituted or unsubstituted $C_5$ to $C_{10}$ aryl group; a substituted or unsubstituted heteroaryl group having 4 to 10 ring atoms;

wherein, optionally, any combination of $R^5$, and $R^7$, taken together with the nitrogen atom to which they are attached, are joined to form a ring;

wherein a substituent is independently alkyl, alkenyl, alkynyl, aryl, aryl halide, heteroaryl, non-aromatic ring, $Si(alkyl)_3$, $Si(alkoxy)_3$, halo, alkoxy, amino, ester, amide, thioether, alkylcarbonate, phosphine, thioester, or a combination thereof;

with the proviso that at least one of $R^5$, $R^6$, and $R^7$ is not H; and wherein n is a number from 1 to 6 sufficient to balance the overall charge of the ammonium cation, and E is 0; and wherein the first mixture is drilling fines.

* * * * *